United States Patent
Whitesides et al.

(10) Patent No.: US 9,678,088 B2
(45) Date of Patent: Jun. 13, 2017

(54) MULTIPHASE SYSTEMS FOR DIAGNOSIS OF SICKLE CELL DISEASE

(71) Applicants: President and Fellows of Harvard College, Cambridge, MA (US); Children's Medical Center Corporation, Boston, MA (US); The Brigham and Women's Hospital, Inc., Boston, MA (US)

(72) Inventors: George M. Whitesides, Newton, MA (US); Ashok A. Kumar, Medford, MA (US); Jonathan W. Hennek, Somerville, MA (US); Caeul Lim, Boston, MA (US); Yovany Moreno, Cambridge, MA (US); Charles R. Mace, Auburn, NY (US); Manoj T. Duraisingh, Cambridge, MA (US); Matthew R. Patton, Cambridge, MA (US); Si-yi Ryan Lee, Cambridge, MA (US); Gaetana D'Alesio-Spina, Cambridge, MA (US); Carlo Brugnara, Boston, MA (US); Thomas P. Stossel, Boston, MA (US)

(73) Assignees: President and Fellows of Harvard College, Cambridge, MA (US); Children's Medical Center Corporation, Boston, MA (US); The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 14/785,980

(22) PCT Filed: Apr. 28, 2014

(86) PCT No.: PCT/US2014/035697
§ 371 (c)(1),
(2) Date: Oct. 21, 2015

(87) PCT Pub. No.: WO2014/176595
PCT Pub. Date: Oct. 30, 2014

(65) Prior Publication Data
US 2016/0124001 A1    May 5, 2016

Related U.S. Application Data

(60) Provisional application No. 61/816,227, filed on Apr. 26, 2013.

(51) Int. Cl.
| | |
|---|---|
| *G01N 33/49* | (2006.01) |
| *G01N 33/80* | (2006.01) |
| *G01N 15/05* | (2006.01) |
| *G01N 15/00* | (2006.01) |

(52) U.S. Cl.
CPC ............ *G01N 33/80* (2013.01); *G01N 15/05* (2013.01); *G01N 33/491* (2013.01); *G01N 2015/003* (2013.01); *G01N 2015/0073* (2013.01); *G01N 2015/0076* (2013.01); *G01N 2800/22* (2013.01)

(58) Field of Classification Search
None
See application file for complete search history.

(56) References Cited

U.S. PATENT DOCUMENTS

| 9,176,105 B2 * | 11/2015 | Mace | B03B 5/28 |
| 2004/0052857 A1 * | 3/2004 | Keating | B82Y 5/00 |
| | | | 424/490 |

FOREIGN PATENT DOCUMENTS

| WO | WO-2012/024688 A1 | 2/2012 |
| WO | WO-2012/024690 A1 | 2/2012 |
| WO | WO-2012/024691 A1 | 2/2012 |
| WO | WO-2012/024693 A1 | 2/2012 |

OTHER PUBLICATIONS

Fabry M. et al. Dense Cells in Sickle Cell Anemia. Blood 64(5)1042-1046, Nov. 1984.*
Mace C. et al. Aqueous Multiphase Systems of Polymers and Surfactants Provide Self Assembling Step Gradients in Density. JACS 134:9094-9097, 2012.*
Baudin et al., "Heterogeneity of Sickle Cell Disease as Shown by Density Profiles: Effects of Fetal Hemoglobin and Alpha Thalassemia." Haematologia, vol. 19, No. 3, pp. 177-184, (1986).
Grover et al., "Measuring single-cell density". Proc. Natl. Acad. Sci. USA, vol. 108, No. 27, pp. 10992-10996, Jul. 5, 2011.
Milligan et al., "A non-electrolyte haemolysis assay for diagnosis and prognosis of sickle cell disease", J. Physiol. 591(Pt 6), 1463-1474 (2013).
International Preliminary Report on Patentability mailed Nov. 5, 2015, in the International Application No. PCT/US14/35697, 8 pages.
International Search Report and Written Opinion mailed on Nov. 7, 2014, in the International Application No. PCT/US14/35697, 16 pages.
Rodgers et al., "Cell heterogeneity in sickle cell disease: Quantitation of the erythrocyte density profile", The Journal of Laboratory and Clinical Medicine, vol. 106, No. 1, pp. 30-37, Jul. 1985.
Seakins et al., "Erythrocyte Hb-S Concentration An Important Factor in the Low Oxygen Affinity of Blood in Sickle Cell Anemia", The Journal of Clinical Investigation, vol. 52, pp. 422-432, Feb. 1973.

(Continued)

*Primary Examiner* — Ralph Gitomer
(74) *Attorney, Agent, or Firm* — Wilmer Cutler Pickering Hale and Dorr LLP

(57) ABSTRACT

An aqueous multi-phase system for diagnosis of sickle cell disease is described, including two or more phase-separated phases including: a first aqueous phase including a first phase component and having a first density between about 1.025 g/cm$^3$ and about 1.095 g/cm$^3$; and a second aqueous phase including a second phase component and having a second density between about 1.100 g/cm$^3$ and about 1.140 g/cm$^3$; wherein the first density is lower than the second density; and each of the first and second phase components include at least one polymer.

16 Claims, 38 Drawing Sheets

(56) References Cited

OTHER PUBLICATIONS

Stocks, Susan, "Cell Separations by Immunoaffinity Partition," A Thesis Submitted in Partial Fulfillment of the Requirements for the Degree of Doctor of Philosophy in the Faculty of Graduate Studies, Department of Chemistry, The University of British Columbia, Canada, pp. 1-178, Oct. 2, 1989, available at: (<https://circle.ubc.ca/bitstream/id/99911/UBC_>1989_A1%20S76.pdf).

Uzunova et al., "Free Heme and the Polymerization of Sickle Cell Hemoglobin," Biophysical Journal, vol. 99, pp. 1976-1985, Sep. 2010.

* cited by examiner

FIG. 20A
tube-in-tube
FIG. 20B
hole-in-tube
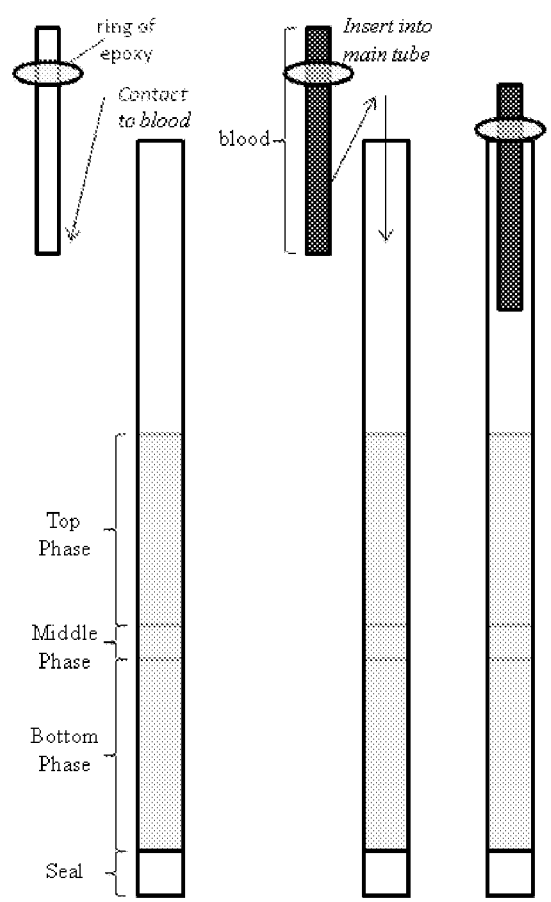
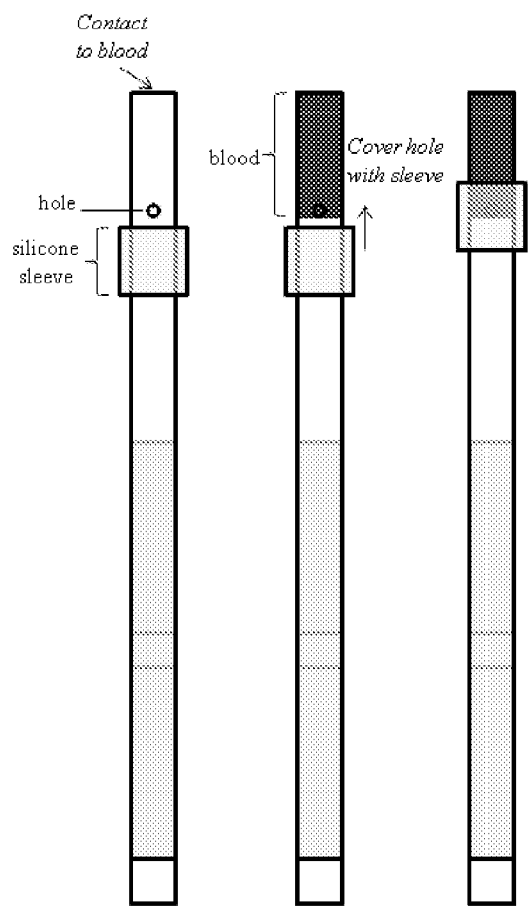

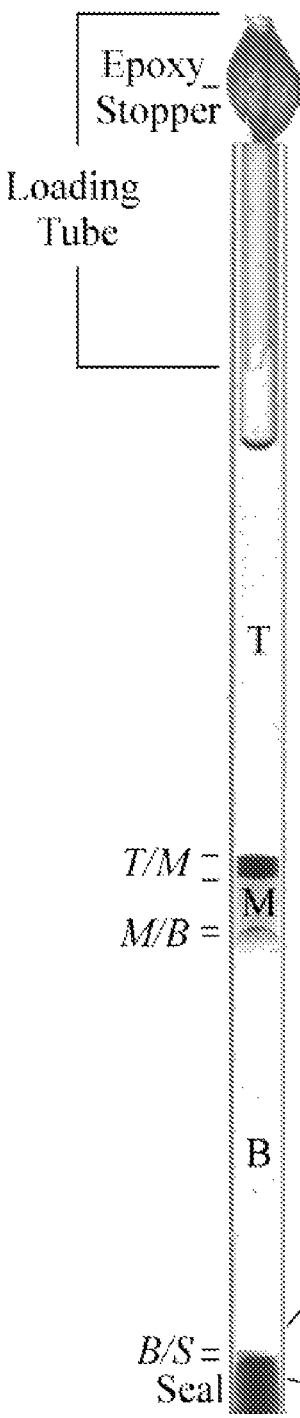
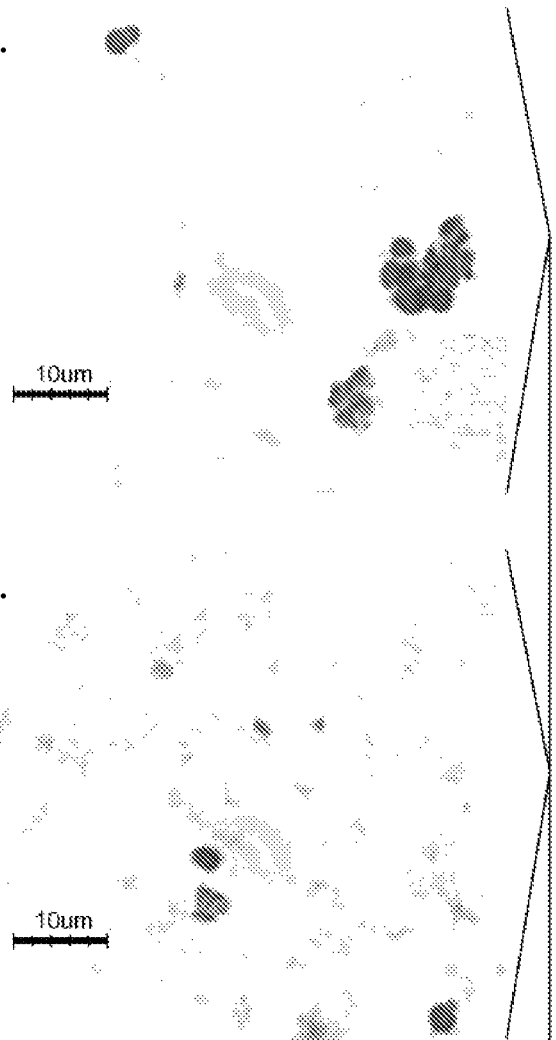
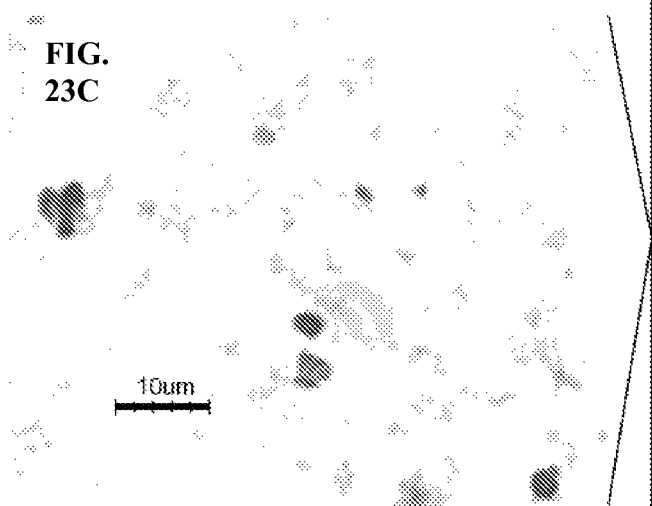
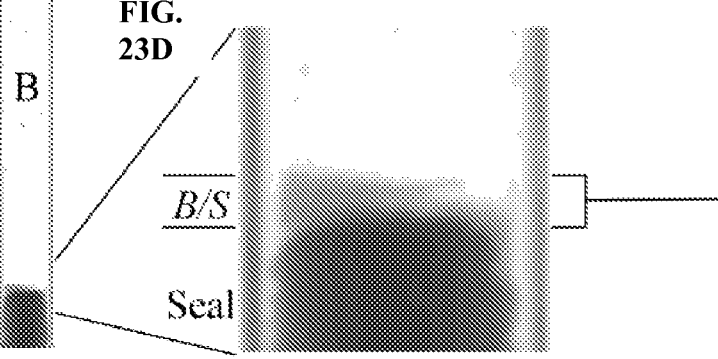
FIG. 23A
FIG. 23B
FIG. 23C
FIG. 23D

FIG. 35
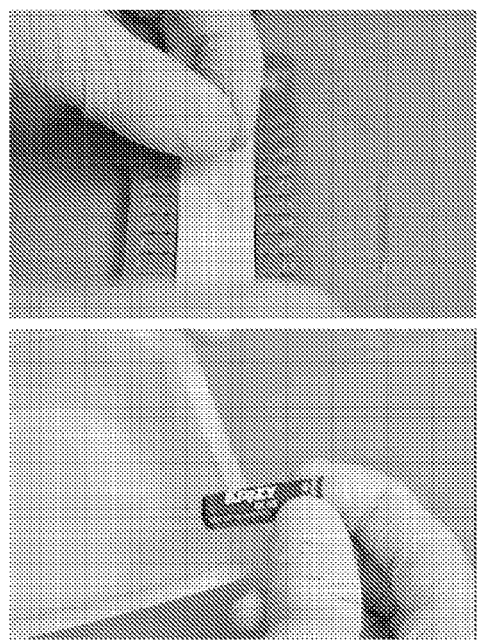
Bottom
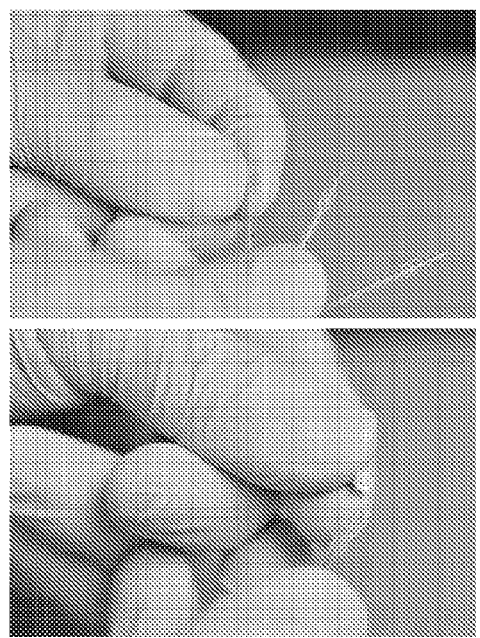
Top

FIG. 36
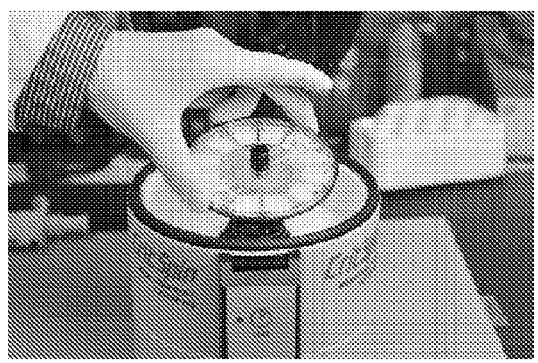
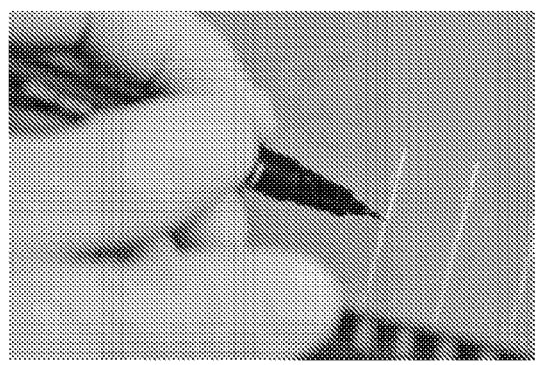

_US 9,678,088 B2_

MULTIPHASE SYSTEMS FOR DIAGNOSIS OF SICKLE CELL DISEASE

RELATED APPLICATION

This application is a National Stage Entry of PCT International Application No. PCT/US14/35697, filed Apr. 28, 2014, which claims priority to U.S. Provisional Application 61/816,227, filed Apr. 26, 2013, the contents of which are hereby incorporated by reference herein in its entirety. The present application is generally related to WO2012/024688, filed on Aug. 22, 2011, WO2012/024693, filed on Aug. 22, 2011, WO2012/024690, filed on Aug. 22, 2011, and WO2012/024691, filed on Aug. 22, 2011, all of which are hereby incorporated by reference herein in their entirety.

INCORPORATION BY REFERENCE

All patents, patent applications and publications cited herein are hereby incorporated by reference in their entirety in order to more fully describe the state of the art as known to those skilled therein as of the date of the invention described herein.

GOVERNMENT FUNDING CLAUSE

This invention was made with support from the United States government under Grant No. NHLBI R01HL117329 awarded by the National Institute of Health, the NDSEG fellowship from the Office of Naval Research. The United States government has certain rights to this invention.

BACKGROUND

Aqueous mixtures of two polymers such as poly(ethylene glycol) (PEG) and dextran can separate spontaneously into two aqueous phases, called aqueous two-phase systems. Phase separation in aqueous solutions of polymers is an extraordinary and underexplored phenomenon. When two aqueous solutions of polymers are mixed, the resulting system is not homogeneous; rather, two discrete phases, or layers, form. These layers are ordered according to density and arise from the limited interaction of the polymers for one another. In these systems, each phase predominantly consists of water (upwards of 70-90% (w/v)), while the polymer component is present in concentrations ranging from micromolar to millimolar. A low interfacial tension and rapid mass transfer of water-soluble molecules across the boundary characterize the interface between layers.

SUMMARY

Described herein are multi-phase systems ("MPS") comprising two or more phases having different densities and methods of separating or analyzing biological analytes of interest using these multi-phase systems. In some embodiments, MPS as described herein are used to separate biological analytes from each other in the sample when the analytes migrate to phases characteristic of their densities, dynamically or thermodynamically. Non-limiting examples of the biological analytes include normal erythrocyte with hemoglobin Hb AA, Hb CC, and Hb AS, sickle cell erythrocyte with hemoglobin Hb SS, Hb SC, HbSbeta$^+$, HbSD, HbSE and HbSO, reticulocyte, predominantly hypochromic red blood cells (e.g. iron deficiency anemia (IDA)), predominantly microcytic red blood cells (e.g. β-thalassemia trait (β-TT)), normal red blood cells, and white blood cells. Method of using the multi-phase systems described herein for biological analysis and kit including these multi-phase systems or their corresponding phase components and instructions for making and using these multi-phase systems for biological analysis are also described.

As used herein, the use of the phrase "polymer" includes, but is not limited to, the homopolymer, copolymer, terpolymer, random copolymer, and block copolymer. Block copolymers include, but are not limited to, block, graft, dendrimer, and star polymers. As used herein, copolymer refers to a polymer derived from two monomeric species; similarly, a terpolymer refers to a polymer derived from three monomeric species. The polymer also includes various morphologies, including, but not limited to, linear polymer, branched polymer, random polymer, crosslinked polymer, and dendrimer systems. As an example, polyacrylamide polymer refers to any polymer including polyacrylamide, e.g., a homopolymer, copolymer, terpolymer, random copolymer, block copolymer or terpolymer of polyacrylamide. Polyacrylamide can be a linear polymer, branched polymer, random polymer, crosslinked polymer, or a dendrimer of polyacrylamide.

As used herein, the MPSs described herein may be used for analysis of mammalian blood and/or separation of biological analytes from the mammalian blood. In some embodiments, the mammal is human.

Methods of using the MPS to analyze a liquid sample containing a biological analyte are described herein. In some embodiments, the MPS is formed first and the sample is added to the MPS afterwards. In other embodiments, the phase components from each phases, a solvent such as water and the sample are mixed together to form the MPS with the analyte already separated or analyzed by the MPS. In some embodiments, a liquid sample containing a biological analyte, e.g., a mammalian blood sample, is mixed with the multi-phase system and an interface is formed between the liquid sample and the top phase (if the top phase has a density lower than the liquid sample) or the bottom phase (if the bottom phase has a density lower than the liquid sample).

In some embodiments, the phase component is a polymer or a combination of two or more polymers.

As used herein, AMPS refers to an aqueous multi-phase polymer system. ATPS refers to an aqueous two-phase polymer system.

As used herein, an aqueous multi-phase polymer system comprises two or more polymer aqueous solutions or phases, which are phase-separated and in which at least two aqueous solutions each comprise a polymer. In some embodiments, the aqueous multi-phase polymer system can be combined with one or more immiscible organic phases to form a multi-phase system.

As used herein, the phrase "mixture" refers to the combination of two components, which may be mixed or layered one on top of another.

As used herein, when specific values are disclosed, the ranges bounded by any of the specific values are also contemplated.

As used herein, the phrase "at the interface" of the adjacent phases of the MPS includes the situation where the biological analytes of interest is between the two adjacent phases or close to the border of one of the two adjacent phases.

In one aspect, an aqueous multi-phase system for diagnosis of iron deficiency anemia is described, comprising two or more phase-separated phases comprising:

a first aqueous phase comprising a first phase component and having a first density between about 1.025 g/cm$^3$ and about 1.085 g/cm$^3$; and a second aqueous phase comprising a second phase component and having a second density between about 1.075 g/cm$^3$ and about 1.095 g/cm$^3$;

wherein the first density is lower than the second density; and each of the first and second phase components comprises at least one polymer.

In any one of the previous embodiments, the first density is about 1.025-1.080 g/cm$^3$, 1.025-1.075 g/cm$^3$, 1.025-1.070 g/cm$^3$, 1.025-1.065 g/cm$^3$, 1.025-1.060 g/cm$^3$, 1.025-1.055 g/cm$^3$, 1.025-1.050 g/cm$^3$, 1.030-1.080 g/cm$^3$, 1.030-1.075 g/cm$^3$, 1.030-1.070 g/cm$^3$, 1.030-1.065 g/cm$^3$, 1.030-1.060 g/cm$^3$, 1.030-1.055 g/cm$^3$, 1.030-1.050 g/cm$^3$, 1.040-1.080 g/cm$^3$, 1.040-1.075 g/cm$^3$, 1.040-1.070 g/cm$^3$, 1.040-1.065 g/cm$^3$, 1.040-1.060 g/cm$^3$, 1.040-1.055 g/cm$^3$, 1.040-1.050 g/cm$^3$, 1.050-1.080 g/cm$^3$, 1.050-1.075 g/cm$^3$, 1.050-1.070 g/cm$^3$, 1.050-1.065 g/cm$^3$, 1.050-1.060 g/cm$^3$, 1.050-1.055 g/cm$^3$, 1.055-1.080 g/cm$^3$, 1.055-1.075 g/cm$^3$, 1.055-1.070 g/cm$^3$, 1.055-1.065 g/cm$^3$, 1.055-1.060 g/cm$^3$, 1.060-1.080 g/cm$^3$, 1.060-1.075 g/cm$^3$, 1.060-1.070 g/cm$^3$, 1.060-1.065 g/cm$^3$, 1.065-1.080 g/cm$^3$, 1.065-1.075 g/cm$^3$, 1.070-1.080 g/cm$^3$, 1.075-1.080 g/cm$^3$, or 1.075-1.085 g/cm$^3$.

In any one of the previous embodiments, the second density is about 1.075-1.090 g/cm$^3$, 1.075-1.085 g/cm$^3$, 1.075-1.080 g/cm$^3$, 1.080-1.095 g/cm$^3$, 1.080-1.090 g/cm$^3$, 1.080-1.085 g/cm$^3$, 1.085-1.095 g/cm$^3$, or 1.085-1.090 g/cm$^3$.

In any one of the previous embodiments, the first density is about 1.070-1.083 g/cm$^3$ and the second density is about 1.080-1.085 g/cm$^3$.

In any one of the previous embodiments, the first and second phase components are dextran and Ficoll, respectively.

In any one of the previous embodiments, the aqueous multiphase further includes:

a third aqueous phase comprising a third phase component and having a third density between about 1.073 g/cm$^3$ and about 1.093 g/cm$^3$;

wherein the third density is higher than the first density but lower than the second density; and the third phase component comprises at least one polymer.

In any one of the previous embodiments, the third density is less than about 0.002 g/cm$^3$, 0.0019 g/cm$^3$, 0.0018 g/cm$^3$, 0.0017 g/cm$^3$, 0.0016 g/cm$^3$, 0.0015 g/cm$^3$, 0.0014 g/cm$^3$, 0.0013 g/cm$^3$, 0.0012 g/cm$^3$, 0.0011 g/cm$^3$, 0.0010 g/cm$^3$, 0.0009 g/cm$^3$, 0.0008 g/cm$^3$, 0.0007 g/cm$^3$, 0.0006 g/cm$^3$, 0.0005 g/cm$^3$, 0.0004 g/cm$^3$, 0.0003 g/cm$^3$, 0.0002 g/cm$^3$, or 0.0001 g/cm$^3$ lower than the second density.

In any one of the previous embodiments, the first, third, and second densities are about 1.040-1.055 g/cm$^3$, 1.075-1.085 g/cm$^3$, and 1.080-1.085 g/cm$^3$, respectively.

In any one of the previous embodiments, the first, third, and second phase components are PVA, dextran and Ficoll, respectively.

In any one of the previous embodiments, the first, second, and third phase components are each selected from the group consisting of Caboxy-polyacrylamide, Dextran, Ficoll, N,N-dimethyldodecylamine N-oxide, poly(2-ethyl-2-oxazoline), poly(acrylic acid), poly(ethylene glycol), poly (methacrylic acid), poly(vinyl alcohol), polyacrylamide, polyethyleneimine, hydroxyethyl cellulose, poly(2-acrylamido-2-methyl-1-propanesulfonic acid), polyvinylpyrrolidone, Nonyl, polyallylamine, (hydroxypropyl)methyl cellulose, diethylaminoethyl-dextran, nonylphenol polyoxyethylene 20, copolymer, terpolymer, block copolymer, random polymer, linear polymer, branched polymer, crosslinked polymer, and dendrimer system thereof.

In any one of the previous embodiments, the concentration of the first phase component in the first phase or the concentration of the second phase component in the second phase is between about 1-40% (w/v).

In any one of the previous embodiments, the concentration of the first phase component in the first phase or the concentration of the second phase component in the second phase is about 5%-25%, 10%-20%, or 15%-20% (w/v).

In any one of the previous embodiments, the concentration of the third phase component in the third phase is between about 1-40% (w/v) or about 5%-25%, 10%-20%, or 15%-20 (w/v).

In any one of the previous embodiments, the aqueous multi-phase system is isotonic.

In another aspect, a method of diagnosing iron deficiency anemia or β-thalessemia trait is described, comprising:

(a) providing an aqueous multi-phase system described herein, wherein the multi-phase system comprises two phases phase-separating to form an interface between first and second phases;

(b) adding a mammalian blood sample comprising red blood cells to the multi-phase system to allow the red blood cells to migrate to a location(s) in the multi-phase system characteristic of their density; and (c) observing the presence or absence of red blood cells at the interface of the first and second aqueous phases; wherein the presence of red blood cells at the interface of the first and second aqueous phases indicates iron deficiency anemia red blood cells or β-thalessemia trait red blood cells.

In any one of the previous embodiments, step (b) comprises centrifuging the multi-phase system and the mammalian blood sample.

In any one of the previous embodiments, step (b) comprises allowing the red blood cells in the mammalian blood sample to reach thermodynamic equilibrium in the multi-phase system.

In any one of the previous embodiments, the presence or absence of iron deficiency anemia red blood cells or β-thalessemia trait red blood cells is observed by naked eye or digital quantification analysis.

In any one of the previous embodiments, the volume ratio of the mammalian blood sample to the multiphase system is about 0.15-4:1, 0.2-2:1, or 0.3-1:1.

In yet another aspect, a method of diagnosing iron deficiency anemia and β-thalessemia trait is described, comprising:

(a) providing an aqueous multi-phase system described herein, wherein the multi-phase system comprises three phases having interfaces between the first and third phases and between the third and second phases;

(b) adding a mammalian blood sample comprising red blood cells to the multi-phase system to allow the red blood cells to migrate to a location(s) in the multi-phase system characteristic of their density; and (c) observing the presence or absence of iron deficiency anemia red blood cells at the interface of the first and third aqueous phases, and the presence or absence of the β-thalessemia trait red blood cells at the interface of or in the third and second aqueous phases.

In any one of the previous embodiments, step (b) comprises centrifuging the multi-phase system and the mammalian blood sample.

In any one of the previous embodiments, the multi-phase system is a three-phase system.

In any one of the previous embodiments, the method comprises obtaining the size and/or density distribution profile of the iron deficiency anemia red blood cells or β-thalessemia trait red blood cells.

In any one of the previous embodiments, step (b) comprises allowing the analyte in the mammalian blood sample to reach thermodynamic equilibrium in the multi-phase system.

In any one of the previous embodiments, the presence or absence of iron deficiency anemia red blood cells or β-thalessemia trait red blood cells is observed by naked eye or digital quantification analysis.

In any one of the previous embodiments, the volume ratio of the mammalian blood sample to the multiphase system is about 0.15-4:1, 0.2-2:1, or 0.3-1:1.

In any one of the previous embodiments, during migration the red blood cells contacts one or more of the two or more phases sequentially.

In any one of the previous embodiments, the mammalian blood sample is a human blood sample.

In yet another aspect, a kit for the diagnosis of iron deficiency anemia using a multi-phase system is described, comprising:
a) at least a first and second phase components each comprising at least one polymer; and
b) instructions for:
(i) combining the first and second phase components and water, each in a predetermined amount, to create a multi-phase system described herein, wherein the multiple phases having an interface between the first and second phases; and
(ii) adding a mammalian blood sample to the multi-phase system to allow the red blood cells to migrate to locations(s) characteristic of their densities; and
(iii) observing the presence or absence of red blood cells at the interface of the first and second aqueous phases; wherein
the presence of red blood cells at the interface of the first and second aqueous phases indicates iron deficiency anemia red blood cells or β-thalessemia trait red blood cells.

In yet another aspect, a kit for the diagnosis of iron deficiency anemia and or β-thalessemia trait using a multi-phase system is describe, comprising:
a) at least a first, second, and third phase components each comprising at least one polymer; and
b) instructions for:
(i) combining the first, second, and third phase components and water, each in a predetermined amount, to create a multi-phase system of described herein, wherein the multiple phases comprise interfaces between the first and third phases and between the third and second phases; and
(ii) adding a mammalian blood sample to the multi-phase system to allow the red blood cells to migrate to locations(s) characteristic of their densities; and
(iii) observing the presence or absence of iron deficiency anemia red blood cells at the interface of the first and third aqueous phases, and the presence or absence of the β-thalessemia trait red blood cells at the interface of or in the third and second aqueous phases.

In any one of the previous embodiments, the mammalian blood sample is a human blood sample.

In yet another aspect, an aqueous multi-phase system for enriching reticulocytes content in a biological sample is described, comprising two or more phase-separated phases comprising:
a first aqueous phase comprising a first phase component and having a first density between about 1.025 $g/cm^3$ and about 1.090 $g/cm^3$; and
a second aqueous phase comprising a second phase component and having a second density between about 1.065 $g/cm^3$ and about 1.095 $g/cm^3$;
wherein
the first density is lower than the second density; and
each of the first and second phase components comprises at least one polymer.

In any one of the previous embodiments, the first density is about 1.050-1.089 $g/cm^3$, 1.050-1.085 $g/cm^3$, 1.050-1.080 $g/cm^3$, 1.050-1.075 $g/cm^3$, 1.050-1.070 $g/cm^3$, 1.050-1.065 $g/cm^3$, 1.050-1.060 $g/cm^3$, 1.060-1.089 $g/cm^3$, 1.060-1.085 $g/cm^3$, 1.060-1.080 $g/cm^3$, 1.060-1.075 $g/cm^3$, 1.060-1.070 $g/cm^3$, 1.060-1.065 $g/cm^3$, 1.065-1.089 $g/cm^3$, 1.065-1.085 $g/cm^3$, 1.065-1.080 $g/cm^3$, 1.065-1.075 $g/cm^3$, or 1.065-1.070 $g/cm^3$.

In any one of the previous embodiments, the first density is about 1.060-1.070 $g/cm^3$, 1.070-1.080 $g/cm^3$, or 1.080-1.090 $g/cm^3$.

In any one of the previous embodiments, the second density is about 1.065-1.090 $g/cm^3$, 1.065-1.085 $g/cm^3$, 1.065-1.080 $g/cm^3$, 1.065-1.075 $g/cm^3$, 1.065-1.070 $g/cm^3$, 1.070-1.085 $g/cm^3$, 1.070-1.080 $g/cm^3$, 1.070-1.075 $g/cm^3$, 1.080-1.090 $g/cm^3$, 1.080-1.085 $g/cm^3$, or 1.075-1.080 $g/cm^3$.

In any one of the previous embodiments, the second density is about 1.070-1.080 $g/cm^3$, 1.080-1.090 $g/cm^3$, or 1.090-1.095 $g/cm^3$.

In any one of the previous embodiments, the first and second densities are about 1.067-1.086 $g/cm^3$ and 1.070-1.089 $g/cm^3$, respectively.

In any one of the previous embodiments, the multi-phase system is hypertonic, isotonic, or hypotonic.

In any one of the previous embodiments, the multi-phase system is hypertonic.

In any one of the previous embodiments, the multi-phase system has a tonicity of about 320-340, 320-330, or 330-340 mOsm/kg.

In any one of the previous embodiments, the first and second phase components are each selected from the group consisting of Caboxy-polyacrylamide, Dextran, Ficoll, N,N-dimethyldodecylamine N-oxide, poly(2-ethyl-2-oxazoline), poly(acrylic acid), poly(ethylene glycol), poly(methacrylic acid), poly(vinyl alcohol), polyacrylamide, polyethyleneimine, hydroxyethyl cellulose, poly(2-acrylamido-2-methyl-1-propanesulfonic acid), polyvinylpyrrolidone, Nonyl, polyallylamine, (hydroxypropyl)methyl cellulose, diethylaminoethyl-dextran, nonylphenol polyoxyethylene 20, copolymer, terpolymer, block copolymer, random polymer, linear polymer, branched polymer, crosslinked polymer, and dendrimer system thereof.

In any one of the previous embodiments, the concentration of the first phase component in the first phase or the concentration of the second phase component in the second phase is between about 1-40% (w/v).

In any one of the previous embodiments, the concentration of the first phase component in the first phase or the concentration of the second phase component in the second phase is about 9.0%-12.0% (w/v).

In any one of the previous embodiments, the first and second phase components are dextran and Ficoll, respectively.

In yet another aspect, a method for enriching reticulocytes content in a biological sample is described, comprising:

(a) providing an aqueous multi-phase system described herein, wherein the multi-phase system comprises an interface between the first and second phases; and (b) adding a mammalian blood sample comprising reticulocytes to the multi-phase system to allow the reticulocytes to migrate to the interface between the first and second phases; and (c) collecting a reticulocyte enriched product.

In any one of the previous embodiments, step (b) comprises centrifuging the multi-phase system and the mammalian blood sample.

In any one of the previous embodiments, step (b) comprises allowing the multi-phase system and the mammalian blood sample to reach thermodynamic equilibrium.

In any one of the previous embodiments, the presence of the reticulocytes is observed by naked eye or digital quantification analysis.

In any one of the previous embodiments, the volume ratio of the mammalian blood sample to the multiphase system is about 0.15-4:1, 0.2-2:1, or 0.3-1:1.

In any one of the previous embodiments, the volume ratio of the mammalian blood sample to the multiphase system is about 1:1.

In any one of the previous embodiments, the collected reticulocytes have a reticulocytemia of about more than 10%, 20%, 30%, 40%, 50%, 60%, or 70%, or 10%-70%, or 20%-60%.

In any one of the previous embodiments, the reticulocytes is collected with a yield of more than 0.5%, 1%, 1.5%, 2%, 3%, 4%, 5%, 10%, or 20%, or 0.5%-20%, or 1%-10%.

In any one of the previous embodiments, during migration the reticulocytes contact one or more of the two phases sequentially.

In any one of the previous embodiments, the mammalian blood sample is a human blood sample.

In yet another aspect, a kit for enriching reticulocytes content in a biological sample using a multi-phase system is describe, comprising:

a) at least a first and second phase components each comprising at least one polymer; and b) instructions for:

(i) combining the first and second phase components and water, each in a predetermined amount, to create a multi-phase system described herein, wherein the multiple phases comprises an interface between the first and second phases; and (ii) adding a mammalian blood sample to the multi-phase system to allow the reticulocytes to migrate to the interface between the first and second phases;

(iii) collecting a reticulocyte enriched product.

In any one of the previous embodiments, the mammalian blood sample is a human blood sample.

In yet another aspect, an aqueous multi-phase system for diagnosis of sickle cell disease, comprising two or more phase-separated phases is described, comprising:

a first aqueous phase comprising a first phase component and having a first density between about 1.025 g/cm$^3$ and about 1.140 g/cm$^3$; and a second aqueous phase comprising a second phase component and having a second density between about 1.100 g/cm$^3$ and about 1.140 g/cm$^3$;

wherein the first density is lower than the second density; and each of the first and second phase components comprises at least one polymer.

In any one of the previous embodiments, the first density is about 1.025-1.140 g/cm$^3$, 1.025-1.130 g/cm$^3$, 1.025-1.120 g/cm$^3$, 1.025-1.110 g/cm$^3$, 1.025-1.100 g/cm$^3$, 1.025-1.090 g/cm$^3$, 1.025-1.095 g/cm$^3$, 1.025-1.080 g/cm$^3$, 1.025-1.075 g/cm$^3$, 1.025-1.070 g/cm$^3$, 1.025-1.065 g/cm$^3$, 1.025-1.060 g/cm$^3$, 1.025-1.055 g/cm$^3$, 1.025-1.050 g/cm$^3$, 1.030-1.080 g/cm$^3$, 1.030-1.075 g/cm$^3$, 1.030-1.070 g/cm$^3$, 1.030-1.065 g/cm$^3$, 1.030-1.060 g/cm$^3$, 1.030-1.055 g/cm$^3$, 1.030-1.050 g/cm$^3$, 1.040-1.080 g/cm$^3$, 1.040-1.075 g/cm$^3$, 1.040-1.070 g/cm$^3$, 1.040-1.065 g/cm$^3$, 1.040-1.060 g/cm$^3$, 1.040-1.055 g/cm$^3$, or 1.040-1.050 g/cm$^3$.

In any one of the previous embodiments, the first density is about 1.025-1.030, 1.035-1.050, 1.055-1.070, or 1.075-1.080 g/cm$^3$.

In any one of the previous embodiments, the second density is about 1.110-1.140 g/cm$^3$, 1.110-1.130 g/cm$^3$, 1.110-1.125 g/cm$^3$, 1.110-1.120 g/cm$^3$, 1.115-1.125 g/cm$^3$, 1.115-1.120 g/cm$^3$, or 1.120-1.125 g/cm$^3$.

In any one of the previous embodiments, the second density is about 1.115-1.130 g/cm$^3$.

In any one of the previous embodiments, the first and second densities are about 1.075-1.0798 g/cm$^3$ and 1.120-1.129 g/cm$^3$, respectively.

In any one of the previous embodiments, the aqueous multi-phase system further includes:

a third aqueous phase comprising a third phase component and having a third density between about 1.075 g/cm$^3$ and about 1.120 g/cm$^3$;

wherein the third density is higher than the first density but lower than the second density; and the third phase component comprises at least one polymer.

In any one of the previous embodiments, the third density is about 1.085-1.110 g/cm$^3$, 1.090-1.110 g/cm$^3$, 1.095-1.110 g/cm$^3$, 1.100-1.110 g/cm$^3$, 1.105-1.110 g/cm$^3$, 1.085-1.105 g/cm$^3$, 1.090-1.105 g/cm$^3$, 1.095-1.105 g/cm$^3$, 1.100-1.105 g/cm$^3$, 1.085-1.100 g/cm$^3$, 1.090-1.100 g/cm$^3$, 1.095-1.100 g/cm$^3$, 1.085-1.095 g/cm$^3$, or 1.090-1.095 g/cm$^3$.

In any one of the previous embodiments, the first, third, and second densities are about 1.075-1.083 g/cm$^3$, 1.105-1.110 g/cm$^3$, and 1.115-1.125 g/cm$^3$, respectively.

In any one of the previous embodiments, the first, second, and third phase components are each selected from the group consisting of Caboxy-polyacrylamide, Dextran, Ficoll, N,N-dimethyldodecylamine N-oxide, poly(2-ethyl-2-oxazoline), poly(acrylic acid), poly(ethylene glycol), poly(methacrylic acid), poly(vinyl alcohol), polyacrylamide, polyethyleneimine, hydroxyethyl cellulose, poly(2-acrylamido-2-methyl-1-propanesulfonic acid), polyvinylpyrrolidone, Nonyl, polyallylamine, (hydroxypropyl)methyl cellulose, diethylaminoethyl-dextran, nonylphenol polyoxyethylene 20, copolymer, terpolymer, block copolymer, random polymer, linear polymer, branched polymer, crosslinked polymer, and dendrimer system thereof.

In any one of the previous embodiments, the first and second components are PEG and Ficoll or PEG and PVA, respectively.

In any one of the previous embodiments, the first, third, and second components are PEG, dextran, and PVA, respectively.

In any one of the previous embodiments, the concentration of the first phase component in the first phase or the concentration of the second phase component in the second phase is between about 1-40% (w/v).

In any one of the previous embodiments, the concentration of the first phase component in the first phase or the concentration of the second phase component in the second phase is about 5%-10%, 10%-15%, or 15%-25% (w/v).

In any one of the previous embodiments, the concentration of the third phase component in the third phase is between about 1-40%, 5%-10%, 10%-15%, or 15%-25% (w/v).

In any one of the previous embodiments, the aqueous multi-phase system is isotonic.

In any one of the previous embodiments, the aqueous multi-phase system has a pH of about 7.3-7.5.

In any one of the previous embodiments, the aqueous multi-phase system further includes Nycodenz.

In yet another aspect, a method of diagnosing sickle cell disease is described, comprising:
  (a) providing an aqueous multi-phase system described herein, wherein the multi-phase system comprises an interface between the first and second phases; and
  (b) adding a mammalian blood sample comprising erythrocytes to the multi-phase system to allow the erythrocytes to migrate to a location(s) in the multi-phase system characteristic of their density; and
  (c) observing the presence or absence of erythrocytes below the second phase;
wherein the presence of erythrocytes below the second phase indicates sickle cell disease.

In any one of the previous embodiments, step (b) comprises adding the mammalian blood sample to the multi-phase system in a container to allow the multiple phases to phase-separate to form an interface between the second phase and the bottom of the container and observe the presence or absence of erythrocytes at the interface between the second phase and the bottom of the container.

In yet another aspect, a method of diagnosing subtypes of sickle cell disease is described, comprising:
  (a) providing an aqueous multi-phase system described herein, wherein the multi-phase system comprises interfaces between the first and third phases and between first and second phases, respectively; and
  (b) adding a mammalian blood sample comprising erythrocytes to the multi-phase system to allow the erythrocytes to migrate to a location(s) in the multi-phase system characteristic of their density; and
  (c) observing the presence or absence of erythrocytes at the interfaces of the first and third aqueous phases and of the third and second aqueous phases;
wherein
  the presence of erythrocyte below the second phase indicates sickle cell disease;
  a pattern that the amount of erythrocytes present at the interface of the first and third phases is more than the amount of erythrocytes present at the interface of the third and second phases indicates homozygous sickle cell disease (Hb SS); and
  a pattern that the amount of erythrocytes present at the interface of the third and second phases is about the same or more than the amount of erythrocytes present at the interface of the first and third phases indicates hemoglobin sickle cell disease (Hb SC).

In any one of the previous embodiments, the pattern that the amount of erythrocytes present at the interface of the first and third phases is significantly more than the amount of erythrocytes present at the interface of the third and second phases indicates homozygous sickle cell disease (Hb SS).

In any one of the previous embodiments, step (b) comprises centrifuging the multi-phase system and the mammalian blood sample.

In any one of the previous embodiments, step (b) comprises allowing the cells in the mammalian blood sample to reach thermodynamic equilibrium in the multi-phase system.

In any one of the previous embodiments, the presence or absence of erythrocytes is observed by naked eye or digital quantification analysis.

In any one of the previous embodiments, the volume ratio of the mammalian blood sample to the multiphase system is about 0.15-4:1, 0.2-2:1, or 0.3-1:1.

In any one of the previous embodiments, during migration the reticulocytes contact one or more of the two or three phases sequentially.

In any one of the previous embodiments, the mammalian blood sample is a human blood sample.

In yet another aspect, a kit for the diagnosis of sickle cell disease using a multi-phase system is described, comprising:
  a) at least a first and second phase components each comprising at least one polymer; and
  b) instructions for:
    (i) combining the first and second phase components and water, each in a predetermined amount, to create a multi-phase system described herein, wherein multiple phases comprises an interface between the first and second phases; and
    (ii) adding a mammalian blood sample to the multi-phase system to allow the erythrocytes to migrate to a location(s) characteristic of their densities; and
    (iii) observing the presence or absence of erythrocytes below the second phase;
wherein the presence of erythrocytes below the second phase indicates sickle cell disease.

In yet another aspect, a kit for the diagnosis of subtypes of sickle cell disease is described, comprising:
  a) at least a first, second, and third phase components each comprising at least one polymer; and
  b) instructions for:
    (i) combining the first, second, and third phase components and water, each in a predetermined amount, to create a multi-phase system of described herein, wherein the multiple phases comprise interfaces between the first and third phases and between the third and second phases; and
    (ii) adding a mammalian blood sample to the multi-phase system to allow the erythrocytes to migrate to a location(s) characteristic of their densities;
    (iii) observing the presence or absence of erythrocytes at the interfaces;
wherein
  the presence of erythrocyte below the second phase indicates sickle cell disease;
  the pattern that the amount of erythrocytes present at the interface of the first and third phases is more than the amount of erythrocytes present at the interface of the third and second phases indicates homozygous sickle cell disease (Hb SS); and
  the pattern that the amount of erythrocytes present at the interface of the third and second phases is about the same or more than the amount of erythrocytes present at the interface of the first and third phases indicates hemoglobin sickle cell disease (Hb SC).

In any one of the preceding embodiments, the mammalian blood sample is a human blood sample.

DESCRIPTION OF THE DRAWINGS

The invention is described with reference to the following figures, which are presented for the purpose of illustration only and are not intended to be limiting. In the Drawings:

FIG. 4C shows a fluorescence image of the tube in FIG. 5B after illumination with longwave UV light.

FIGS. 20A-20B show two designs to load blood samples into a capillary that has been preloaded with SCD-AMPS-3 and sealed. In the "tube-in-tube" method (FIG. 20A), a small capillary with a ring of epoxy around it fills with blood by capillary action. This small tube can then be loaded into the larger capillary. In the "hole-in-tube" method (FIG. 20B), a small hole allows blood to wick into the prefilled tube.

FIGS. 23A-23D show examples of white pellet found at the bottom of some of the samples from Hb AA subjects. A tube-in-tube version of the SCD-AMPS-3 test is negative for SCD (FIG. 23A). Although the bottom is not red, there is a substantial gray layer above the white clay seal (dark gray in transmission imaging) (B/S) (D). Micrographs (FIG. 23B and FIG. 23C) reveal a large number of platelets and cell aggregates.

FIG. 35 shows the sealing step in the prototype development of an AMPS for sickle cell diagnosis.

FIG. 36 shows the quality control step in the prototype development of an AMPS for sickle cell diagnosis.

DETAILED DESCRIPTION

Figure 1:
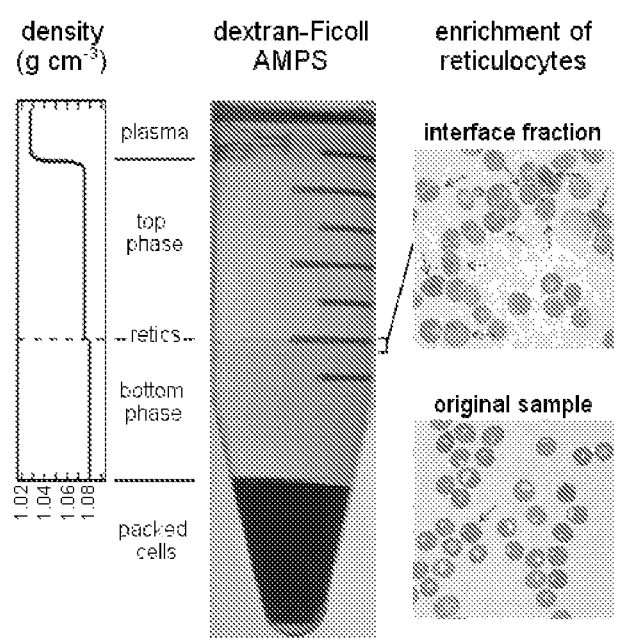
FIG. 1 illustrates a hypertonic ($\phi$=330 mOsm kg$^{-1}$) AMPS of 11.6% (w/v) dextran and 11.6% (w/v) Ficoll ($\rho_{top}$=1.086 g cm$^{-3}$ and $\rho_{bottom}$=1.089 g cm$^{-3}$) provides a step-gradient in density capable of enriching reticulocytes from blood.

Described herein are multi-phase systems including two or more phase-separated phases each containing a phase component. The MPS can be a two- or three-phase system as disclosed herein. However, MPSs containing more than three phases are also contemplated. The MPSs described herein have important biological applications, including, but not limited to, enrichment of reticulocytes, diagnosis of iron deficiency anemia and β-thalessemia trait, and diagnosis of sickle cell disease and its subtypes.

In some embodiments, MPSs as described herein are used to separate analytes (e.g., red blood cells, reticulocytes, erythrocytes, etc.) from each other or from impurities and other objects in the sample. The analytes migrate to phases characteristic of their densities, and in so doing, contact each phase of the multi-phase system sequentially. As used herein, "sequential contact" means that the analyte contacts and interacts with only one phase (and its phase component) at a time except at the interface between two phases. That is, the interaction of the analyte with the MPS occurs when the MPS has already phase separated and not during the process of phase separation. In some embodiments, the pH, osmolality, and the polymer used in the preparation of the phases separated components are selected to be compatible with the cells to be analyzed or separated.

The concept of the multi-phase system (MPS) is further explained herein. When two or more solutions each containing a phase component are mixed, the resulting system is not homogeneous; rather, two or more discrete phases, or layers, form. These layers are ordered according to density and arise from the exhibited limited interaction of the phase components with one another. The two or more phases or solutions thus exhibit limited interaction and form distinct phase boundaries between adjacent phases. Each phase can be aqueous or non-aqueous. The non-aqueous phase comprises an organic liquid or an organic solvent. When the solvent used for the MPS is water, the MPS is also called an aqueous multi-phase system (AMPS).

The multi-phase systems disclosed herein comprise two or more zones or regions that are phase-separated from each other, wherein each of the two or more phases comprises a phase component. The phase component is a polymer or a combination of two or more polymers.

Non-limiting examples of polymer used in the formation of a phase include dextran, polysucrose (herein referred to by the trade name "Ficoll"), poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propane-sulfonic acid), dextran sulfate, diethylaminoethyl-dextran, chondroitin sulfate A, poly(2-vinylpyridine-N-oxide), poly (diallyldimethyl ammonium chloride), poly(styrene sulfonic acid), polyallylamine, alginic acid, nonylphenol polyoxyethylene, poly(bisphenol A carbonate), polydimethylsiloxane, polystyrene, poly(4-vinylpyridine), polycaprolactone, polysulfone, poly(methyl methacrylate-co-methacrylic acid), poly(methyl methacrylate), poly(tetrahydrofuran), poly(propylene glycol), poly(vinyl acetate), copolymer, terpolymer, block copolymer, random polymer, linear polymer, branched polymer, crosslinked polymer, and dendrimer system thereof. As used herein, a polymer includes its homopolymer, copolymer, terpolymer, block copolymer, random polymer, linear polymer, branched polymer, crosslinked polymer, and/or dendrimer system.

The phase components are selected so that the resulting phases are phase-separated from each other. As used herein, phase-separation refers to the phenomena where two or more solutions, each comprising a phase component, when mixed together, form the same number of distinct phases where each phase has clear boundaries and is separated from other phases. Each phase component used in the solution is selected to be soluble in the solvent of the phase, so that each resulting phase is a distinct solution of the phase component and each phase is phase-separated from other adjacent phase(s). When the multi-phase polymer system is designed, each phase component is selected to predominantly reside in one particular phase of the multi-phase system. It should be noted that in the resulting multi-phase system, every phase can contain varying amounts of other phase components from other phases in the MPS, in addition to the selected desired phase component in that phase. Unless otherwise specified, the phase component composition in each phase of the multi-phase system recited herein generally refers to the starting phase component composition of each phase, or to the predominant phase component composition of each phase. The boundary between every two adjacent phases is also called the interface between the two phases. In some embodiments, the MPS is placed in a container and there is also an interface formed between the bottom phase and the container.

In some embodiments, the MPS described herein to analyze the biological analyte is a two-phase aqueous system. Non-limiting examples of the two phase systems include aqueous two-phase systems where the phase component combination of the two phases is selected from the group consisting of:

| | Phase component combinations | |
|---|---|---|
| 1 | poly(2-ethyl-2-oxazoline) | poly(methacrylic acid) |
| 2 | poly(2-ethyl-2-oxazoline) | poly(vinyl alcohol) |
| 3 | poly(ethylene glycol) | poly(methacrylic acid) |
| 6 | poly(ethylene glycol) | poly(2-ethyl-2-oxazoline) |
| 8 | dextran | poly(2-ethyl-2-oxazoline) |
| 10 | Ficoll | poly(methacrylic acid) |
| 11 | Ficoll | poly(vinyl alcohol) |
| 12 | Ficoll | poly(2-ethyl-2-oxazoline) |
| 15 | polyacrylamide | poly(methacrylic acid) |
| 16 | polyacrylamide | poly(acrylic acid) |
| 18 | polyacrylamide | poly(2-ethyl-2-oxazoline) |
| 19 | polyacrylamide | poly(ethylene glycol) |
| 20 | poly(diallyldimethyl ammonium chloride) | poly(methacrylic acid) |
| 21 | poly(diallyldimethyl ammonium chloride) | poly(acrylic acid) |
| 22 | poly(diallyldimethyl ammonium chloride) | poly(vinyl alcohol) |
| 23 | poly(diallyldimethyl ammonium chloride) | poly(2-ethyl-2-oxazoline) |
| 24 | poly(diallyldimethyl ammonium chloride) | poly(ethylene glycol) |
| 25 | dextran sulfate | poly(vinyl alcohol) |
| 26 | dextran sulfate | poly(2-ethyl-2-oxazoline) |
| 28 | chondroitin sulfate A | poly(methacrylic acid) |
| 29 | chondroitin sulfate A | poly(vinyl alcohol) |
| 30 | chondroitin sulfate A | poly(2-ethyl-2-oxazoline) |

-continued

| | Phase component combinations | |
|---|---|---|
| 31 | polyethyleneimine | poly(methacrylic acid) |
| 32 | polyethyleneimine | poly(2-ethyl-2-oxazoline) |
| 33 | polyethyleneimine | poly(ethylene glycol) |
| 34 | polyethyleneimine | Ficoll |
| 35 | polyethyleneimine | polyacrylamide |
| 36 | polyvinylpyrrolidone | poly(methacrylic acid) |
| 39 | poly(propylene glycol) | poly(methacrylic acid) |
| 41 | poly(propylene glycol) | polyacrylamide |
| 42 | poly(2-acrylamido-2-methyl-1-propanesulfonic acid) | dextran |
| 43 | poly(2-acrylamido-2-methyl-1-propanesulfonic acid) | polyvinylpyrrolidone |
| 44 | poly(styrene sulfonic acid) | poly(2-ethyl-2-oxazoline) |
| 45 | poly(styrene sulfonic acid) | dextran sulfate |
| 46 | diethylaminoethyl-dextran | poly(acrylic acid) |
| 47 | polyallylamine | dextran sulfate |
| 48 | alginic acid | poly(acrylic acid) |
| 49 | alginic acid | poly(propylene glycol) |
| 50 | (hydroxypropyl)methyl cellulose | poly(diallyldimethyl ammonium chloride |
| 51 | (hydroxypropyl)methyl cellulose | poly(propylene glycol) |
| 52 | carboxy-polyacrylamide | poly(methacrylic acid) |
| 53 | carboxy-polyacrylamide | poly(vinyl alcohol) |
| 54 | carboxy-polyacrylamide | polyethyleneimine |
| 55 | hydroxyethyl cellulose | dextran |
| 56 | hydroxyethyl cellulose | Ficoll |
| 57 | methyl cellulose | Ficoll |
| 58 | Zonyl | poly(methacrylic acid) |
| 59 | Zonyl | dextran |
| 60 | Zonyl | polyacrylamide |
| 61 | Brij | poly(2-ethyl-2-oxazoline) |
| 62 | Brij | Ficoll |
| 63 | Brij | polyallylamine |
| 64 | Tween | poly(methacrylic acid) |
| 65 | Tween | poly(vinyl alcohol) |
| 66 | Tween | poly(2-ethyl-2-oxazoline) |
| 69 | Tween | Ficoll |
| 70 | Tween | polyacrylamide |
| 71 | Tween | polyallylamine |
| 72 | Tween | hydroxyethyl cellulose |
| 73 | Triton | poly(methacrylic acid) |
| 74 | Triton | poly(acrylic acid) |
| 75 | Triton | poly(2-ethyl-2-oxazoline) |
| 77 | Triton | Ficoll |
| 78 | Triton | polyacrylamide |
| 79 | Triton | polyallylamine |
| 81 | nonylphenol polyoxyethylene | poly(methacrylic acid) |
| 82 | nonylphenol polyoxyethylene | dextran |
| 83 | 1-O-Octyl-B-D-glucopyranoside | poly(methacrylic acid) |
| 84 | 1-O-Octyl-B-D-glucopyranoside | poly(2-ethyl-2-oxazoline) |
| 86 | 1-O-Octyl-B-D-glucopyranoside | polyethyleneimine |
| 87 | Pluronic | poly(methacrylic acid) |
| 88 | Pluronic | poly(vinyl alcohol) |
| 89 | Pluroni | poly(2-ethyl-2-oxazoline) |
| 90 | Pluronic | dextran |
| 91 | Pluronic | Ficoll |
| 92 | Pluronic | polyacrylamide |
| 93 | Pluronic | polyethyleneimine |
| 94 | sodium dodecyl sulfate | poly(acrylic acid) |
| 95 | sodium cholate | poly(methacrylic acid) |
| 96 | sodium cholate | dextran sulfate |
| 97 | N,N-dimethyldodecylamine N-oxide | poly(methacrylic acid) |
| 98 | N,N-dimethyldodecylamine N-oxide | polyacrylamide |
| 99 | CHAPS | poly(methacrylic acid) |
| 100 | CHAPS | poly(2-ethyl-2-oxazoline) |
| 101 | CHAPS | poly(ethylene glycol) |
| 102 | CHAPS | dextran |
| 103 | CHAPS | Ficoll |
| 104 | CHAPS | polyacrylamide |
| 105 | CHAPS | polyethyleneimine |
| 106 | CHAPS | Pluronic |
| 107 | PVPNO | PA |
| 108 | PVPNO | PMAA |
| 111 | PVPNO | PEOZ |
| 112 | PVPNO | PEG |
| 116 | PVPNO | PEI |
| 117 | PVPNO | Tween |
| 118 | Ficoll | Detran |
| 119 | Poly(ethylene glycol) | Ficoll |

In some embodiments, the MPS described herein to analyze the biological analyte is a three-phase aqueous system. Non-limiting examples of the three phase systems include aqueous three-phase systems where wherein the phase component combination of the three phases is selected from the group consisting of:

| Number | Phase component combinations | | |
|---|---|---|---|
| 1 | poly(methacrylic acid) | poly(2-ethyl-2-oxazoline) | poly(ethylene glycol) |
| 2 | poly(methacrylic acid) | poly(2-ethyl-2-oxazoline) | Ficoll |
| 3 | poly(methacrylic acid) | poly(2-ethyl-2-oxazoline) | polyacrylamide |
| 4 | poly(methacrylic acid) | poly(2-ethyl-2-oxazoline) | poly(diallyldimethyl ammonium chloride |
| 5 | poly(methacrylic acid) | poly(2-ethyl-2-oxazoline) | chondroitin sulfate A |
| 6 | poly(methacrylic acid) | poly(2-ethyl-2-oxazoline) | polyethyleneimine |
| 7 | poly(methacrylic acid) | poly(2-ethyl-2-oxazoline) | Tween |
| 8 | poly(methacrylic acid) | poly(2-ethyl-2-oxazoline) | Triton |
| 9 | poly(methacrylic acid) | poly(2-ethyl-2-oxazoline) | 1-O-Octyl-B-D-glucopyranoside |
| 10 | poly(methacrylic acid) | poly(2-ethyl-2-oxazoline) | Pluronic |
| 11 | poly(methacrylic acid) | poly(2-ethyl-2-oxazoline) | CHAPS |
| 12 | poly(methacrylic acid) | poly(ethylene glycol) | Ficoll |
| 13 | poly(methacrylic acid) | poly(ethylene glycol) | polyacrylamide |
| 14 | poly(methacrylic acid) | poly(ethylene glycol) | poly(diallyldimethyl ammonium chloride |
| 15 | poly(methacrylic acid) | poly(ethylene glycol) | polyethyleneimine |
| 16 | poly(methacrylic acid) | poly(ethylene glycol) | polyvinylpyrrolidone |
| 17 | poly(methacrylic acid) | poly(ethylene glycol) | Tween 20 |
| 18 | poly(methacrylic acid) | poly(ethylene glycol) | 1-O-Octyl-B-D-glucopyranoside |
| 19 | poly(methacrylic acid) | poly(ethylene glycol) | CHAPS |
| 20 | poly(methacrylic acid) | Ficoll | polyethyleneimine |
| 21 | poly(methacrylic acid) | Ficoll | Tween |
| 22 | poly(methacrylic acid) | Ficoll | Triton |
| 23 | poly(methacrylic acid) | Ficoll | Pluronic |
| 24 | poly(methacrylic acid) | Ficoll | CHAPS |
| 25 | poly(methacrylic acid) | polyacrylamide | polyethyleneimine |
| 26 | poly(methacrylic acid) | polyacrylamide | poly(propylene glycol) |
| 27 | poly(methacrylic acid) | polyacrylamide | Zonyl |
| 28 | poly(methacrylic acid) | polyacrylamide | Tween |
| 29 | poly(methacrylic acid) | polyacrylamide | Triton |
| 30 | poly(methacrylic acid) | polyacrylamide | Pluronic |
| 31 | poly(methacrylic acid) | polyacrylamide | N,N-dimethyldodecylamine N-oxide |
| 32 | poly(methacrylic acid) | polyacrylamide | CHAPS |
| 33 | poly(methacrylic acid) | polyethyleneimine | carboxy-polyacrylamide |
| 34 | poly(methacrylic acid) | polyethyleneimine | 1-O-Octyl-B-D-glucopyranoside |
| 35 | poly(methacrylic acid) | polyethyleneimine | Pluronic |
| 36 | poly(methacrylic acid) | polyethyleneimine | CHAPS |
| 37 | poly(methacrylic acid) | Pluronic F68 | CHAPS |
| 38 | poly(acrylic acid) | poly(ethylene glycol) | polyacrylamide |
| 39 | poly(acrylic acid) | poly(ethylene glycol) | poly(diallyldimethyl ammonium chloride |
| 40 | poly(acrylic acid) | polyacrylamide | Triton |
| 41 | poly(vinyl alcohol) | poly(2-ethyl-2-oxazoline) | poly(ethylene glycol) |
| 42 | poly(vinyl alcohol) | poly(2-ethyl-2-oxazoline) | dextran |
| 43 | poly(vinyl alcohol) | poly(2-ethyl-2-oxazoline) | Ficoll |
| 44 | poly(vinyl alcohol) | poly(2-ethyl-2-oxazoline) | polyacrylamide |
| 45 | poly(vinyl alcohol) | poly(2-ethyl-2-oxazoline) | poly(diallyldimethyl ammonium chloride |
| 46 | poly(vinyl alcohol) | poly(2-ethyl-2-oxazoline) | dextran sulfate |
| 47 | poly(vinyl alcohol) | poly(2-ethyl-2-oxazoline) | chondroitin sulfate A |
| 48 | poly(vinyl alcohol) | poly(2-ethyl-2-oxazoline) | Tween |
| 49 | poly(vinyl alcohol) | poly(2-ethyl-2-oxazoline) | Pluronic |
| 50 | poly(vinyl alcohol) | poly(ethylene glycol) | dextran |
| 51 | poly(vinyl alcohol) | poly(ethylene glycol) | Ficoll |
| 52 | poly(vinyl alcohol) | poly(ethylene glycol) | polyacrylamide |
| 53 | poly(vinyl alcohol) | poly(ethylene glycol) | poly(diallyldimethyl ammonium chloride |
| 54 | poly(vinyl alcohol) | poly(ethylene glycol) | dextran sulfate |
| 55 | poly(vinyl alcohol) | poly(ethylene glycol) | Tween |
| 56 | poly(vinyl alcohol) | dextran | Ficoll |
| 57 | poly(vinyl alcohol) | dextran | Tween |
| 58 | poly(vinyl alcohol) | dextran | Pluronic |
| 59 | poly(vinyl alcohol) | Ficoll | Tween |
| 60 | poly(vinyl alcohol) | Ficoll | Pluronic |
| 61 | poly(vinyl alcohol) | polyacrylamide | Tween |
| 62 | poly(vinyl alcohol) | polyacrylamide | Pluronic |
| 63 | poly(2-ethyl-2-oxazoline) | poly(ethylene glycol) | dextran |
| 64 | poly(2-ethyl-2-oxazoline) | poly(ethylene glycol) | Ficoll |
| 65 | poly(2-ethyl-2-oxazoline) | poly(ethylene glycol) | polyacrylamide |
| 66 | poly(2-ethyl-2-oxazoline) | poly(ethylene glycol) | poly(diallyldimethyl ammonium chloride |
| 67 | poly(2-ethyl-2-oxazoline) | poly(ethylene glycol) | dextran sulfate |
| 68 | poly(2-ethyl-2-oxazoline) | poly(ethylene glycol) | polyethyleneimine |
| 69 | poly(2-ethyl-2-oxazoline) | poly(ethylene glycol) | Tween |
| 70 | poly(2-ethyl-2-oxazoline) | poly(ethylene glycol) | 1-O-Octyl-B-D-glucopyranoside |
| 71 | poly(2-ethyl-2-oxazoline) | poly(ethylene glycol) | CHAPS |
| 72 | poly(2-ethyl-2-oxazoline) | dextran | Ficoll |
| 73 | poly(2-ethyl-2-oxazoline) | dextran | Tween |
| 74 | poly(2-ethyl-2-oxazoline) | dextran | Triton |

-continued

| Number | Phase component combinations | | |
|---|---|---|---|
| 75 | poly(2-ethyl-2-oxazoline) | dextran | Pluronic |
| 76 | poly(2-ethyl-2-oxazoline) | dextran | CHAPS |
| 77 | poly(2-ethyl-2-oxazoline) | Ficoll | polyethyleneimine |
| 78 | poly(2-ethyl-2-oxazoline) | Ficoll | Brij |
| 79 | poly(2-ethyl-2-oxazoline) | Ficoll | Tween |
| 80 | poly(2-ethyl-2-oxazoline) | Ficoll | Triton |
| 81 | poly(2-ethyl-2-oxazoline) | Ficoll | Pluronic |
| 82 | poly(2-ethyl-2-oxazoline) | Ficoll | CHAPS |
| 83 | poly(2-ethyl-2-oxazoline) | polyacrylamide | polyethyleneimine |
| 84 | poly(2-ethyl-2-oxazoline) | polyacrylamide | Tween |
| 85 | poly(2-ethyl-2-oxazoline) | polyacrylamide | Triton |
| 86 | poly(2-ethyl-2-oxazoline) | polyacrylamide | Pluronic |
| 87 | poly(2-ethyl-2-oxazoline) | polyacrylamide | CHAPS |
| 88 | poly(2-ethyl-2-oxazoline) | dextran sulfate | poly(styrene sulfonic acid) |
| 89 | poly(2-ethyl-2-oxazoline) | polyethyleneimine | 1-O-Octyl-B-D-glucopyranoside |
| 90 | poly(2-ethyl-2-oxazoline) | polyethyleneimine | Pluronic |
| 91 | poly(2-ethyl-2-oxazoline) | polyethyleneimine | CHAPS |
| 92 | poly(2-ethyl-2-oxazoline) | Pluronic F68 | CHAPS |
| 93 | poly(ethylene glycol) | dextran | Ficoll |
| 94 | poly(ethylene glycol) | dextran | polyvinylpyrrolidone |
| 95 | poly(ethylene glycol) | dextran | Tween |
| 96 | poly(ethylene glycol) | dextran | CHAPS |
| 97 | poly(ethylene glycol) | Ficoll | polyethyleneimine |
| 98 | poly(ethylene glycol) | Ficoll | Tween |
| 99 | poly(ethylene glycol) | Ficoll | CHAPS |
| 100 | poly(ethylene glycol) | polyacrylamide | polyethyleneimine |
| 101 | poly(ethylene glycol) | polyacrylamide | Tween |
| 102 | poly(ethylene glycol) | polyacrylamide | CHAPS |
| 103 | poly(ethylene glycol) | polyethyleneimine | 1-O-Octyl-B-D-glucopyranoside |
| 104 | poly(ethylene glycol) | polyethyleneimine | CHAPS |
| 105 | dextran | Ficoll | hydroxyethyl cellulose |
| 106 | dextran | Ficoll | Tween |
| 107 | dextran | Ficoll | Triton |
| 108 | dextran | Ficoll | Pluronic |
| 109 | dextran | Ficoll | CHAPS |
| 110 | dextran | polyvinylpyrrolidone | poly(2-acrylamido-2-methyl-1-propanesulfonic acid) |
| 111 | dextran | hydroxyethyl cellulose | Tween |
| 112 | dextran | hydroxyethyl cellulose | Triton |
| 113 | dextran | Pluronic F68 | CHAPS |
| 114 | Ficoll | polyethyleneimine | Pluronic |
| 115 | Ficoll | polyethyleneimine | CHAPS |
| 116 | Ficoll | hydroxyethyl cellulose | Tween |
| 117 | Ficoll | hydroxyethyl cellulose | Triton |
| 118 | Ficoll | Pluronic F68 | CHAPS |
| 119 | polyacrylamide | polyethyleneimine | Pluronic |
| 120 | polyacrylamide | polyethyleneimine | CHAPS |
| 121 | polyacrylamide | Pluronic F68 | CHAPS |
| 122 | polyethyleneimine | Pluronic F68 | CHAPS |
| 123 | PEOZ | PEG | PVPNO |
| 124 | PEOZ | PEI | PVPNO |
| 125 | PEOZ | PA | PVPNO |
| 126 | PEOZ | PMAA | PVPNO |
| 127 | PEG | PEI | PVPNO |
| 128 | PEG | PMAA | PVPNO |
| 129 | PEG | PA | PVPNO |
| 130 | PEI | PA | PVPNO |
| 131 | PEI | PMAA | PVPNO |
| 132 | PA | PMAA | PVPNO |
| 133 | PEOZ | PEG | PVPNO |
| 134 | PEOZ | TWEEN | PVPNO |
| 135 | PEOZ | PA | PVPNO |
| 136 | PEOZ | PMAA | PVPNO |
| 137 | PEG | TWEEN | PVPNO |
| 138 | TWEEN | PA | PVPNO |
| 139 | TWEEN | PMAA | PVPNO |
| 140 | PA | PMAA | PVPNO |
| 141 | PEG | PA | PVPNO |
| 142 | PEG | PMAA | PVPNO |

A list of some of the abbreviations for polymer used in this study are as follows:
poly(2-vinylpyridine-N-oxide)—PVPNO;
poly(methacrylic acid)—PMAA;
poly(acrylic acid)—PAA;
polyacrylamide—PA;
poly(vinyl alcohol)—PVA;
poly(2-ethyl-2-oxazoline)—PEOZ;
poly(ethylene glycol)—PEG;
hydroxyethylcelluolose—HEC;
polyethyleneimine—PEI; and
polyvinylpyrrolidone—PVP.

Further details and examples of the multi-phase systems can be found in WO2012/024688, filed on Aug. 22, 2011, WO2012/024693, filed on Aug. 22, 2011, WO2012/024690, filed on Aug. 22, 2011, and WO2012/024691, filed on Aug. 22, 2011, all of which are hereby incorporated by reference herein in their entirety.

Section 1. Enrichment of Reticulocytes from Whole Blood Using Multi-Phase Systems

*Plasmodium* (*P.*) *vivax*, *P. ovale*, and *P. knowlesi*—three causative agents of malaria in humans—preferentially invade human reticulocytes. The study of these species of malaria suffers from the practical difficulty of in vitro cultures in whole human blood. Their cultivation in blood enriched for reticulocytes would provide concentrated host cells in which the parasites proliferate; continuous cultures of these parasites would make their study much more practical. Enrichment is difficult because reticulocytes exist at a low concentration (0.5-2.5% of erythrocytes) in whole blood, have a short half-life in culture (~30 hours), and cannot be stored without terminal differentiation into mature erythrocytes.

Current methods to obtain substantially enriched (>15% of erythrocytes) samples of reticulocytes are impractical, expensive, labor-intensive, and not satisfactory for routine use. They also do not generate a sufficiently high yield of reticulocytes from normal blood to support continuous culture of malaria parasites that grow in reticulocytes. These methods include culture and development of progenitors, differential centrifugation, centrifugation over layered gradients, and affinity-based separation.

Density provides a label-free characteristic to use in enriching reticulocytes. The average density of reticulocytes is slightly lower than that of mature erythrocytes ($\Delta\rho \approx 0.009$ g cm$^{-3}$). The reticulocyte population is concentrated in the least dense quarter of the distribution of densities of erythrocytes. In some embodiments, the process of enriching reticulocytes as described herein is used for mammalian blood. In some specific embodiments, the mammal is human.

Described herein is the enrichment of a reticulocytes using aqueous multiphase systems (AMPS). According to one or more embodiments, whole blood is centrifuged through an aqueous multiphase system (AMPS) having immiscible polymers solutions phases selected to have step-gradients in density that concentrate the reticulocytes at the interface between different phases of an AMPS. This concentration facilitates the extraction of blood enriched for reticulocytes. The degree of the reticulocyte enrichment can be measured by reticulocytemia. In some embodiments, an enhanced enrichment to a reticulocytemia of more than 60%, e.g., 64±3%, can be obtained. As used herein, reticulocytemia refers to the percentage of the total red blood cells in a sample that are identified as reticulocytes, either by microscopy or by flow cytometry after staining reticulin.

The lack of a reliable and efficient method to provide reticulocytes has impeded the research on pharmaceuticals for drug-resistance malaria and vaccinate development. MPSs may provide a variable way of enriching reticulocyte, but the choice of the MPSs requires many considerations. When blood is layered on top of an AMPS, the region between the top phase and the blood forms a boundary of density like those found in layered gradients. This boundary is diffused and unstable because plasma is soluble in the phases of AMPSs. Cells concentrated at the boundary, therefore, are not confined sharply, and the subsequent recovery of cells from the boundary region is more difficult than from a well-defined interface between two immiscible phases. The two phases of a two-phase AMPS provide two well-defined interfaces—one between the two phases of the AMPS, and one between the denser phase and the bottom of the container—in addition to the boundary that is formed with the blood. In this arrangement, one interface (that between the two liquid phases of the AMPS) collects the enriched reticulocytes, and one interface (that between the denser phase and the bottom of the tube) collects the remaining erythrocytes. A MPS with more than two phases could also be used to enrich a blood same in reticulocytes.

Applicants have surprisingly found that the selected ranges of the phase densities and tonicities described herein result in superior purity and yield of reticulocytes, compared with other known methods. Varying the osmolality and density of the phases of AMPS provides different levels of enrichment and yield of reticulocytes. Exemplary MPSs with different tonicities that provide good yield and enrichment for reticulocytes are reported in Table 1.

Specifically, Applicants found that changes in osmolality may have different effects on reticulocytes and mature erythrocytes. General relationships between density and osmolality may be established (e.g., hypertonic environments increase the buoyant density of an erythrocyte), but the shift in the density that provides an enriched population of reticulcytes is not easily predictable because the populations of mature erythrocytes and reticulocytes may be affected differently. Applicants have identified densities ranges for each phase of the MPS that are suitable for the concentration of reticulocytes at the phase interface and then identified hypertonic, isotonic, and hypotonic conditions to achieve a local enhancement in enrichment of the reticulocytes.

In addition to reticulocytemia, the yield and scale for the separations are also reported herein. Yield and scale are among the characteristics of reticulocyte enrichment for the cultivation of malaria parasites. Systems that scale well to large volumes (>10 mL of blood) and attain >10 µL of packed reticulocytes decrease the burden of time and resources to maintain cultures of *P. knowlesi*, *P. vivax*, or *P. ovale*. Changing the volume ratio of blood to polymer affected the final enrichment of reticulocytes (FIGS. 4A-4B & 5A-5C). In some embodiments, a constant volume ratio of blood to polymer, however, achieves reproducible results at different scales (FIGS. 6A-6B).

In one aspect, an aqueous multi-phase system for enriching reticulocytes content in a biological sample is described, comprising two or more phase-separated phases comprising:

a first aqueous phase comprising a first phase component and having a first density between about 1.025 g/cm$^3$ and about 1.090 g/cm$^3$; and a second aqueous phase comprising a second phase component and having a second density between about 1.065 g/cm$^3$ and about 1.095 g/cm$^3$;

wherein the first density is lower than the second density; and each of the first and second phase components comprises at least one polymer.

The densities of the first and second phases are selected to enrich an erythrocyte component in reticulocytes. In some embodiments, the first density is about 1.050-1.089 g/cm$^3$, 1.050-1.085 g/cm$^3$, 1.050-1.080 g/cm$^3$, 1.050-1.075 g/cm$^3$, 1.050-1.070 g/cm$^3$, 1.050-1.065 g/cm$^3$, 1.050-1.060 g/cm$^3$, 1.060-1.089 g/cm$^3$, 1.060-1.085 g/cm$^3$, 1.060-1.080 g/cm$^3$, 1.060-1.075 g/cm$^3$, 1.060-1.070 g/cm$^3$, 1.060-1.065 g/cm$^3$, 1.065-1.089 g/cm$^3$, 1.065-1.085 g/cm$^3$, 1.065-1.080 g/cm$^3$, 1.065-1.075 g/cm$^3$, or 1.065-1.070 g/cm$^3$. In some specific embodiments, the first density is about 1.067, 1.068, 1.071, 1.074, 1.075, 1.076, 1.078, 1.079, 1.080, 1.081, 1.082, 1.083, 1.084, 1.085, 1.086, 1.087, 1.088, or 1.089 g/cm$^3$. In some specific embodiments, the first density is about 1.060-1.070 g/cm$^3$, 1.070-1.080 g/cm$^3$, or 1.080-1.090 g/cm$^3$.

The density of the second phase is higher than that of the first phase. In some embodiments, the second density is about 1.065-1.090 g/cm$^3$, 1.065-1.085 g/cm$^3$, 1.065-1.080 g/cm$^3$, 1.065-1.075 g/cm$^3$, 1.065-1.070 g/cm$^3$, 1.070-1.085 g/cm$^3$, 1.070-1.080 g/cm$^3$, 1.070-1.075 g/cm$^3$, 1.080-1.090 g/cm$^3$, 1.080-1.085 g/cm$^3$, or 1.075-1.080 g/cm$^3$. In some specific embodiments, the second density is about 1.071, 1.072, 1.073, 1.074, 1.075, 1.076, 1.077, 1.078, 1.079, 1.080, 1.081, 1.082, 1.083, 1.084, 1.085, 1.086, 1.087, 1.088, 1.089, 1.090, 1.091, or 1.092 g/cm$^3$. In some embodiments, the second density is about 1.070-1.080 g/cm$^3$, 1.080-1.090 g/cm$^3$, or 1.090-1.095 g/cm$^3$.

In some specific embodiments, the first and second densities are about 1.068 g/cm$^3$ and 1.072 g/cm$^3$, 1.082 g/cm$^3$ and 1.085 g/cm$^3$, 1.080 g/cm$^3$ and 1.083 g/cm$^3$, 1.076 g/cm$^3$ and 1.080 g/cm$^3$, 1.071 g/cm$^3$ and 1.075 g/cm$^3$, 1.067 g/cm$^3$ and 1.071 g/cm$^3$, 1.086 g/cm$^3$ and 1.089 g/cm$^3$, 1.084 g/cm$^3$ and 1.088 g/cm$^3$, 1.081 g/cm$^3$ and 1.085 g/cm$^3$, 1.078 g/cm$^3$ and 1.082 g/cm$^3$, or 1.075 g/cm$^3$ and 1.079 g/cm$^3$, respectively. In some specific embodiments, the first and second densities are about 1.067-1.086 g/cm$^3$ and 1.070-1.089 g/cm$^3$, respectively.

In some embodiments, the first density is less than that of the reticulocytes but higher than the blood plasma. Additionally, the second density is greater than that of the reticulocytes. However, the actual density of a reticulocytes may vary due to other factors, e.g., tonicity. Applicants have surprisingly found that the combinations of the first and second densities as described herein or the ranges of the first and second densities as described herein resulting in enhanced yield and reticulocytemia. For instance, the MPSs as described herein result in reticulocytes as collected having a reticulocytemia of about more than 10%, 20%, 30%, 40%, 50%, 60%, or 70%, or in the range of 10-70% or 20-60% or 40-60%. Reticulocytemia ranges bounded by any of the specific values noted above are also contemplated. In some embodiments, the reticulocytes are collected with a yield of more than 0.5%, 1%, 1.5%, 2%, 3%, 4%, 5%, 10%, or 20%, or in the range of 0.5-20%, or 1-10% or 2-5%. Yield ranges bounded by any of the specific values noted above are also contemplated. The yield is calculated by the following method: first the reticulocytemia on the original blood sample (RETinit %) is measured. The method then estimates the total RBCs in the original blood added (RBCinit) by either cytometry, or by hematocrit (packed cell volume*10^7 cells/microliter). The method then measures the final reticulocytemia (RETfin %) and final volume (RBCfin). The yield is calculated as (RETfin %*RBCfin)/(RETinit %*RBCinit).

Additionally, in blood, the physiological reference range for pH is 7.38-7.44, and for osmolality is 285-295 mOsm kg$^{-1}$. Changes to either of these parameters will result in changes to the morphology and density of blood cells. Applicants have found that differences between ion transport in reticulocytes and mature erythrocytes enhance differences in density due to unequal responses to osmotic stress. Therefore, osmolality provides an additional parameter to tune the separation of these cells based on density.

Applicants have also surprisingly found that the tonicity of the MPS can affect the yield and enrichment result of the reticulocyte. In some embodiments, the multi-phase system is hypertonic, isotonic, or hypotonic. In some specific embodiments, the multi-phase system is hypertonic, which may enhance enrichment results and yield compared with isotonic or hypotonic systems. In some specific embodiments, the multi-phase system has a tonicity of about 320-340, 320-330, 330-340, 325, 326, 327, 328, 329, 330, 331, 332, 335, 336, or 340 mOsm/kg. Ranges bounded by any of the specific values noted above are also contemplated. Without wishing to be bound by any particular theory, it is believed that because reticulocytes and mature erythrocytes are affected by tonicity differently, the difference in density between the reticulocytes and mature erythrocyte populations may be increased or described by changing tonicity. This effect could either increase or decrease both yield and purity of the reticulocytes enrichment.

In some embodiments, the MPS used herein for the enrichment of the reticulocytes is a two-phase system. The phase component for each phase is selected so that the MPS as a whole will phase-separate. In some embodiments, the combination of the first and second phase components is selected from the group consisting of:

| | Phase component combinations | |
|---|---|---|
| 1 | poly(2-ethyl-2-oxazoline) | poly(methacrylic acid) |
| 2 | poly(2-ethyl-2-oxazoline) | poly(vinyl alcohol) |
| 3 | poly(ethylene glycol) | poly(methacrylic acid) |
| 6 | poly(ethylene glycol) | poly(2-ethyl-2-oxazoline) |
| 8 | dextran | poly(2-ethyl-2-oxazoline) |
| 10 | Ficoll | poly(methacrylic acid) |
| 11 | Ficoll | poly(vinyl alcohol) |
| 12 | Ficoll | poly(2-ethyl-2-oxazoline) |
| 15 | polyacrylamide | poly(methacrylic acid) |
| 16 | polyacrylamide | poly(acrylic acid) |
| 18 | polyacrylamide | poly(2-ethyl-2-oxazoline) |
| 19 | polyacrylamide | poly(ethylene glycol) |
| 20 | poly(diallyldimethyl ammonium chloride | poly(methacrylic acid) |
| 21 | poly(diallyldimethyl ammonium chloride | poly(acrylic acid) |
| 22 | poly(diallyldimethyl ammonium chloride | poly(vinyl alcohol) |
| 23 | poly(diallyldimethyl ammonium chloride | poly(2-ethyl-2-oxazoline) |
| 24 | poly(diallyldimethyl ammonium chloride | poly(ethylene glycol) |
| 25 | dextran sulfate | poly(vinyl alcohol) |
| 26 | dextran sulfate | poly(2-ethyl-2-oxazoline) |
| 31 | polyethyleneimine | poly(methacrylic acid) |
| 32 | polyethyleneimine | poly(2-ethyl-2-oxazoline) |
| 33 | polyethyleneimine | poly(ethylene glycol) |
| 34 | polyethyleneimine | Ficoll |
| 35 | polyethyleneimine | polyacrylamide |
| 36 | polyvinylpyrrolidone | poly(methacrylic acid) |

-continued

| Phase component combinations | |
|---|---|
| 39 poly(propylene glycol) | poly(methacrylic acid) |
| 41 poly(propylene glycol) | polyacrylamide |
| 42 poly(2-acrylamido-2-methyl-1-propanesulfonic acid) | dextran |
| 43 poly(2-acrylamido-2-methyl-1-propanesulfonic acid) | polyvinylpyrrolidone |
| 44 poly(styrene sulfonic acid) | poly(2-ethyl-2-oxazoline) |
| 45 poly(styrene sulfonic acid) | dextran sulfate |
| 46 diethylaminoethyl-dextran | poly(acrylic acid) |
| 47 polyallylamine | dextran sulfate |
| 50 (hydroxypropyl)methyl cellulose | poly(diallyldimethyl ammonium chloride |
| 51 (hydroxypropyl)methyl cellulose | poly(propylene glycol) |
| 52 carboxy-polyacrylamide | poly(methacrylic acid) |
| 53 carboxy-polyacrylamide | poly(vinyl alcohol) |
| 54 carboxy-polyacrylamide | polyethyleneimine |
| 55 hydroxyethyl cellulose | dextran |
| 56 hydroxyethyl cellulose | Ficoll |
| 57 methyl cellulose | Ficoll |
| 81 nonylphenol polyoxyethylene | poly(methacrylic acid) |
| 82 nonylphenol polyoxyethylene | dextran |
| 107 PVPNO | PA |
| 108 PVPNO | PMAA |
| 111 PVPNO | PEOZ |
| 112 PVPNO | PEG |
| 116 PVPNO | PEI |
| 117 PVPNO | Tween |
| 118 Ficoll | Detran |
| 119 Poly(ethylene glycol) | Ficoll. |

The concentration of the phase component in each phase is selected so that the resulting density of each phase will fall in the range of density as described herein. In some embodiments, the concentration of the first phase component in the first phase or the concentration of the second phase component in the second phase is between about 1-40% (w/v). In some specific embodiments, the concentration of the first phase component in the first phase and the concentration of the second phase component in the second phase are each independently about 9.0%, 9.3%, 9.5%, 10.0%, 10.1%, 10.3%, 10.5%, 10.6%, 10.8%, 11.0%, 11.1%, 11.4%, 11.6%, or 12.0% (w/v). Ranges bounded by any of the specific values noted above are also contemplated. In some specific embodiments, the concentration of the first phase component in the first phase or the concentration of the second phase component in the second phase is about 9.0%-12.0% (w/v).

In some embodiments, the first and second phase components for the aqueous two-phase system for enrichment of reticulocytes are each selected from the group consisting of Caboxy-polyacrylamide, Dextran, Ficoll, N,N-dimethyldodecylamine N-oxide, poly(2-ethyl-2-oxazoline), poly(acrylic acid), poly(ethylene glycol), poly(methacrylic acid), poly(vinyl alcohol), polyacrylamide, polyethyleneimine, hydroxyethyl cellulose, poly(2-acrylamido-2-methyl-1-propanesulfonic acid), polyvinylpyrrolidone, Nonyl, polyallylamine, (hydroxypropyl)methyl cellulose, diethylaminoethyl-dextran, and nonylphenol polyoxyethylene 20.

In one specific embodiment, the aqueous two-phase system for enrichment of reticulocytes has dextran and Ficoll as its first and second phase components, respectively. In some embodiments, Ficoll having a molecular weight of 70 K Da or 400 Da is used. In some embodiments, dextran having a molecular weight of 500 K Da is used. In other embodiments, Ficoll or dextran with other molecular weight known in the art can be used.

In another aspect, a method for enriching reticulocytes content in a biological sample is described, comprising:

(a) providing an aqueous multi-phase system described herein, wherein the multi-phase system comprising at least two phases phase-separating to form an interface between first and second phases; and (b) adding a mammalian blood sample comprising reticulocytes to the multi-phase system to allow the reticulocytes to migrate to a location(s) in the multi-phase system characteristic of their density; and (c) collecting reticulocytes at the interface of the first and second aqueous phases.

In some embodiments, the densities of the first and second phases are selected so that the enriched reticulocytes will settle at the interface of the first and second phases. This will allow easy separation and collection of the enriched reticulocytes.

The differences in the densities of the phases of MPSs provide a means to perform density-based separations. The interfaces between phases mark discontinuities (on the molecular scale) between continuous fluid phases of different density. The densities ($\rho_A$ and $\rho_B$) of the phases above and below the interface establish the range of densities for components ($\rho_C$) that will localize at the interface ($\rho_A > \rho_C > \rho_B$). The interfacial surface energy between the phases of a MPS is astonishingly low (from nJ m$^{-2}$ to mJ m$^{-2}$); a low interfacial surface energy reduces the mechanical stress on cells as they pass through the interface.

Each phase of the MPS has an upper and a lower phase boundary, and two adjacent phases form a common interface in between. In most instances, there is not an exact match between the biological analyte's (e.g., reticulocyte's) density and the density of any particular phase. The analyte's density is between the densities of two adjacent phases in a MPS, and the analyte should therefore remain at the interface of the two adjacent phases. If the analyte should have the same density as that of one of the phases, the analyte will remain within the density-matched phase without contacting any boundary. In this case, the analyte resides within the phase due to a density match and not due to any favorable or preferential interaction of the analyte with one phase over another. In still other embodiments, the analyte may have a density less than that of the top phase of the MPS (the phase with the least density) and remain at the top of the MPS with a portion of the analyte above the upper boundary of the top phase after migration. In still other embodiments, the analyte may have a greater density than that of the bottom phase of the MPS (the phase with the most density) and remain at the bottom of the MPS after migration. At least one advantage of this system is that there is no need to match the density of the phase system with the target biological analytes, e.g., red blood cells, reticulocytes, or erythrocytes, (which can be challenging) in order to effect separation and/or local concentration enhancement of the target reticulocyte.

Compared to layered gradients in density (e.g., Percoll, Optiprep, or Nycodenz), the MPSs described herein offer several advantages: i) they are thermodynamically stable, ii) they self-assemble rapidly (t~15 minutes, 2000 g) on centrifugation or slowly (t~24 hours) on settling in a gravitational field, iii) they can differentiate remarkably small differences in density ($\Delta\rho<0.001$ g cm$^{-3}$), and iv) they provide well-defined interfaces that facilitate both the identification and extraction of sub-populations of cells by concentrating them to quasi-two-dimensional surfaces.

In some embodiments, Applicants have discovered that the MPSs with the phase density ranges described herein enable the migration of the reticulocytes to an interface between two adjacent phases of the MPS. Reticulocytes residing at the interface can be easily isolated and collected. In some embodiments, the MPS is formed in a container, e.g., a test tube, or a microhematocrit tube, and the mammalian (e.g., human) blood sample can be added in to the container. Other suitable containers known in the art are contemplated.

In some embodiments, the various components of the blood sample naturally settle in the MPS to their thermodynamically stable states. In some embodiments, during settling the reticulocytes contact one or more of the two phases sequentially. As a result, the enriched reticulocytes will settle to a location in the MPS characteristic of its density, e.g., at the interface between phases of lower and higher density than the reticulocytes. In other embodiments, the multi-phase system containing the blood sample can be centrifuged. The use of centrifuge facilitates the settlement process, by speeding up the migration of the biological analyte, e.g., reticulocyte, to a location in the MPS characteristic of its density. The multi-phase system and the human blood sample (placed on top of the MPS) may be centrifuged for about 1, 2, 3, 4, 5, 6, 7, 8, 9, 10, 15, or 30 min. When the centrifuging process is conducted only for a short period of time, e.g., about 1, 2, 3, 4, or 5 min, the analyte in the blood sample may not have reached its thermodynamic state. Ranges bounded by any of the specific values noted above are also contemplated. In some embodiments, the centrifuging process is stopped while the reticulocyte is still migrating through the phases in the MPS. Such shorter centrifuge may reveal the size or shape profile of the reticulocytes, as reticulocytes of the same density but with different sizes or shapes can have different settlement rates in the MPS (given sufficient time, it is expected that all reticulocytes with the same density will occupy the same location—regardless of differences in sedimentation rates).

In some embodiments, the presence of the reticulocytes is observed by the naked eye or digital quantification analysis.

In some specific embodiments, the analyte in the blood sample in its final state in the MPS can be recorded using digital photography to result in digitized image, which can then be read by a computer program to quantify the amount or the yield of the reticulocytes.

In some embodiments, the enriched reticulocytes can be collected by using a pipet or any method known in the art. The amount of the enriched reticulocytes can be calculated by using flow cytometry.

Figure 7:
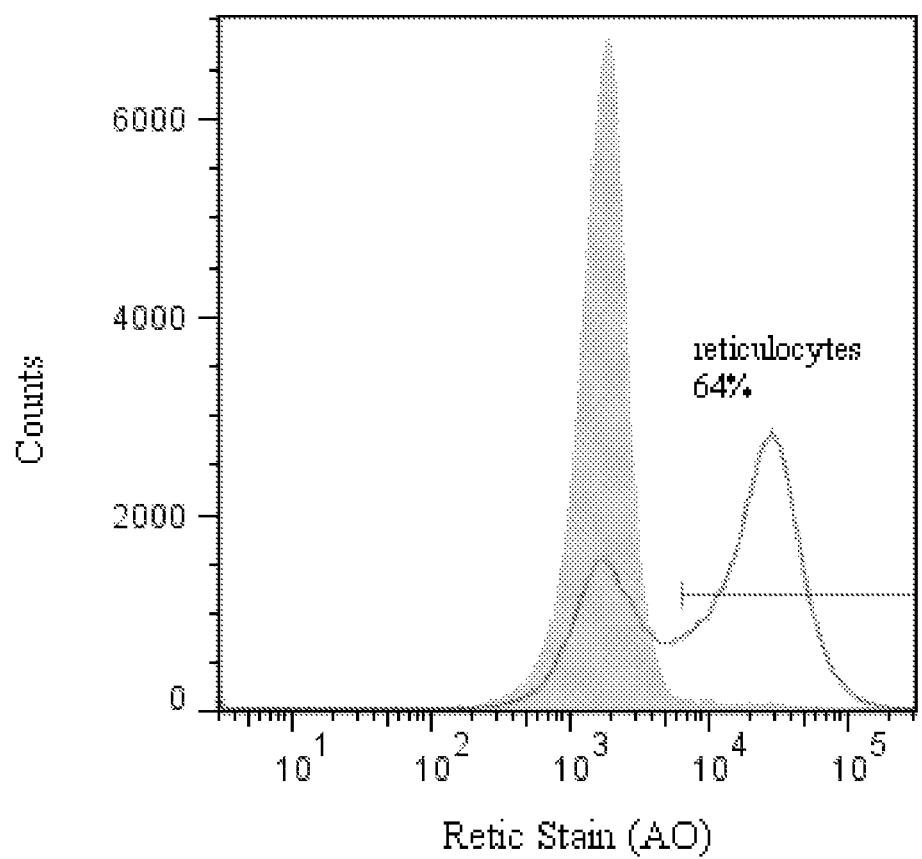
FIG. 7 illustrates a 1:1 volume ratio of blood to a hypertonic AMPS provided enhanced enrichment of reticulocytes.

In some embodiments, the volume ratio of the human blood sample to the multiphase system is about 4:1, 2:1, 1:1, 1:2, 1:3, 1:4, 1:5, or 1:6, or 0.15-4:1, or 0.2-2:1, or 0.3-1:1. Ranges bounded by any of the specific values noted above are also contemplated. It has been surprisingly discovered that the volume ratio of blood to an AMPS can affect the degree of enrichment of reticulocytes. In some embodiments, the volume ratio of the human blood sample to the multiphase system is about 1:1. In some embodiments, the collected reticulocytes have a reticulocytemia of about more than 10%, 20%, 30%, 40%, 50%, 60%, or 70%. In a specific embodiment, a 1:1 volume ratio of blood to AMPS provides a reticulocytes enrichment of greater than 60%. In a specific embodiment, a 1:1 volume ratio of blood to a hypertonic AMPS provided the maximum enrichment of reticulocytes of 64% (FIG. 7).

The tonicity of a MPS system is a colligative property that depends primarily on the number of dissolved particles in solution. Thus, the tonicity of the MPS can be adjusted by using a tonicity adjusting agent. Non-limiting examples of tonicity adjusting agent include dextrose, glycerin, mannitol, KCl, and NaCl.

The biological analyte, e.g., blood cells, may change its size or shape in response to the change of the tonicity of the MPS. As a result, changing tonicity will affect the biological analyte's size and thereby its density and/or migration speed in the MPS. Additionally, changing tonicity will affect the biological analyte's shape and thereby its migration speed through the MPS phases. The tonicity may affect different cells differently. For instance, tonicity may affect reticulocytes and erythrocytes to different extents. Therefore, changing tonicity may provide another parameter to improve the separation and enrichment of the biological analyte, e.g., reticulocytes. In some embodiments, Applicants have surprisingly found that hypertonic MPS provides superior enrichment results for reticulocytes.

Additionally, the addition of certain tonicity-adjusting agents may also change the density of all the phases in the MPS. For instance, the addition of NaCl or KCl will increase the density and tonicity of each of the MPS phases. This provides another way of fine-tuning the density ranges of the MPS phases. In other embodiments, Nycodenz can be added to the phases in the MPSs to adjust the density alone without affecting the tonicity of the phases.

In some embodiments, the enriched reticulocytes are collected with a yield of more than 0.5%, 1%, 1.5%, 2%, 3%, 4%, 5%, 10%, or 20% using the method described herein.

In some embodiments, the method described herein can be adopted to various scales, e.g., the microliter scale, the milliliter scale, or the multi-liter scale.

In yet another aspect, a kit for enriching reticulocytes content in a biological sample using a multi-phase system is described, comprising:

a) at least first and second phase components each of which comprising at least one polymer; and b) instructions for:
   (i) combining the first and second phase components and water, each in a predetermined amount, to create a multi-phase system of described herein, wherein the multiple phases phase-separate to form an interface between the first and second phases; and
   (ii) adding a mammalian blood sample to the multi-phase system to allow the reticulocytes to migrate to the interface between the first and second phases; and
   (iii) collecting a reticulocyte enriched product.

In some embodiments, the kit includes the phase component of each phase in its pure chemical state. The kit may include water or instructions to mix a predetermined amount of water with predetermined amounts of the first and second phase components. In other embodiments, the kit may include stock solutions of the first and second phases with the first and second phase components already dissolved and instructions on how to dilute the stock solutions to obtain the desired first and second phases. In some embodiments, the kit contains instructions to add a biological sample to the pre-prepared MPS and allow the analyte of interest in the sample to migrate to a location in the MPS characteristic of its density. In other embodiments, the kit contains instructions to mix the phase components, water, and the biological sample together to directly form the MPS containing the analyte of interest located at a location in the MPS characteristic of its density.

Certain types of malaria parasites only grow in young red blood cells, or reticulocytes. Creating model systems of malaria would aid research on drug resistance and vaccine development, but requires a routine source of reticulocytes. Described herein is the means to enrich reticulocytes from blood using phase-separated solutions of polymers. These solutions of polymers form steps in density that can be used to separate cells. When blood is added to these systems and then spun in a centrifuge, a layer of cells enriched for reticulocytes is concentrated at a liquid/liquid interface. These cells are suitable for the growth of malaria parasites. The solutions of polymers are self-forming and are stable; these properties make them easy to use and reproducible. Beyond research on malaria, this method should have broad applications for separating cells.

Section 2. Diagnosis of Iron Deficiency Anemia

Over one billion people are estimated to suffer from iron deficiency anemia (IDA). As a result of depleted iron stores in the body, adults may experience chronic fatigue, among other symptoms. Infants with untreated IDA can have permanent cognitive and physical developmental problems. When properly diagnosed, simple interventions exist to treat IDA. While current clinical capabilities can effectively diagnose IDA in the developed world, many countries lack the expensive instrumentation necessary to detect IDA, especially at the point-of-care.

Iron deficiency anemia is characterized by microcytic hypochromic red blood cells caused by low levels of iron in the blood and bone marrow. Diagnostic biomarkers for IDA include serum iron, transferrin saturation, and ferritin. In several clinical conditions, however, these biomarkers do not change rapidly enough to reflect actual iron concentration. Recently, a variety of red blood cell indices have found favor in clinical diagnoses including mean corpuscular volume (MCV), mean corpuscular hemoglobin concentration (MCHC), red blood cell distribution width (RDW), and reticulocyte hemoglobin content (CHr). Relative to healthy patients, iron deficiency anemic patients have low values of MCV, MCHC, and CHr, and a larger RDW.

Red blood indices are becoming increasingly popular for the diagnosis of iron deficiency anemia because they quickly respond to iron level changes in the body, in contrast to serum iron or ferritin, and require a less painful and invasive procedure for the patient than the gold standard measurement of iron in bone marrow. Red blood cell indices measured by a complete blood count require a hematology analyzer. A hematology analyzer, however, requires a large capital investment (~$50,000) and only two major brands test for reticulocyte hemoglobin content (CHr), an index gaining popularity in diagnosing IDA. An inexpensive, fast, and simple method that approaches the specificity and sensitivity provided by a hematology analyzer could find widespread clinical use.

An inexpensive and point-of-care tool for the diagnosis of iron deficiency anemia is especially needed in resource-limited countries where the rate of iron deficiency anemia is often very high and hematology analyzers are only available in major hospitals.

In these settings, anemia is often diagnosed by hemoglobin content or hematocrit using portable hemoglobin tests (e.g., Hemocue) or a spun hematocrit. When anemia is diagnosed by these methods alone, the underlying source of the anemia (e.g., iron deficiency, malaria, hemoglobinopathy) remains unknown. More information is necessary to differentially diagnose anemia so that health care workers can use appropriate interventions.

A tool to separate iron deficiency anemia quickly from other forms of anemia would allow better care and a better use of resources at the level of primary healthcare.

Beta-thalassemia minor (i.e. β-thalassemia trait: β-TT) is a benign genetic disorder that presents a confounding diagnosis to IDA because both conditions result in microcytic and hypochromic red blood cells. Identification of β-TT is vital to aid in prevention of β-thalassemia major through genetic counseling; transmission of β-thalassemia is autosomal recessive and so heterozygous carriers can attempt to mitigate the risk of a homozygous offspring.

Due to the characteristically smaller (bimodal) RDW and larger total red blood cell count for patients with β-thalassemia trait, it can be distinguished from iron deficiency anemia. A population of cells with a larger RDW will likely have a larger distribution in the density of red blood cells.

Described herein is a straightforward, low cost, and efficient system and method for diagnosis of β-thalassemia trait and/or iron deficiency anemia using multi-phase systems. In some embodiments, a MPS comprising a two-phase system is used for quick and easy identification of the presence of β-TT or IDA trait red blood cells without specifying or identifying which trait (β-TT or IDA) red blood cells are present. These MPS offers quick identification of any patient with either β-TT or IDA red blood cells.

In some embodiments, the MPS is a two-phase system and the density ranges of the two phases are described herein and selected to allow the iron deficiency anemia red blood cells or β-thalassemia trait red blood cells to be easily identified. For instance, the densities of the two phases may be selected so that iron deficiency anemia red blood cells or β-thalassemia trait red blood cells will settle and reside in the interface of the first and second phases to allow easy identification of the iron deficiency anemia or β-thalassemia trait. In a specific embodiment, the MPS is an aqueous two-phase system having the first and second densities at about 1.0784 g/cm$^3$ and 1.0810 g/cm$^3$, respectively. In one embodiment, the first and second phase components are dextran and Ficoll, respectively.

In some embodiments, once the patient with either β-TT or IDA red blood cells is identified, another MPS comprising at least three phases is used to further distinguish between the two red blood cells traits (β-TT and IDA). Specifically, the three phases are designed so that after separation and settlement, β-TT trait red blood cells, if present in the patient blood, will reside at one of the two internal interfaces of the three phases, and IDA trait red blood cells, if present in the patient blood, will reside at the other interface. In these embodiments, the method offers further clarification regarding which of the two red blood cells traits (β-TT and IDA), or both, are present in a mammalian blood sample.

In some embodiments, the density difference between the bottom two phases are sufficiently small (less than 0.002 g/cm$^3$) to allow the separation and identification of the two red blood cells traits (β-TT and IDA).

In some embodiments, the diagnosis of β-TT and IDA described herein is conducted for mammalian blood. In some specific embodiments, the mammal is human.

In one aspect, an aqueous multi-phase system for diagnosis of iron deficiency anemia is described, including two or more phase-separated phases comprising:

a first aqueous phase comprising a first phase component and having a first density between about 1.025 g/cm$^3$ and about 1.085 g/cm$^3$; and a second aqueous phase comprising a second phase component and having a second density between about 1.075 g/cm$^3$ and about 1.095 g/cm$^3$;

wherein the first density is lower than the second density; and each of the first and second phase components comprises at least one polymer.

In some embodiments, the first density is about 1.025-1.080 g/cm$^3$, 1.025-1.075 g/cm$^3$, 1.025-1.070 g/cm$^3$, 1.025-1.065 g/cm$^3$, 1.025-1.060 g/cm$^3$, 1.025-1.055 g/cm$^3$, 1.025-1.050 g/cm$^3$, 1.030-1.080 g/cm$^3$, 1.030-1.075 g/cm$^3$, 1.030-1.070 g/cm$^3$, 1.030-1.065 g/cm$^3$, 1.030-1.060 g/cm$^3$, 1.030-1.055 g/cm$^3$, 1.030-1.050 g/cm$^3$, 1.040-1.080 g/cm$^3$, 1.040-1.075 g/cm$^3$, 1.040-1.070 g/cm$^3$, 1.040-1.065 g/cm$^3$, 1.040-1.060 g/cm$^3$, 1.040-1.055 g/cm$^3$, 1.040-1.050 g/cm$^3$, 1.050-1.080 g/cm$^3$, 1.050-1.075 g/cm$^3$, 1.050-1.070 g/cm$^3$, 1.050-1.065 g/cm$^3$, 1.050-1.060 g/cm$^3$, 1.050-1.055 g/cm$^3$, 1.055-1.080 g/cm$^3$, 1.055-1.075 g/cm$^3$, 1.055-1.070 g/cm$^3$, 1.055-1.065 g/cm$^3$, 1.055-1.060 g/cm$^3$, 1.060-1.080 g/cm$^3$, 1.060-1.075 g/cm$^3$, 1.060-1.070 g/cm$^3$, 1.060-1.065 g/cm$^3$, 1.065-1.080 g/cm$^3$, 1.065-1.075 g/cm$^3$, 1.070-1.080 g/cm$^3$, 1.075-1.080 g/cm$^3$, or 1.075-1.085 g/cm$^3$.

In some embodiments, the second density is about 1.075-1.090 g/cm$^3$, 1.075-1.085 g/cm$^3$, 1.075-1.080 g/cm$^3$, 1.080-1.095 g/cm$^3$, 1.080-1.090 g/cm$^3$, 1.080-1.085 g/cm$^3$, 1.085-1.095 g/cm$^3$, or 1.085-1.090 g/cm$^3$. In some specific embodiments, the second density is about 1.080, 1.081, 1.082, 1.085, or 1.090 g/cm$^3$.

In some embodiments, the first density is about 1.070-1.083 g/cm$^3$ and the second density is about 1.080-1.085 g/cm$^3$. The first density is selected to be greater than that of the mammalian plasma and the second density is selected to be less than that of the healthy red blood cells. Ranges of the first and second densities are contemplated because other factors such as tonicity of the solution will affect the densities of the red blood cells.

The research in this field does not provide the exact density of iron deficiency anemia red blood cells or β-thalessemia trait red blood cells. As described herein, Applicants have surprisingly identified the density ranges of the first and second phases to allow an easy identification of the presence of iron deficiency anemia or β-thalessemia trait red blood cells, e.g., the presence or absence of iron deficiency anemia red blood cells or β-thalessemia trait red blood cells at the interface of the first and second aqueous phases. Similarly, Applicants have surprisingly identified the density ranges of the first, third, and second phases to distinguish between the iron deficiency anemia and the β-thalessemia trait red blood cells, e.g., the presence or absence of iron deficiency anemia red blood cells at the interface of the first and third aqueous phases, and the presence or absence of the β-thalessemia trait red blood cells at the interface of or in the third and second aqueous phases. Additionally, Applicants have surprisingly discovered that the small density difference between the third and second phases (e.g., about 0.002 g/cm$^3$) allow one to distinguish easily between the IDA and the β-TT red blood cells by using the three-phase system described herein.

In other embodiments, if only the presence or absence of the β-TT trait red blood cells is of interest, a MPS comprising the second and third phases described herein can be used (e.g., an aqueous two-phases system) to observe any presence of the β-TT trait red blood cells at the interface of the second and third phases.

Similarly, in other embodiments, if only the presence or absence of the IDA trait red blood cells is of interest, a MPS comprising the first and third phases described herein can be used (e.g., an aqueous two-phases system) to observe any presence of the IDA trait red blood cells at the interface of the first and third phases.

The difficulties to measure the single cell density of the red blood cells is illustrated by, e.g., Grover, W. et al., *Measuring single-cell density*, PNAS Early Edition, (http://www.pnas.org/content/early/2011/06/15/1104651108).

Applicants have surprisingly found that the density ranges for the MPS phases to identify iron deficiency anemia and β-thalessemia trait red blood cells can be discovered/investigated in two ways: (1) empirically observing patients with a low MCHC (mean corpuscular hemoglobin concentration) which shows a spread of red blood cells in the tube after centrifugation; and (2) by using reported ranges of values for MCHC for β-thalessemia trait, iron deficiency anemia, and normal blood. By using the MCHC values as a reference, the various ranges of the densities for the MPS phases described herein are evaluated and tested.

In some embodiments, the MPS is a two-phase system and the density ranges of the two phases are described herein and selected to allow the iron deficiency anemia red blood cells or β-thalessemia trait red blood cells to be easily identified. For instance, the densities of the two phases may be selected so that iron deficiency anemia red blood cells or β-thalessemia trait red blood cells will settle and reside in the interface of the first and second phases to allow easy identification of the IDA or β-TT. In a specific embodiment, the MPS is an aqueous two-phase system having the first and second densities at about 1.0784 g/cm$^3$ and 1.0810 g/cm$^3$, respectively. In one embodiment, the first and second phase components are dextran and Ficoll, respectively.

In some other embodiments, the aqueous multi-phase system further comprises: a third aqueous phase comprising a third phase component and having a third density between about 1.073 g/cm$^3$ and about 1.093 g/cm$^3$; wherein the third density is higher than the first density but lower than the second density; and the third phase component comprises at least one polymer.

In some embodiments, the third density is less than about 0.002 g/cm$^3$, 0.0019 g/cm$^3$, 0.0018 g/cm$^3$, 0.0017 g/cm$^3$, 0.0016 g/cm$^3$, 0.0015 g/cm$^3$, 0.0014 g/cm$^3$, 0.0013 g/cm$^3$, 0.0012 g/cm$^3$, 0.0011 g/cm$^3$, 0.0010 g/cm$^3$, 0.0009 g/cm$^3$, 0.0008 g/cm³, 0.0007 g/cm³, 0.0006 g/cm³, 0.0005 g/cm³, 0.0004 g/cm³, 0.0003 g/cm³, 0.0002 g/cm³, or 0.0001 g/cm³ lower than the second density. Ranges bounded by any of the specific values noted above are also contemplated.

In some embodiments, the first, third, and second densities are about 1.040-1.055 g/cm³, 1.075-1.085 g/cm³, and 1.080-1.085 g/cm³, respectively. In one specific embodiment, the first, third, and second densities are about 1.0505 g/cm³, 1.0810 g/cm³, and 1.0817 g/cm³, respectively. In one specific embodiment, the first, third, and second phase components are PVA, dextran and Ficoll, respectively.

In some embodiments, the first and second phase components are selected so that the resulting two phases phase separate to form the two-phase system. Similarly, in other embodiments, the first, third, and second phase components are selected so that the resulting three phases phase separate to form the three-phase system. In some embodiments, the first, second, and third phase components are each selected from the group consisting of Caboxy-polyacrylamide, Dextran, Ficoll, N,N-dimethyldodecylamine N-oxide, poly(2-ethyl-2-oxazoline), poly(acrylic acid), poly(ethylene glycol), poly(methacrylic acid), poly(vinyl alcohol), polyacrylamide, polyethyleneimine, hydroxyethyl cellulose, poly(2-acrylamido-2-methyl-1-propanesulfonic acid), polyvinylpyrrolidone, Nonyl, polyallylamine, (hydroxypropyl) methyl cellulose, diethylaminoethyl-dextran, and nonylphenol polyoxyethylene 20, copolymer, terpolymer, block copolymer, random polymer, linear polymer, branched polymer, crosslinked polymer, and dendrimer system thereof. Generally, any two- or three-phase system described herein can be used, provided that the density of each phase falls in the ranges of the phase densities described herein.

The concentration of the phase component in each phase also can be fine-tuned to adjust the density of each phase so that that the density of each phase falls in the ranges of the phase densities described herein. In other embodiments, the density ranges of the phases can also be achieved by adding additives such as Nycodenz. In some embodiments, the concentration of the first phase component in the first phase or the concentration of the second phase component in the second phase is between about 1-40% (w/v). In some specific embodiments, the concentration of the first phase component in the first phase or the concentration of the second phase component in the second phase is about 5%, 10%, 15%, 20%, or 25% (w/v). In some specific embodiments, the concentration of the third phase component in the third phase is between about 1-40% (w/v) or about 5%, 10%, 15%, 20%, or 25% (w/v). In some specific embodiments, the concentration of the first phase component in the first phase, the concentration of the third phase component in the third phase, or the concentration of the second phase component in the second phase is about 5%-25%, 10%-20%, or 15%-20% (w/v).

As described herein, the tonicity of a MPS system can be adjusted using a tonicity adjusting agent including, but are not limited to, dextrose, glycerin, mannitol, $NaH_2PO_4$ (or its hydrate form), $KH_2PO_4$, KCl, and NaCl. In some embodiments, the aqueous multi-phase system for the diagnosis of iron deficiency anemia and/or β-thalassemia trait is isotonic.

In yet another aspect, a method of diagnosing iron deficiency anemia or β-thalassemia trait is described, comprising:

(a) providing an aqueous multi-phase system described herein, wherein the multi-phase system comprises at least two phases phase-separating to form an interface between first and second phases;

(b) adding a mammalian blood sample comprising red blood cells to the multi-phase system to allow the red blood cells to migrate to a location(s) in the multi-phase system characteristic of their density; and (c) observing the presence or absence of red blood cells at the interface of the first and second aqueous phases; wherein the presence of red blood cells at the interface of the first and second aqueous phases indicates iron deficiency anemia red blood cells or β-thalassemia trait red blood cells.

In some embodiments, the MPS is an aqueous two-phase system, which allows a quick and easy diagnosis of iron deficiency anemia or β-thalassemia trait by allowing the iron deficiency anemia or β-thalassemia trait blood cells to reside at the interface of the first and second phases.

In some embodiments, step (b) comprises allowing the analyte in the mammalian blood sample to naturally settle to its thermodynamically stable state in the multi-phase system. As a result, the iron deficiency anemia or β-thalassemia trait blood cells will settle to a location in the MPS characteristic of its density, e.g., at the interface of the first and second phases. In other embodiments, step (b) comprises centrifuging the multi-phase system and the mammalian blood sample. The use of centrifuge facilitates the settlement process. In some embodiments, step (b) comprises centrifuging the multi-phase system and the mammalian blood sample for about 1, 2, 3, 4, 5, 6, 7, 8, 9, 10, 15, or 30 min.

When the centrifuging process is conducted only for a short period of time, e.g., about 1, 2, 3, 4, or 5 min, the analyte in the blood sample may not have reached its thermodynamic or equilibrium state in the MPS. In some embodiments, the centrifuging process is stopped while the blood cells are still migrating through the phases in the MPS. Such shorter centrifuge may reveal the size, density, or shape profile of the blood cells with the same density as blood cells, as blood cells of the same density but with different sizes or shapes can have different settlement rates in the MPS (given sufficient time, it is expected that all blood cells with the same density will occupy the same location—regardless of differences in sedimentation rates). Thus, in some embodiments, the method further comprises obtaining the size distribution profile of the iron deficiency anemia red blood cells or β-thalassemia trait red blood cells.

In some embodiments, the presence or absence of iron deficiency anemia red blood cells or β-thalassemia trait red blood cells is observed by the naked eye or digital quantification analysis. In some specific embodiments, the analyte in the blood sample in its final state in the MPS can be recorded using digital photography to result in a digitized image, which can then be read by a computer program to identify the presence or absence of iron deficiency anemia red blood cells or β-thalassemia trait red blood cells.

In some embodiments, the volume ratio of the mammalian blood sample to the multiphase system is about 4:1, 2:1, 1:1, 1:2, 1:3, 1:4, 1:5, or 1:6, or 0.15-4:1, or 0.2-2:1, or 0.3-1:1. Ranges bounded by any of the specific values noted above are also contemplated.

In another aspect, a method of diagnosing iron deficiency anemia and β-thalassemia trait is described, comprising:

(a) providing an aqueous multi-phase system described herein, wherein the multi-phase system comprises three phases phase-separate ting form interfaces between first and third phases and between third and second phases;

(b) adding a mammalian blood sample comprising red blood cells to the multi-phase system to allow the red blood cells to migrate to a location(s) in the multi-phase system characteristic of their density; and (c) observing the presence or absence of iron deficiency anemia red blood cells at the interface of the first and third aqueous phases, and the presence or absence of the β-thalessemia trait red blood cells at the interface of the third and second aqueous phases' interfaces or within the phases.

In some embodiments, the MPS used herein is a three-phase system which allows distinguishing between IDA and β-TT. Specifically, in some embodiments, the densities of the first, third, and second phases are selected so that the iron deficiency anemia red blood cells will settle at the interface of the first and third aqueous phases, and the β-thalessemia trait red blood cells will settle at the interface of or in the third and second aqueous phases. Centrifuge (1, 2, 3, 4, 5, 6, 7, 8, 9, 10, 15, or 30 min) of the multi-phase system and the mammalian blood sample may be used to accelerate the process. In some embodiments, step (b) further comprises allowing the analyte in the blood sample to reach thermodynamic equilibrium in the MPS.

In some embodiments, during migration the red blood cells contacts one or more of the two or more phases sequentially. In these embodiments, the introduction of the blood sample does not disrupt the multi-phase system.

In some embodiments, the presence or absence of iron deficiency anemia red blood cells or β-thalessemia trait red blood cells is observed by the naked eye or digital quantification analysis.

In other embodiments, the densities of the phases of the MPSs are selected so that the analytes of interest, e.g., red blood cells, are within one of the phases. In these embodiments, the phases containing the analytes of interest can be collected and analyzed.

In other embodiments, the MPS include the first and the third phases as described above. These MPSs allows observing the presence or absence of iron deficiency anemia red blood cells at the interface of the first and third aqueous phases. In other embodiments, the MPS include the second and the third phases as described above. These MPSs allows observing the presence or absence of the β-thalessemia trait red blood cells at the interface of the third and second aqueous phases' interfaces or within the phases.

In yet another aspect, a kit for the diagnosis of iron deficiency anemia using a multi-phase system is described, comprising:
a) at least a first and second phase components, each comprising at least one polymer; and
b) instructions for:
(i) combining the first and second phase components and water, each in a predetermined amount, to create a multi-phase system described herein, wherein the multiple phases phase-separate to form an interface between the first and second phases; and
(ii) adding a mammalian blood sample to the multi-phase system to allow the red blood cells to migrate to a location(s) characteristic of their densities; and
(iii) observing the presence or absence of red blood cells at the interface of the first and second aqueous phases; wherein
the presence of red blood cells at the interface of the first and second aqueous phases indicates iron deficiency anemia red blood cells or β-thalessemia trait red blood cells In yet another aspect, a kit for the diagnosis of iron deficiency anemia and or β-thalessemia trait using a multi-phase system is described, comprising:
a) at least a first, second, and third phase component each comprising at least one polymer; and
b) instructions for:
(i) combining the first, second, and third phase components and water, each in a predetermined amount, to create a multi-phase system as described herein, wherein the multiple phases phase-separate to form interfaces between the first and third phases and between the third and second phases; and
(ii) adding a mammalian blood sample to the multi-phase system to allow the red blood cells to migrate to a location(s) characteristic of their densities; and
(iii) observing the presence or absence of iron deficiency anemia red blood cells at the interface of the first and third aqueous phases, and the presence or absence of the β-thalessemia trait red blood cells at the interface of or in the third and second aqueous phases.

In some embodiments, the kit includes the phase component of each phase in its pure chemical state. The kit may include water or instructions to mix a predetermined amount of water with predetermined amounts of the first, third, and second phase components. In other embodiments, the kit may include stock solutions of the first, third, and second phases with the first and second phase components already dissolved and instructions on how to dilute the stock solutions to obtain the desired first and second phases.

Therefore, using the two-phase systems described herein, one can quickly and easily diagnose microcytic and hypochromic anemia by the presence of an observable band of RBCs at the liquid/liquid interface above the packed normal RBCs. Furthermore, IDA and β-thalessemia trait red blood cells can also be quickly and easily distinguished by using a three-phase system by capturing microcytic and hypochromic RBCs at two liquid/liquid interfaces and allows for the differentiation between β-thalessemia trait and iron deficiency anemia owing to the difference in RBC density distribution between the two conditions.

Section 3. Diagnosis of Sickle Cell Disease

Over 300,000 children (approximately 1% of births) are born with sickle cell disease (SCD) in Africa each year. Sickle cell disease is a genetic disorder caused by an array of genotypes (e.g., homozygous sickle cell disease—Hb SS, and hemoglobin SC disease—Hb SC) that lead to the sickling of erythrocytes and associated pathologies. Children with sickle cell disease suffer high mortality due to acute vaso-occlusive crises and increased risk of bacteremia. Although inexpensive interventions exist to limit infection (e.g., penicillin prophylaxis, vaccinations) and reduce childhood mortality, over 50% of children <5 years of age die in low-resource areas due to a lack of diagnosis. Standard diagnostic procedures that detect sickle cell disease are either unfeasible in low-resource settings—where the disease is highly prevalent—or do not differentiate between sickle cell disease and the non-disease, sickle cell trait (Hb AS). This unmet need has motivated the recent development of creative diagnostic methods for sickle cell disease using blood stains on paper devices and hemolysis in solutions of sucrose.

Sickle cell disease also lacks simple metrics for management. Standard diagnostic tests lack the ability to provide prognostic information. Genetic testing only confirms that the mutations for sickle cell disease are present. Hemoglobin electrophoresis (HE) and high performance liquid chromatography (HPLC) can quantify the level of fetal hemoglobin—a useful, but incomplete, modulator of clinical manifestations. Biophysical indicators, such as the rate of jamming of erythrocytes in microfluidic channels, have been proposed as integrative sources of information that could aid the management of sickle cell disease—large clinical studies are still needed to verify this claim. The distribution of density of red blood cells provides another biophysical indicator that is closely related to sickle cell disease pathophysiology; the dehydration that leads to the formation of sickle cells exponentially increases the polymerization of hemoglobin S. Dehydration increases the density of the cell by reducing the volume and increasing the ratio of dense protein to less dense water in the cell.

In some embodiments, the diagnosis of sickle cell disease and its subtypes is conducted for mammalian blood. In some specific embodiments, the mammal is human.

The literature in this field has reported the values for the sickle cell disease cells and its subtypes with discrepancies. Applicants have surprisingly found that the density ranges described herein for each of the MPS phases enables the identification of SCD and its subtypes with high sensitivity (e.g., more than 70%, 85%, 90%, or 95%) and specificity. Ranges bounded by any of the specific values noted above are also contemplated. Described herein are two- or three-phases systems by which a visual evaluation can be used to identify sickle cell disease with high sensitivity (e.g., more than 70%, 85%, 90%, or 95%) and specificity (e.g., more than 90%, 91%, 92%, 93%, 94%, 95%, 96%, 97%, 98%, or 99%). Ranges bounded by any of the specific values noted above are also contemplated. The MPS described herein can also distinguish the main subclasses of SCD (Hb SS and Hb SC). The ranges for the densities of each of the MPS phases are contemplated because other factors such as tonicities of the solution may affect the densities of the sickle cell disease cells.

In some embodiments, the MPS comprises a two phase system described herein where the presence of erythrocyte below the second phase (which is the bottom phase) indicates sickle cell disease. The density of the first phase is selected to be more than that of the blood plasma but less than that of the SCD erythrocyte. The density of the second phase is selected to be less than that of the sickle cell disease erythrocyte.

In other embodiments, the MPS comprises a three phase system described herein where the presence of erythrocyte below the second phase (which is the bottom phase) indicates sickle cell disease, a pattern that the amount of erythrocytes present at the interface of the first (top phase) and third (middle phase) phases is more than the amount of erythrocytes present at the interface of the third and second phases indicates homozygous sickle cell disease (Hb SS), and a pattern that the amount of erythrocytes present at the interface of the third and second phases is about the same or more than the amount of erythrocytes present at the interface of the first and third phases indicates hemoglobin sickle cell disease (Hb SC). The density of the first phase is selected to be more than that of the blood plasma but less than that of the SCD erythrocyte. The density of the second phase is selected to be less than that of the sickle cell disease erythrocyte. Additionally, the densities of the first, second, and third phases are selected so that the patterns described above can be observed for the different SCD subtypes.

In one aspect, an aqueous multi-phase system for diagnosis of sickle cell disease is described, comprising two or more phase-separated phases comprising:
a first aqueous phase comprising a first phase component and having a first density between about 1.025 g/cm³ and about 1.140 g/cm³; and
a second aqueous phase comprising a second phase component and having a second density between about 1.100 g/cm³ and about 1.140 g/cm³;
wherein
the first density is lower than the second density; and
each of the first and second phase components comprises at least one polymer.

The densities of the SCD cells are not consistently reported by the literature, some of which are conflicting each other. Applicants have surprisingly found that the density ranges for the MPS phases effectively result in effective identification of SCD and its subtypes.

The density of each of the phases is selected to allow identification of the SCD cells. In some embodiments, the first density is about 1.025-1.140 g/cm³, 1.025-1.130 g/cm³, 1.025-1.120 g/cm³, 1.025-1.110 g/cm³, 1.025-1.100 g/cm³, 1.025-1.090 g/cm³, 1.025-1.095 g/cm³, 1.025-1.080 g/cm³, 1.025-1.075 g/cm³, 1.025-1.070 g/cm³, 1.025-1.065 g/cm³, 1.025-1.060 g/cm³, 1.025-1.055 g/cm³, 1.025-1.050 g/cm³, 1.030-1.080 g/cm³, 1.030-1.075 g/cm³, 1.030-1.070 g/cm³, 1.030-1.065 g/cm³, 1.030-1.060 g/cm³, 1.030-1.055 g/cm³, 1.030-1.050 g/cm³, 1.040-1.080 g/cm³, 1.040-1.075 g/cm³, 1.040-1.070 g/cm³, 1.040-1.065 g/cm³, 1.040-1.060 g/cm³, 1.040-1.055 g/cm³, or 1.040-1.050 g/cm³. In some specific embodiments, the first density is about 1.025, 1.030, 1.035, 1.045, 1.040, 1.050, 1.055, 1.060, 1.065, 1.070, 1.075, 1.078, 1.080, 1.090, 1.100, 1.110, 1.120, 1.130, or 1.140 g/cm³. In some specific embodiments, the first density is about 1.025-1.030, 1.035-1.050, 1.055-1.070, or 1.075-1.080 g/cm³.

In some embodiments, the second density is about 1.110-1.140 g/cm³, 1.110-1.130 g/cm³, 1.110-1.125 g/cm³, 1.110-1.120 g/cm³, 1.115-1.125 g/cm³, 1.115-1.120 g/cm³, or 1.120-1.125 g/cm³. In some specific embodiments, the second density is about 1.120, 1.125, or 1.129 g/cm³. In some specific embodiments, the second density is about 1.115-1.130 g/cm³. In some specific embodiments, the first and second densities are about 1.078 g/cm³ and 1.129 g/cm³, or 1.077 g/cm³ and 1.120 g/cm³, respectively. In some specific embodiments, the first and second densities are about 1.075-1.0798 g/cm³ and 1.120-1.129 g/cm³, respectively. Ranges bounded by any of the specific values noted above are also contemplated.

In some embodiments, an easy and quick method of identifying the SCD cells using the MPSs is described. Specifically, the density of the first phase is selected so that its density is greater than the mammalian plasma and the mammalian plasma does not interfere with the diagnosis. In some embodiments, the density of the first phase is selected so that it does not significantly dilute the other phases which means that the system is insensitive to hematocrit. Additionally, the density of the second phase is selected so that the SCD erythrocytes will be below the second phase for easy identification.

In some embodiments, the presence of cells with a high density correlates with the presence of SCD. Samples that had a visible red band at the bottom of the AMPS correlated strongly with the presence of SCD. Conversely, samples negative for SCD rarely had red cells visibly present at the bottom of the AMPS (Table 7). The SCD-AMPS-2 had a true positive rate (sensitivity) of 90% with a Jeffreys 95% confidence interval (C.I.) of 73%-98% and a true negative rate (specificity) of 97% (C.I.=86%-100%).

In other embodiments, the MPS further comprises a third aqueous phase. This third phase is introduced to further distinguish the different subtypes of the SCD. Additionally, the densities of the first, second, and third phases are selected so that the patterns for the different SCD subtypes can be observed, i.e., a pattern that the amount of erythrocytes present at the interface of the first (top phase) and third (middle phase) phases is more than the amount of erythrocytes present at the interface of the third and second phases indicates homozygous sickle cell disease (Hb SS), and a pattern that the amount of erythrocytes present at the interface of the third and second phases is about the same or more than the amount of erythrocytes present at the interface of the first and third phases indicates hemoglobin sickle cell disease (Hb SC). The density of the third phase can be generally determined by the densities of the sub-populations of SCD erythrocytes. However, density ranges for the third phase are contemplated as other factors such as tonicity may affect the density of the SCD erythrocytes.

In these embodiments, the MPS further comprises: a third aqueous phase comprising a third phase component and having a third density between about 1.075 g/cm$^3$ and about 1.120 g/cm$^3$; wherein the third density is higher than the first density but lower than the second density; and the third phase component comprises at least one polymer. The third phase is in between the first and the second phases.

In some embodiments, the third density is about 1.085-1.110 g/cm$^3$, 1.090-1.110 g/cm$^3$, 1.095-1.110 g/cm$^3$, 1.100-1.110 g/cm$^3$, 1.105-1.110 g/cm$^3$, 1.085-1.105 g/cm$^3$, 1.090-1.105 g/cm$^3$, 1.095-1.105 g/cm$^3$, 1.100-1.105 g/cm$^3$, 1.085-1.100 g/cm$^3$, 1.090-1.100 g/cm$^3$, 1.095-1.100 g/cm$^3$, 1.085-1.095 g/cm$^3$, or 1.090-1.095 g/cm$^3$.

In some embodiments, the first, third, and second densities are about 1.077 g/cm$^3$, 1.108 g/cm$^3$, and 1.120 g/cm$^3$, respectively. In some embodiments, the first, third, and second densities are about 1.075-1.083 g/cm$^3$, 1.105-1.110 g/cm$^3$, and 1.115-1.125 g/cm$^3$, respectively.

In some embodiments, the density of each of the first, third, and second phases is selected to distinguish the subtypes of the SCD. Specifically, the three phases have densities so that a pattern with the amount of erythrocytes present at the interface of the first and third phases is more than the amount of erythrocytes present at the interface of the third and second phases indicates homozygous sickle cell disease (Hb SS); and a pattern that the amount of erythrocytes present at the interface of the third and second phases is about the same or more than the amount of erythrocytes present at the interface of the first and third phases indicates hemoglobin sickle cell disease (Hb SC).

Figure 26:
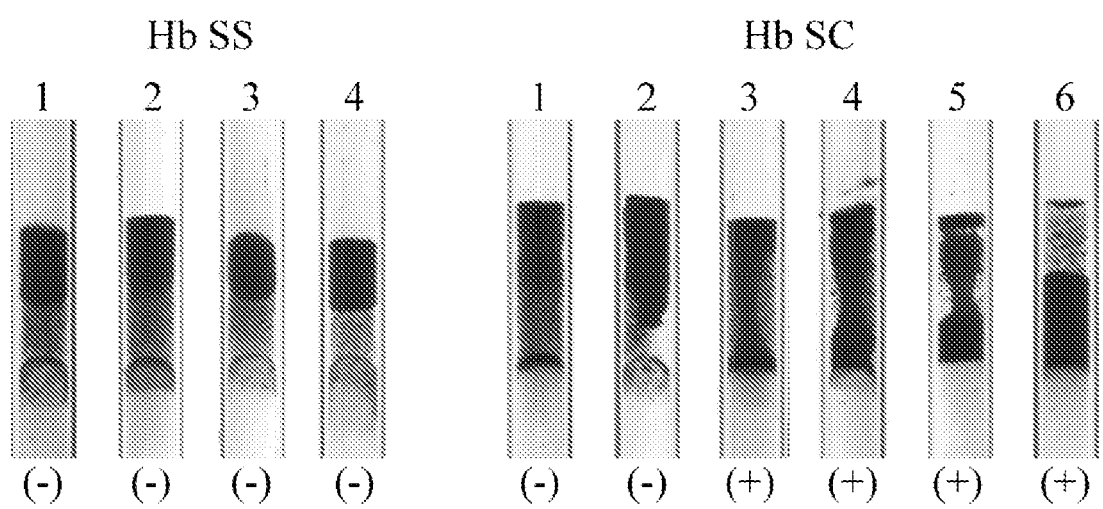
FIG. 26 shows examples of the patterns of red cells at the liquid interfaces for Hb SC and Hb SS in the SCD-AMPS-3 system.

In some specific embodiments, the three-phase MPS has a sensitivity of 91% (C.I.=78%-98%), and a specificity of 88% (C.I.=74%-98%). To reduce biased evaluation using the naked-eye observation, each test can be evaluated digital analysis (e.g. using a flatbed scanner or a camera) (FIG. 26). By contrast, blood from samples with Hb SS had two distinct bands of red with a clear majority of red cells at the upper liquid interface. These differences in the distribution of cells allowed one to distinguish visually between Hb SC and Hb SS, the two predominant forms of SCD with a sensitivity of 67% (C.I.=29%-92%) and a specificity of 100% (C.I.=88%-100%). Centrifugation for an additional 10 minutes increased the sensitivity to 83% (C.I.=44%-98%).

In some specific embodiments, the first, second, and third phase components are each selected from the group consisting of Caboxy-polyacrylamide, Dextran, Ficoll, N,N-dimethyldodecylamine N-oxide, poly(2-ethyl-2-oxazoline), poly(acrylic acid), poly(ethylene glycol), poly(methacrylic acid), poly(vinyl alcohol), polyacrylamide, polyethyleneimine, hydroxyethyl cellulose, poly(2-acrylamido-2-methyl-1-propanesulfonic acid), polyvinylpyrrolidone, Nonyl, polyallylamine, (hydroxypropyl)methyl cellulose, diethylaminoethyl-dextran, nonylphenol polyoxyethylene 20, copolymer, terpolymer, block copolymer, random polymer, linear polymer, branched polymer, crosslinked polymer, and dendrimer system thereof.

In some specific embodiments, the first and second components are PEG and Ficoll or PEG and PVA, respectively. In some specific embodiments, the first, third, and second components are PEG, dextran, and PVA, respectively.

The concentration of the phase component in each phase also can be fine-tuned to adjust the density of each phase so that that the density of each phase falls in the ranges of the phase densities described herein. In some embodiments, the concentration of the first phase component in the first phase or the concentration of the second phase component in the second phase is between about 1-40% (w/v). In some embodiments, the concentration of the first phase component in the first phase or the concentration of the second phase component in the second phase is about 5%, 10%, 15%, 20%, or 25% (w/v). In some embodiments, the concentration of the third phase component in the third phase is between about 1-40% (w/v) or about 5%, 10%, 15%, 20%, or 25% (w/v). In some embodiments, the concentration of the first phase component in the first phase, the concentration of the second phase component in the second phase, or the concentration of the third phase component in the third phase is about 5%-10%, 10%-15%, or 15%-25% (w/v). In some embodiments, the densities of the phases are achieved with the addition of density-adjusting additives such as Nycodenz.

In some embodiments, the aqueous multi-phase system is isotonic.

In yet another aspect, a method of diagnosing sickle cell disease is described, comprising:

(a) providing an aqueous multi-phase system described herein, wherein the multi-phase system comprises two phases phase-separating to form an interface between first and second phases; and (b) adding a mammalian blood sample comprising erythrocytes to the multi-phase system to allow the erythrocytes to migrate to a location(s) in the multi-phase system characteristic of their density; and (c) observing the presence or absence of erythrocytes below the second phase;

wherein the presence of erythrocytes below the second phase indicates sickle cell disease.

In some embodiments, step (b) comprises adding the mammalian blood sample to the multi-phase system in a container to allow the multiple phases to phase-separate to form an interface between the second phase and the bottom of the container and observe the presence or absence of erythrocytes at the interface between the second phase and the bottom of the container. The container may be a flask, a tube, or any other container known in the art.

In yet another aspect, a method of diagnosing subtypes of sickle cell disease is described, comprising:

(a) providing an aqueous multi-phase system described herein, wherein the multi-phase system comprises three phases phase-separating to form interface between first and third phases and between first and second phases, respectively; and (b) adding a mammalian blood sample comprising erythrocytes to the multi-phase system to allow the erythrocytes to migrate to a location(s) in the multi-phase system characteristic of their density; and (c) observing the presence or absence of erythrocytes at the interfaces of the first and third aqueous phases and of the third and second aqueous phases;

wherein
the presence of erythrocyte below the second phase indicates sickle cell disease;
a pattern that the amount of erythrocytes present at the interface of the first and third phases is more than the amount of erythrocytes present at the interface of the third and second phases indicates homozygous sickle cell disease (Hb SS); and
a pattern that the amount of erythrocytes present at the interface of the third and second phases is about the same or more than the amount of erythrocytes present at the interface of the first and third phases indicates hemoglobin sickle cell disease (Hb SC).

In some embodiments, during migration the reticulocytes contact one or more of the multi-phases sequentially. In some embodiments, the pattern that the amount of erythrocytes present at the interface of the first and third phases is significantly more than the amount of erythrocytes present at the interface of the third and second phases indicates homozygous sickle cell disease (Hb SS).

In some embodiments, step (b) further comprises allowing the multi-phase system and the mammalian blood sample to naturally settle to its thermodynamically stable state. As a result, the erythrocytes will settle to a location in the MPS characteristic of its density, e.g., below the second phase. In other embodiments, step (b) comprises centrifuging the multi-phase system and the mammalian blood sample. The use of centrifuge facilitates the settlement process. The multi-phase system and the mammalian blood sample may be centrifuged for about 1, 2, 3, 4, 5, 6, 7, 8, 9, 10, 15, or 30 min. When the centrifuging process is conducted only for a short period of time, e.g., about 1, 2, 3, 4, or 5 min, the analyte in the blood sample may not have reached its thermodynamic state in the MPS. In some embodiments, the centrifuging process is stopped while the erythrocytes still migrating through the phases in the MPS. Such shorter centrifuge may reveal the size or shape profile of the erythrocytes with the same density as erythrocytes with different sizes or shapes that may have different settlement rates in the MPS.

In some embodiments, the presence or absence of erythrocytes is observed by the naked eye or digital quantification analysis. In some embodiments, the volume ratio of the mammalian blood sample to the multiphase system is about 4:1, 2:1, 1:1, 1:2, 1:3, 1:4, 1:5, or 1:6, or 0.15-4:1, or 0.2-2:1, or 0.3-1:1. Ranges bounded by any of the specific values noted above are also contemplated.

In yet another aspect, a kit for the diagnosis of sickle cell disease using a multi-phase system comprising:
a) at least a first and second phase components each comprising at least one polymer; and
b) instructions for:
(i) combining the first and second phase components and water, each in a predetermined amount, to create a multi-phase system described herein, wherein multiple phases phase-separate to form an interface between the first and second phases; and
(ii) adding a mammalian blood sample to the multi-phase system to allow the erythrocytes to migrate to a location(s) characteristic of their densities; and
(iii) observing the presence or absence of erythrocytes below the second phase;
wherein the presence of erythrocytes below the second phase indicates sickle cell disease.

In yet another aspect, a kit for the diagnosis of subtypes of sickle cell disease is described, comprising:
a) at least a first, second, and third phase components each comprising at least one polymer; and
b) instructions for:
(i) combining the first, second, and third phase components and water, each in a predetermined amount, to create a multi-phase system described herein, wherein the multiple phases phase-separate to form interfaces between the first and third phases and between the third and second phases; and
(ii) adding a mammalian blood sample to the multi-phase system to allow the erythrocytes to migrate to a location(s) characteristic of their densities;
(iii) observing the presence or absence of erythrocytes at the interfaces;
wherein
the presence of erythrocytes below the second phase indicates sickle cell disease;
the pattern that the amount of erythrocytes present at the interface of the first and third phases is more than the amount of erythrocytes present at the interface of the third and second phases indicates homozygous sickle cell disease (Hb SS); and
the pattern that the amount of erythrocytes present at the interface of the third and second phases is about the same or more than the amount of erythrocytes present at the interface of the first and third phases indicates hemoglobin sickle cell disease (Hb SC).

In some embodiments, the kit includes the phase component of each phase in its pure chemical state. The kit may include water or instructions to mix a predetermined amount of water with predetermined amounts of the first and second phase components. In other embodiments, the kit may include stock solutions of the first and second phases with the first and second phase components already dissolved and instructions on how to dilute the stock solutions to obtain the desired first and second phases.

Blood is a complex mixture of many types of cells and each type can be divided into subtypes. In sickle cell disease, the presence of dense, sickled cells provide a diagnostic marker for the disease. This application demonstrates a density-based separation of red blood cells in a system of aqueous multiphase polymers that enables a visual test that identifies sickle cell disease, starting from samples of whole blood, in less than 12 minutes. This low-cost, simple test could provide a means to enable diagnosis of sickle cell disease in low-resource settings, and enable life-saving interventions for children with the disease. The method itself provides a demonstration of the use of a biophysical indicator (here, density) rather than a biochemical marker (e.g., proteins separated by gel electrophoresis) as a means to do point-of-care hematology.

In any of the above-described embodiments, the kit comprising the multiphase system described herein further comprises a first tube holding the multiphase system. In some specific embodiments, the first tube has a small hole for wicking blood or other liquid containing cells of interest into the first tube. The kit may further include a sleeve slidable along the first tube to be configured to cover the hole after the blood or other liquid containing cells of interest is introduced into the first tube. The sleeve may be made from any suitable material known in the art. In some specific embodiments, the sleeve is made from rubber, e.g., silicone rubber. The sleeve may prevent any liquid from leaking from the first tube during operation, e.g., centrifugation. In other specific embodiments, a second tube smaller than the first tube is used. The second tube has a hole therein for wicking blood or other liquid containing cells of interest into the second tube. Once the blood or liquid is introduced into the second tube, the second tube may be dropped into the first tube to allow the blood or the liquid to drip into the first tube for analysis or separation. The second tube may have a fixed capacity to hold liquid and thus the volume of liquid to be introduced into the first tube is consistent. The second tube may also contain a ring at its peripheral to prevent the second tube from completely dropping into the first tube.

In any of the above-described embodiments, the kit provides a point-of-care test which is low-cost, quick, and efficient. In rural settings, patients may travel for a day to seek medical care, and follow-up is challenging. Tests that can be coupled to actionable information and counseling must be rapid (ideally under 30 minutes). In some embodiments described herein, very little amount (~5 μL) of blood (a volume easily obtained from a finger stick) is needed for assays using the kit and the test usually takes about 10 minute or less. The cost per test is trivial, e.g., ~$0.50 (Table 5) and is particularly attractive for uses in places with limited resources.

In some embodiments, a density-adjusting agent may be used to adjust (e.g., increase) or optimize the density of the phases in the MPS described herein. Non-limiting examples of the density-adjusting agents include Nycodenz. Other density-adjusting agents may be used. In some embodiments, the pH of the phases in the MPS is adjusted to be in the range of physiological range, e.g., 7.3-7.5. A buffer agent such as PBS can be used.

In any of the embodiments described herein, the one or more phases in the MPS may further comprise an additive selected from the group consisting of a salt, a buffering agent, a miscible surfactant, a co-solvent, an acid, a base, a miscible polymer, vitamin, drug, antibiotic, small molecule, dye, colloid, and flurophore.

Section 4. Experimental Results

Materials. We purchased the following polymers: poly (ethylene glycol) (Sigma-Aldrich; MW=20000 Da), Ficoll (Sigma-Aldrich; MW=70000 Da and 400000 Da), dextran (Spectrum Chemical; 500000 Da), and poly(vinyl alcohol) (Polysciences; MW=3000 Da). We purchased phosphate-buffered saline (Lonza) at 10× concentration and diluted it to 1× using distilled, deionized water from a Milli-Q water purification system (Millipore). For stains, we used New Methylene Blue for slides and ReticONE (acridine orange) for flow cytometry. We used all reagents without further purification. We purchased Lymphoprep from Accurate Chemical, fluorescein isothiocyanate from Thermo Scientific, and Percoll from GE healthcare. For the parasite culture media, we purchased RPMI, hypoxanthine and sodium bicarbonate from Sigma, HEPES from EMD Biosciences, and Albumax from Invitrogen.

We purchased human whole blood, collected over sodium heparin as an anticoagulant, from single healthy donors (vendor certified syphilis−, HTLV−, HIV−, HepB−, and HepC−) from Research Blood Components (Boston, Mass.). Whole blood units (approximately 500 mL in volume) collected from hemochromatosis patients undergoing therapeutic phlebotomy were obtained from the blood donor center at Brigham and Women's Hospital, Boston, Mass.

The H Strain of *Plasmodium knowlesi* was obtained from the Biomedical Primate Research Center (Rijswijk, The Netherlands). The 3D7 Strain of *Plasmodium falciparum* was obtained from the Harvard School of Public Health (Boston, Mass.).

Formation and Analysis of AMPSs.

We prepared stock solutions of polymers at concentrations higher than those used in applications of aqueous multiphase systems (AMPSs) using a calibrated balance and a volumetric flask. Depending on the application, buffer salts or NaCl may be added to the stock solution. Measurements of density characterized stock solutions and to ensure uniformity across multiple preparations of each solution. To prepare AMPSs, we added solutions of polymers (either at stock concentrations or a dilution) into a container (e.g., conical tubes), thoroughly mixed the solutions by vortex for 30 seconds, and accelerated phase separation by centrifugation. Phase separation in AMPSs due to gravity alone may occur inconveniently slowly (hours) because the difference in density between layers of an AMPS can be small ($\Delta\rho \approx 0.001$-$0.100$ g cm$^{-3}$). Centrifugation (2-30 minutes at 2000 g) increased the rate of separation of phases in AMPSs.

All of our AMPS included 5 mM sodium phosphate monobasic and 5 mM sodium phosphate dibasic to buffer the system. The pH was measured with a gel probe electrode and standard pH meter (Orion Star, Thermo Scientific). We adjusted the pH of all samples to 7.40±0.02 by titrating NaOH and HCl. We also included 5 mM disodium ethylenediaminetetraacetic acid (EDTA) to prevent coagulation.

We removed an aliquot of each phase (ca. 800 μL) in order to analyze the density of each layer by oscillating U-tube densitometry (Anton Paar DM35N). For experiments using blood, the final osmolalities of the phases of an AMPS are important to ensure biocompatibility. We measured osmolality by vapor pressure osmometry using a Vapro 5500 (Wescor). To adjust osmolality, we added NaCl.

Separations of Blood with AMPS.

We performed separation experiments within one week of the blood being drawn. Blood was stored at 4° C. and brought to room temperature before use. We introduced the blood to the top phase of the AMPS as a layer in all of our experiments. Samples were spun at 4000 g for one hour at a temperature of 32° C.

DC-Percoll Separations.

To compare our enrichment method to a standard technique, we used a standard density separation with Percoll. Centrifugation of hemochromatosis blood in 50 mL tubes at 4000 g for one hour packed cells. After removing the serum, the top 4 mL of packed blood was collected and resuspended in the previously collected serum at ~50% hematocrit. We layered 5 mL of this blood on top of 6 mL of 70% isotonic Percoll. Centrifugation for 15 minutes at 1200 g at 30° C. in a swinging bucket rotor (SX4750A, Beckman Coulter) left a band of erythrocytes above the Percoll and a pellet of erythrocytes at the bottom. A pipette collected the band from above the Percoll. Washing the collected samples with PBS three times removed excess Percoll before analysis and the introduction of parasites.

Characteristics of Blood Samples Used.

We used blood from two sources: a commercial supplier (Research Blood Components) and a hematology clinic (Brigham and Women's Hospital, Boston). The blood from the commercial supplier was collected with an anti-coagulant from normal, healthy individuals. The blood from the hematology clinic came from hemochromatosis patients undergoing treatment. Despite the hemochromatosis, the blood from many of these patients did not reveal a level of reticulocytes that was significantly higher than normal. In this work, all the blood that was used contained the clinically normal range of 0.5-2.5% reticulocytes before enrichment. White blood cells were removed from the blood prior to use by passage through a leukocyte filtration device (Sepacell R-500). The removal of white blood cells is necessary for the cultivation of *Plasmodium* parasites.

Extraction of Fractions of Cells after Separation.

For separations on whole blood performed in conical tubes with AMPS, blood enriched for reticulcoytes concentrated at the liquid/liquid interface. After blunting a pipette, we removed the clumps of packed red cells that could be seen by the eye at this interface. Depending on the yield and the tube used, the total volume extracted ranged from 100 μL, to 1 mL. 5 μL of packed cells from the pellet at the bottom of the tube were also collected for analysis.

For screening experiments, washing extracted cells in roughly a five-fold volume of isotonic PBS a total of three times removed excess polymers for analysis (i.e., microscopy on thin smears or flow cytometry). During each wash, we suspended the cells gently with a pipette and then spun the cells to a pellet at 1,500 g for 6 minutes. After the supernatant was removed, the cells were suspended again until all washes were completed. For invasion experiments, increasing the volume of PBS to be 20-fold the volume of the sample provided a more thorough washing to remove excess polymers.

Analysis of the Fractions of Blood.

We counted reticulocytes by flow cytometry (MACS Quant). Reticulocytes were stained with acridine orange (Retic ONE) following the manufacturer's protocol. Using known volumes of sample, we counted cells and also quantified the fraction of all cells that were reticulocytes. Comparing samples before and after enrichment allowed us to estimate the total number of reticulocytes that were added to each AMPS, and the total number of reticulocytes recovered. The fraction of these two numbers provided a measure of the yield of reticulocytes.

We also made thin smears stained with New Methylene Blue (Retic Stain) and quantified reticulocytemia by microscopy. To analyze other cell parameters, we used a hematology analyzer (Advia 2120, Siemens).

Statistical Methods.

We used a two-sided Student's T-test to test for significant differences between the logarithms of the means of the parasitized erythrocyte multiplication rates (PEMRs) for different conditions.

Selection of AMPSs.

The dextran-Ficoll AMPS exhibited a small difference in density between the top and bottom phases. Without additives, dextran-Ficoll AMPSs prepared in distilled, deionized water that are in the density range of blood cells are acidic and hypotonic. We titrated the pH to 7.40 with NaOH and HCl. We added NaCl to the solutions to reach a final osmolality of 295±15 mOsm kg$^{-1}$ (i.e., isotonic).

The poly(ethylene glycol)-dextran AMPS had similar characteristics to the poly(ethylene glycol)-Ficoll AMPS. The poly(vinyl alcohol)-poly(ethylene glycol) AMPS could not produce a bottom phase that was dense enough to separate most reticulocytes from mature erythrocytes in the range of osmolality that is required for the separation of cells.

Centrifugation Parameters.

Our separations used swinging-bucket rotors for centrifugation to avoid smearing cells along the walls of centrifuge tubes during sedimentation. Centrifugation at a relative centrifugal force (RCF) of 4000 g for one hour provided a clear separation between blood cells at the liquid/liquid interface of the two-phase AMPS and cells below the bottom phase for a sedimentation distance of 40 mm (e.g., 4 mL of AMPS in a 15 mL conical tube) (FIG. 1). Experiments with a greater distance for sedimentation (e.g., 60 mm for 25 mL blood over 25 mL AMPS in a 50 mL conical tube) required additional centrifugation time. For larger volumes that had up to a 50% increase in the sedimentation distance (i.e., 25 mL of AMPS in a 50 mL conical tube) the centrifugation time was increased to 90 minutes. The limitation of a long period of centrifugation can be overcome by using a centrifuge that operates at higher relative centrifugal forces.

Chemicals.

We purchased the following polymers: poly(ethylene glycol) (Sigma-Aldrich; MW=20000 Da), Ficoll (Sigma-Aldrich; MW=70000 Da and 400000 Da), dextran (Spectrum Chemical; 500000 Da), and poly(vinyl alcohol) (PVA) (Polysciences; MW=3000 Da)—formed by hydrolyzing 75% of poly(vinyl acetate). Solutions of AMPS contained the following chemicals: ethylenediaminetetra-acetic acid disodium salt (EDTA) (Sigma-Aldrich), potassium phosphate monobasic (EMD), sodium phosphate dibasic (Mallinkrodt AR), sodium chloride (EMD), MgCl$_2$ (USB), and Nycodenz (Axis-Shield PoC). We used a Hemacolor Stain Kit (Harelco) to stain slides of thin smears of blood. For the nystatin treatment, we purchased the following additional chemicals: nystatin (*Streptomyces noursei*, Calbiochem), choline chloride (Sigma-Aldrich), tris(hydroxymethyl)aminomethane hydrochloride (Tris HCL, Bethesda Research Laboratories), 3-(N-morpholino) propane-sulfonic acid (MOPS, EM Science), potassium chloride (EMD), sucrose (EMD), glucose (Sigma-Aldrich), albumin from bovine serum (Sigma-Aldrich), and sodium phosphate monobasic (Mallinkrodt Chemicals).

Blood Samples.

Children's Hospital Boston (CHB) and the Sickle Cell Center of Southern Louisiana (SCCSL) (New Orleans) provided de-identified blood samples with known hemoglobin genotypes. We tested our system on a variety of blood samples that were Hb AA, Hb AS, Hb SS, Hb SC, and Hb S-β+. The Hb SS samples varied in their Hb F content and their proportion of dense sickled cells. We used de-identified blood from Research Blood Components in Boston for our model sickle blood systems.

At the SCCSL, blood samples were collected into 4 mL Vacutainer tubes (K2EDTA, BD, Franklin Lakes, N.J.) during routine blood draws from patients with informed consent, according to a protocol approved by Tulane University Biomedical IRB. At CHB, blood samples were collected when clinically indicated and discarded samples were used according to a protocol approved by Children's Hospital Boston IRB.

Three normal controls were obtained from consented volunteers at Harvard University under a protocol approved by the Committee on the Use of Human Subjects at Harvard University.

Materials for Rapid Tests.

We purchased the following materials to make our rapid tests: heparinized, polycarbonate microhematocrit tubes (Iris Sample Processing), clay seals (Critoseal, Leica), silicone rubber tubing with an inner diameter of 1.02 mm and an outer diameter of 2.06 mm (Helix Mark, Helix Medical), and five-minute epoxy.

Preparation of AMPS.

To prepare each AMPS, we added polymers, buffer salts, and other additives (i.e., Nycodenz and EDTA) in volumetric flasks and added deionized water to attain the final volume. Adjustments to pH and osmolality were made as described in the manuscript. A vortexer or magnetic stir bar mixed solutions thoroughly.

In our AMPS, we include 5 mM EDTA and 1 mM MgCl$_2$ to help preserve the blood and prevent coagulation. The tubes are also heparinized. We have varied the amount of these additives but we have been unable to completely eliminate the clotting platelets.

Characterization.

We measured density with a density meter (DM50, Anton Paar), osmolality with a vapor pressure osmometer (Vapro 5500, Wescor), and pH with a pH meter (Orion 2 Star, Thermo Scientific). Complete blood counts were done on a hematology analyzer (ADVIA 2120, Siemens).

Rapid Test Fabrication.

We used a 3D printer (Fortus 250 mc, Stratasys) to print a holder to punch reproducible holes in the sides of the microhematocrit tubes. The holder was designed with AutoCAD (AutoDesk). We load each holder with microhematocrit tubes and use standard metal pushpins (Staples) to punch holes in the sides of the tubes at the prescribed length. We also used fine tipped markers to mark a fixed point on the length of the tubes as fill lines to hold the prescribed volume of the AMPS. After removing the tubes from the holder, we blew out any loose plastic with an air gun. We cut small lengths of silicone tubing (3-5 mm) and slid them over the tubes to cover the holes in their sides. While an AMPS was being stirred by a magnetic stir plate, we used a micropipettor to fill the marked tubes up to the fill lines and then sealed them with either white sealing clay or epoxy. The completed tests were then used on blood samples as described in the manuscript.

For larger productions, we estimated the costs necessary to cap and more permanently seal the tubes with glue as well as labor, equipment, and packaging costs (Table 5). Time estimates were based on current manufacturing procedures in the laboratory and materials costs were based on the volumes at which we currently purchased materials and chemicals. With these parameters, the cost per test is $0.50. Production in a market with lower labor costs and with bulk chemical prices should reduce this cost.

A. Enrichment of Reticulocytes

Each phase of an AMPS consists predominantly (60-95% (w/v)) of water, and contains concentrations of polymers ranging from 1-40% (w/v) (that is, micromolar to millimolar). These compositions determine the physical properties of the phases of an AMPS (e.g., density, viscosity, ionic strength, and refractive index). The phases order, on settling or on centrifugation, according to their densities. Many AMPSs are biocompatible and have been used for separations of cells by partitioning—that is, by a process based on the preferential interaction of the surfaces of different types of cells for the components of the different phases. Partitioning methods result in relatively low enrichment of reticulocytes (<2%).

The differences in the densities of the phases of AMPSs provide a means to perform density-based separations. The interfaces between phases mark discontinuities (on the molecular scale) between continuous fluid phases of different density. The densities ($\rho_A$ and $\rho_B$) of the phases above and below the interface establish the range of densities for components ($\rho_C$) that will localize at the interface ($\rho_A > \rho_C > \rho_B$). The interfacial surface energy between the phases of an AMPSs is astonishingly low (from nJ m$^{-2}$ to mJ m$^{-2}$); a low interfacial surface energy reduces the mechanical stress on cells as they pass through the interface.

Compared to layered gradients in density (e.g., Percoll, Optiprep, or Nycodenz), AMPSs offer several advantages: i) they are thermodynamically stable, ii) they self-assemble rapidly (t~15 minutes, 2000 g) on centrifugation or slowly (t~24 hours) on settling in a gravitational field, iii) they can differentiate remarkably small differences in density ($\Delta\rho < 0.001$ g cm$^{-3}$), and iv) they provide well-defined interfaces that facilitate both the identification and extraction of sub-populations of cells by concentrating them to quasi-two-dimensional surfaces.

This application describes a new method to obtain samples of cells that are enriched for reticulocytes using centrifugation through aqueous multiphase systems (AMPSs). AMPSs are systems of polymers in aqueous solutions that generate immiscible phases when mixed. These phases provide self-assembling step-gradients in density. It is demonstrated that centrifugation through AMPSs separates cells based on their density, and concentrates them at interfaces. *P. knowlesi* multiplies at a higher rate in reticulocytes enriched by this method than in normal human blood. We exploit two differences between reticulocytes and mature erythrocytes—density and osmotic response to hypotonic and hypertonic environments—to enrich reticulocytes from whole blood to an enhanced reticulocytemia of 64±3%.

AMPSs can Enrich Reticulocytes to a High Purity.

Upon sedimentation of 1 mL of blood through 4 mL of a hypertonic ($\phi=330$ mOsm kg$^{-1}$) AMPS of 11.6% (w/v) of dextran and 11.6% (w/v) Ficoll ($\rho_{top}=1.086$ g cm$^{-3}$ and $\rho_{bottom}=1.089$ g cm$^{-3}$), two layers of erythrocytes were observed: one layer at the liquid/liquid interface between the two phases of the AMPS and one layer between the bottom phase and the container (FIG. 1). After extracting cells with a pipette and washing them in phosphate buffered saline (PBS), cells were stained either with New Methylene Blue (to visualize intracellular RNA in reticulocytes by microscopy) or with acridine orange (to quantify reticulocytes by flow cytometry).

Figure 2:
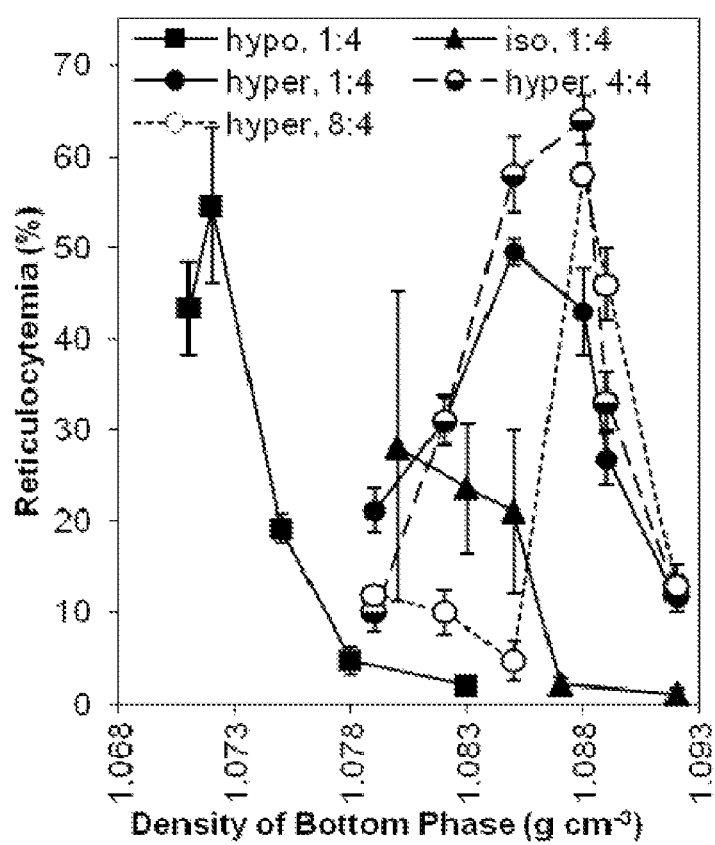
FIG. 2 illustrates the fraction of blood at the interface of several AMPSs which are enriched to a reticulocytemia over 50%.

For hypertonic, isotonic, and hypotonic systems, we found specific densities of the dextran-Ficoll AMPS that provided highly enriched reticulocytes (FIG. 2, FIG. 7). Table 1 details the parameters of each AMPS and the results of each enrichment procedure. For small shifts in osmality, the difference in density between an object and water scales with the osmolality (Supporting Information for Enrichment of Reticulocytes); the density of the best-performing hypotonic system is lower than that of the best-performing hypertonic system. A hypotonic ($\phi=269$ mOsm kg$^{-1}$) AMPS of 9.3% (w/v) dextran and 9.3% (w/v) Ficoll with $\rho_{top}=1.068$ g cm$^{-3}$ and $\rho_{bottom}=1.072$ g cm$^{-3}$ enriched reticulocytes to 55±8% at the interface of the AMPS (FIG. 2). Although this system provided the highest purity of enrichment for a 1:4 volume ratio, it collected less than 10$^7$ cells (~1 μL of packed cells) at the interface.

Different volume ratios of blood to AMPSs were also explored to see if similar purities could be obtained with a lower relative volume of AMPSs (Table 4). A 1:1 volume ratio of blood to a hypertonic ($\phi=336$ mOsm kg$^{-1}$) AMPS of 11.4% (w/v) dextran and 11.4% (w/v) Ficoll ($\rho_{top}=1.084$ g cm$^{-3}$ and $\rho_{bottom}=1.088$ g cm$^{-3}$) provided the greatest enrichment of reticulocytes (up to 64±3%) at the interface of the AMPS (FIG. 2, FIG. 7).

Variations between individuals can lead to significant differences in the performance of density-based separation methods. Reticulocytes were enriched using four dextran-Ficoll AMPSs from the initial screen, and blood from four to seven different donors (Table 1). Increasing the ratio of the volume of blood to polymer to 1:1 (i.e., 4 mL blood on 4 mL of AMPS) increased the yield of reticulocytes as measured by flow cytometry (Supporting Information for Enrichment of Reticulocytes).

The degree of enrichment and final yield varied significantly between donors (Table 2). The last three AMPSs from Table 1 demonstrate, however, that similar enrichments can be achieved between systems with different tonicities. The density of these systems increases as a function of osmolality, reflecting the increase in the mean density of the reticulocyte and mature erythrocyte populations. Interestingly, in the systems with similar enrichments, the median yield is two times greater in the hypertonic AMPS than in the isotonic AMPS; it is more than 70 times greater in the isotonic AMPS than in the hypotonic AMPS. We also compared our systems to a common enrichment method: differential centrifugation of blood followed by centrifugation of the enriched fraction over a layered gradient of Percoll (DC-Percoll). Our hypertonic systems provide a higher median yield, and their ranges for reticulocytemia and reticulocyte yield are smaller than blood enriched by DC-Percoll. Separations with AMPS provide better reproducibility than DC-Percoll.

Malaria Parasites Invade Reticulocytes Enriched by Centrifugation Through an AMPS.

To ensure that we obtained a sufficient number of reticulocytes to perform an invasion assay after enrichment, we chose system C1 (Table 1). We layered 25 mL of blood over 25 mL of the dextran-Ficoll AMPS in 50 mL conical tubes. After centrifugation, we collected the cells from the interface using sterile technique and washed them three times in a 100-fold volume of PBS. After washing, the morphology of the cells was comparable to the morphology before exposure to AMPS (Table 3, FIG. 8); these cells were then used for culture. Table 4 details the reticulocytemia of enrichments from different donors. We added purified late-stage parasites (e.g., late trophozoites and schizonts) of $P.$ $knowlesi$ H strain to the culture medium at a parasitemia—the percentage of erythrocytes that contain parasites—between 0.5-2.5%. This mixture of enriched reticulocytes and parasites incubated at culture conditions for 18 hours. This time is sufficient to allow late-stage parasites to mature and rupture, and then to release infectious merozoites into the suspension of erythrocytes enriched in reticulocytes.

We quantified the ability of parasites to reinvade by the parasitized erythrocyte multiplication rate (PEMR)—the ratio of the initial parasitemia to the parasitemia after 18 hours. If merozoites can invade the AMPS-enriched reticulocytes, we would expect to see an increase in the parasitemia after 18 hours (PEMR>1); a PEMR>1 is necessary for long-term cultivation of malaria parasites. Reinvasion is an important step in culture that depends in part on the surface of the host cells; if residual polymers on the surface of reticulocytes compromised cultivation, we expected the effect would be most pronounced during reinvasion.

Figure 3:
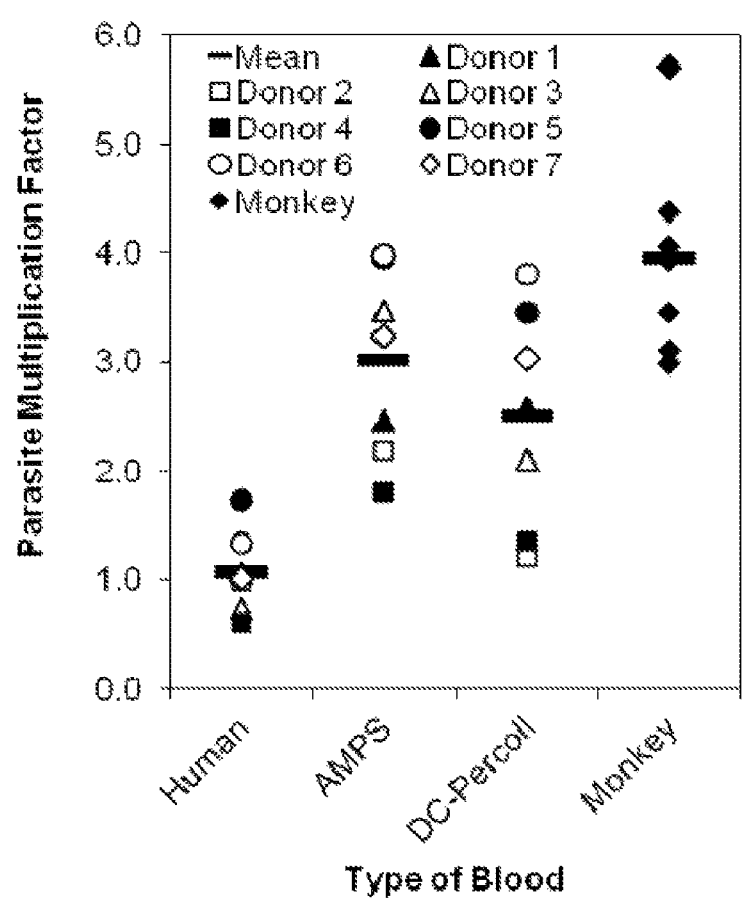
FIG. 3 illustrates that reticulocytes enriched through a dextran-Ficoll AMPS are invaded by *P. knowlesi*.

FIG. 3 shows the results from invasion assays using blood enriched by AMPS as well as results from similar invasion assays using normal human blood, blood enriched for reticulocytes by DC-Percoll, and blood from rhesus monkeys—the well-established experimental host for $P.$ $knowlesi$. In normal human blood, the PEMR was often less than one because $P.$ $knowlesi$ H strain is limited to invasion of human reticulocytes and young erythrocytes. Blood enriched by DC-Percoll provides a benchmark comparison for reticulocyte enrichment. For each invasion assay, we matched the enrichment of reticulocytes from DC-Percoll with that from AMPSs by diluting the more enriched sample with whole blood. Reticulocytemia in enriched samples was between 4-21%. Blood from a rhesus monkey provided a positive control in which multiplication of parasites was unrestricted by the availability of host cells.

Blood from seven subjects provided biological replicates. We performed three technical replicates with each subject. We prepared thin smears of the samples immediately after the introduction of late stage parasites to the blood samples and at 18 hours after cultivation. After staining the slides with Field's Stain, we quantified the parasitemia of each sample (Supporting Information for Enrichment of Reticulocytes).

As expected, the multiplication rate in rhesus blood was greater than any of the human samples (FIG. 3). The enriched blood from both AMPSs and DC-Percoll performed better than normal blood to support the invasion of $P.$ $knowlesi$. On average, the PEMR in blood enriched by AMPSs was 2.9 times that of normal blood (p-value <0.01). Microscopy confirmed that the parasites that had invaded the reticulocyte-rich blood from AMPSs continued to develop normally in culture. The average PEMR in blood enriched by AMPSs was 1.3 times that of blood enriched by DC-Percoll, but the difference was not significant (p-value=0.29).

We have demonstrated that sedimentation through AMPSs is a useful technique to separate cells by density. AMPSs concentrate cells at molecularly sharp interfaces that provide well-defined steps in density, and this concentration facilitates the enrichment of cell types that differ in density. Specifically, AMPSs can enrich reticulocytes from human whole blood. $P.$ $knowlesi$ H strain invades blood enriched for reticulocytes by AMPSs at a higher rate than it invades normal blood. This blood enriched in reticulocytes should enable the culture of malaria species that preferentially invade reticulocytes (i.e., $P.$ $vivax$, $P.$ $knowlesi$, and $P.$ $ovale$).

Existing methods to enrich reticulocytes are not suitable for the routine enrichments that would be required for a sustainable continuous culture. Differential centrifugation provides a simple method to enrich reticulocytes, but the enrichment is low (<3%). Affinity-based separation techniques and the direct growth of reticulocytes allows high purity (>90%) that is not matched by enrichments using AMPSs, but these methods are expensive and impractical for routine use. Performing differential centrifugation followed by centrifugation over a layered gradient of Percoll provides a means to enrich reticulocytes, but this method requires two separate centrifugation steps and two extraction steps; variation between steps compound to reduce reproducibility. Exposure to Percoll may also impair parasite development for specific strains of malaria parasites.

Enriching reticulocytes through AMPSs retains the simplicity of differential centrifugation (layering blood over an AMPS adds only one step to the general procedure), but provides much higher levels of enrichment (median reticulocytemia of 19%). The scalability of AMPSs also allows researchers to process large volumes (~1 L) of blood in a single centrifugation step. The combination of purity, scalability, and simplicity make centrifugation through AMPSs a valuable technique for separations of cells that require high throughput and routine use. The use of AMPSs to separate cells by density should aid in the cultivation of malaria species that require reticulocyte-rich blood, and facilitate the separation of other cells with natural differences in density such as lymphocytes and erythrocytes, as well as sickled erythrocytes and normal erythrocytes.

Supporting Information for Enrichment of Reticulocyte
  Materials.
  We purchased the following polymers: poly(ethylene glycol) (Sigma-Aldrich; MW=20000 Da), Ficoll (Sigma-Aldrich; MW=70000 Da and 400000 Da), dextran (Spectrum Chemical; 500000 Da), and poly(vinyl alcohol) (Polysciences; MW=3000 Da). We purchased phosphate-buffered saline (Lonza) at 10× concentration and diluted it to 1× using distilled, deionized water from a Milli-Q water purification system (Millipore). For stains, we used New Methylene Blue for slides and ReticONE (acridine orange) for flow cytometry. We used all reagents without further purification. We purchased Lymphoprep from Accurate Chemical, fluorescein isothiocyanate from Thermo Scientific, and Percoll from GE healthcare. For the parasite culture media, we purchased RPMI, hypoxanthine and sodium bicarbonate from Sigma, HEPES from EMD Biosciences, and Albumax from Invitrogen.

We purchased human whole blood, collected over sodium heparin as an anticoagulant, from single healthy donors (vendor certified syphilis⁻, HTLV⁻, HIV⁻, HepB⁻, and HepC⁻) from Research Blood Components (Boston, Mass.). Whole blood units (approximately 500 mL in volume) collected from hemochromatosis patients undergoing therapeutic phlebotomy were obtained from the blood donor center at Brigham and Women's Hospital, Boston, Mass.

The H Strain of *Plasmodium knowlesi* was obtained from the Biomedical Primate Research Center (Rijswijk, The Netherlands). The 3D7 Strain of *Plasmodium falciparum* was obtained from the Harvard School of Public Health (Boston, Mass.).

Formation and Analysis of AMPSs.

We prepared stock solutions of polymers at concentrations higher than those used in applications of aqueous multiphase systems (AMPSs) using a calibrated balance and a volumetric flask. Depending on the application, buffer salts or NaCl may be added to the stock solution. Measurements of density characterized stock solutions and to ensure uniformity across multiple preparations of each solution. To prepare AMPSs, we added solutions of polymers (either at stock concentrations or a dilution) into a container (e.g., conical tubes), thoroughly mixed the solutions by vortex for 30 seconds, and accelerated phase separation by centrifugation. Phase separation in AMPSs due to gravity alone may occur inconveniently slowly (hours) because the difference in density between layers of an AMPS can be small ($\Delta\rho \approx 0.001$-$0.100$ g cm$^{-3}$). Centrifugation (2-30 minutes at 2000 g) increased the rate of separation of phases in AMPSs.

All of our AMPS included 5 mM sodium phosphate monobasic and 5 mM sodium phosphate dibasic to buffer the system. The pH was measured with a gel probe electrode and standard pH meter (Orion Star, Thermo Scientific). We adjusted the pH of all samples to 7.40±0.02 by titrating NaOH and HCl. We also included 5 mM disodium ethylenediaminetetraacetic acid (EDTA) to prevent coagulation.

We removed an aliquot of each phase (ca. 800 µL) in order to analyze the density of each layer by oscillating U-tube densitometry (Anton Paar DM35N). For experiments using blood, the final osmolalities of the phases of an AMPS are important to ensure biocompatibility. We measured osmolality by vapor pressure osmometry using a Vapro 5500 (Wescor). To adjust osmolality, we added NaCl.

Separations of Blood with AMPS.

We performed separation experiments within one week of the blood being drawn. Blood was stored at 4° C. and brought to room temperature before use. We introduced the blood to the top phase of the AMPS as a layer in all of our experiments. Samples were spun at 4000 g for one hour at a temperature of 32° C.

DC-Percoll Separations.

To compare our enrichment method to a standard technique, we used a standard density separation with Percoll. Centrifugation of hemochromatosis blood in 50 mL tubes at 4000 g for one hour packed cells. After removing the serum, the top 4 mL of packed blood was collected and resuspended in the previously collected serum at ~50% hematocrit. We layered 5 mL of this blood on top of 6 mL of 70% isotonic Percoll. Centrifugation for 15 minutes at 1200 g at 30° C. in a swinging bucket rotor (SX4750A, Beckman Coulter) left a band of erythrocytes above the Percoll and a pellet of erythrocytes at the bottom. A pipette collected the band from above the Percoll. Washing the collected samples with PBS three times removed excess Percoll before analysis and the introduction of parasites.

Characteristics of Blood Samples Used.

We used blood from two sources: a commercial supplier (Research Blood Components) and a hematology clinic (Brigham and Women's Hospital, Boston). The blood from the commercial supplier was collected with an anti-coagulant from normal, healthy individuals. The blood from the hematology clinic came from hemochromatosis patients undergoing treatment. Despite the hemochromatosis, the blood from many of these patients did not reveal a level of reticulocytes that was significantly higher than normal. In this work, all the blood that was used contained the clinically normal range of 0.5-2.5% reticulocytes before enrichment. White blood cells were removed from the blood prior to use by passage through a leukocyte filtration device (Sepacell R-500). The removal of white blood cells is necessary for the cultivation of *Plasmodium* parasites.

Extraction of Fractions of Cells after Separation.

For separations on whole blood performed in conical tubes with AMPS, blood enriched for reticulcoytes concentrated at the liquid/liquid interface. After blunting a pipette, we removed the clumps of packed red cells that could be seen by the eye at this interface. Depending on the yield and the tube used, the total volume extracted ranged from 100 µL to 1 mL. 5 µL of packed cells from the pellet at the bottom of the tube were also collected for analysis.

For screening experiments, washing extracted cells in roughly a five-fold volume of isotonic PBS a total of three times removed excess polymers for analysis (i.e., microscopy on thin smears or flow cytometry). During each wash, we suspended the cells gently with a pipette and then spun the cells to a pellet at 1,500 g for 6 minutes. After the supernatant was removed, the cells were suspended again until all washes were completed. For invasion experiments, increasing the volume of PBS to be 20-fold the volume of the sample provided a more thorough washing to remove excess polymers.

Analysis of the Fractions of Blood.

We counted reticulocytes by flow cytometry (MACS Quant). Reticulocytes were stained with acridine orange (Retic ONE) following the manufacturer's protocol. Using known volumes of sample, we counted cells and also quantified the fraction of all cells that were reticulocytes. Comparing samples before and after enrichment allowed us to estimate the total number of reticulocytes that were added to each AMPS, and the total number of reticulocytes recovered. The fraction of these two numbers provided a measure of the yield of reticulocytes.

We also made thin smears stained with New Methylene Blue (Retic Stain) and quantified reticulocytemia by microscopy. To analyze other cell parameters, we used a hematology analyzer (Advia 2120, Siemens).

Statistical Methods.

We used a two-sided Student's T-test to test for significant differences between the logarithms of the means of the parasitized erythrocyte multiplication rates (PEMRs) for different conditions.

Experimental Details

Selection of AMPSs.

The dextran-Ficoll AMPS exhibited a small difference in density between the top and bottom phases. Without additives, dextran-Ficoll AMPSs prepared in distilled, deionized water that are in the density range of blood cells are acidic and hypotonic. We titrated the pH to 7.40 with NaOH and HCl. We added NaCl to the solutions to reach a final osmolality of 295±15 mOsm kg$^{-1}$ (i.e., isotonic).

The poly(ethylene glycol)-dextran AMPS had similar characteristics to the poly(ethylene glycol)-Ficoll AMPS. The poly(vinyl alcohol)-poly(ethylene glycol) AMPS could not produce a bottom phase that was dense enough to separate most reticulocytes from mature erythrocytes in the range of osmolality that is required for the separation of cells.

Centrifugation Parameters.

Our separations used swinging-bucket rotors for centrifugation to avoid smearing cells along the walls of centrifuge tubes during sedimentation. Centrifugation at a relative centrifugal force (RCF) of 4000 g for one hour provided a clear separation between blood cells at the liquid/liquid interface of the two-phase AMPS and cells below the bottom phase for a sedimentation distance of 40 mm (e.g., 4 mL of AMPS in a 15 mL conical tube) (FIG. 1). Experiments with a greater distance for sedimentation (e.g., 60 mm for 25 mL blood over 25 mL AMPS in a 50 ml, conical tube) required additional centrifugation time. For larger volumes that had up to a 50% increase in the sedimentation distance (i.e., 25 mL of AMPS in a 50 mL conical tube) the centrifugation time was increased to 90 minutes. The limitation of a long period of centrifugation can be overcome by using a centrifuge that operates at higher relative centrifugal forces.

Detailed Results from Enrichment of Reticulocytes from Whole Blood.

Figure 4A:
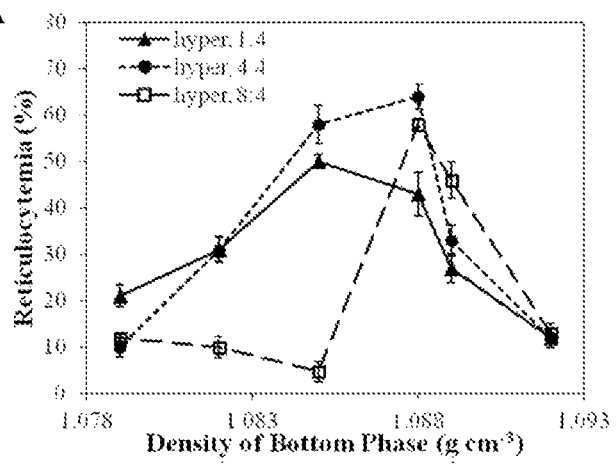
FIGS. 4A-4B illustrate the reticulocytemia (FIG. 4A) and yield (FIG. 4B) changes with different volume ratios (vol. blood (mL):vol. AMPS (mL)) of blood to AMPS in hypertonic systems.
Figure 4B:
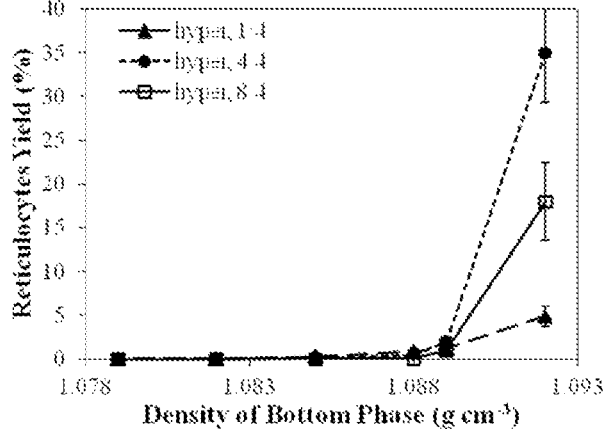

Table 1 details the parameters of the different AMPS that were screened as well as the results from enrichments of reticulocytes. We performed additional enrichments using the hypertonic systems (C1-C6) with different loading volumes (FIGS. 4A and 4B). From this we found multiple systems that were capable of attaining enrichments to reticulocytemias over 50%. Table 2 details the enrichments for different donors with four different AMPS.

The Volume Ratio of Blood to AMPSs Affects Both Yield and Purity of Enrichments.

We expected that the performance of hypertonic and hypotonic AMPSs would be dependent on the volume ratio of blood and AMPSs. In an isotonic system, we anticipated that this dependence would be negligible since water exchange between polymers and blood cells would be minimal. We found, however, that the volume ratio of blood and AMPSs did affect performance in an isotonic system. A range of volumes of blood (1 mL, 4 mL, and 8 mL) were loaded onto 4 mL of the hypertonic AMPS (C1-C6) (FIGS. 4A-4B). FIGS. 4A-4B show the enrichment of reticulocytes in hypertonic systems changes with different volume ratios (vol. blood (mL):vol. AMPS (mL)) of blood to AMPS. Both the reticulocytemia and yield show changes. A 4:4 ratio provides the best yield. Several systems provide enrichment to reticulocytemias over 50%.

Dispersal of Plasma Proteins into AMPS.

We hypothesized that the dependence of enrichments on the volume ratio of blood to AMPS might be due to a slight amount of mixing of plasma which would dilute the phases and would depend on the volume ratio of blood to polymer. We checked the density of the phases after a separation to see if there was a change in the phases. When 2 mL of blood was layered on top of 4 mL of A5, the density of both phases decreased ($\Delta\rho_{top}=-0.013$ g cm$^{-3}$, $\Delta\rho_{bottom}=-0.016$ g cm$^{-3}$); we used isotonic A5 rather than hypertonic AMPS to avoid changes in volume that would result from the cells shrinking or swelling.

TABLE 1

The enrichment of reticulocytes at the interface of dextran-Ficoll AMPSs with varying density and osmolality.

| ID | Concentration (% w/v) | | Tonicity (mOsm) | Density (g cm$^{-3}$) | | AMPS Interface | | Initial |
|----|----|----|----|----|----|----|----|----|
| | Ficoll | dextran | | Top | Bottom | Retic[a] | S.D.[b] | Retic[a] |
| Isotonic Systems (295 ± 15 mOsm) | | | | | | | | |
| A1 | 12.0 | 12.0 | 299 | 1.089 | 1.092 | 1.1 | 0.4 | 1.1 |
| A2 | 11.4 | 11.4 | 295 | 1.084 | 1.087 | 2.1 | 0.7 | 1.1 |
| A3 | 11.1 | 11.1 | 306 | 1.082 | 1.085 | 21 | 5.2 | 1.8 |
| A4 | 10.8 | 10.8 | 301 | 1.080 | 1.083 | 24 | 4.1 | 1.8 |
| A5 | 10.3 | 10.3 | 289 | 1.076 | 1.080 | 28 | 10 | 1.8 |
| Hypotonic Systems (260 ± 10 mOsm) | | | | | | | | |
| B1 | 10.5 | 10.5 | 250 | 1.079 | 1.083 | 2.0 | 1.0 | 1.1 |
| B2 | 10.0 | 10.0 | 252 | 1.074 | 1.078 | 4.7 | 1.5 | 1.1 |
| B3 | 9.5 | 9.5 | 252 | 1.071 | 1.075 | 19 | 1.6 | 1.1 |
| B4 | 9.3 | 9.3 | 269 | 1.068 | 1.072 | 55 | 8.4 | 1.8 |
| B5 | 9.0 | 9.0 | 264 | 1.067 | 1.071 | 43 | 5.1 | 1.8 |
| Hypertonic Systems (330 ± 10 mOsm) | | | | | | | | |
| C1 | 12.0 | 12.0 | 327 | 1.089 | 1.092 | 12 | 0.7 | 2.4 |
| C2 | 11.6 | 11.6 | 340 | 1.086 | 1.089 | 27 | 3.1 | 2.4 |
| C3 | 11.4 | 11.4 | 336 | 1.084 | 1.088 | 43 | 4.7 | 2.4 |
| C4 | 11.0 | 11.0 | 332 | 1.081 | 1.085 | 50 | 1.5 | 2.4 |
| C5 | 10.6 | 10.6 | 328 | 1.078 | 1.082 | 31 | 2.8 | 2.4 |
| C6 | 10.1 | 10.1 | 329 | 1.075 | 1.079 | 21 | 2.4 | 2.4 |

[a]Mean reticulocyte count per 100 erythrocytes (n = 3 technical replicates)
[b]Standard deviation of the replicates
b.f. System with the highest level of enrichment

TABLE 2

Performance of AMPS over different individuals.

| Donor | Initial Retic. | C1 (%) Retic. | C1 (%) Yield | C2 (%) Retic. | C2 (%) Yield | B3 (%) Retic. | B3 (%) Yield | A5 (%) Retic. | A5 (%) Yield |
|---|---|---|---|---|---|---|---|---|---|
| A | 0.80 | 19 | 0.24 | 28 | 0.11 | 35 | 0.013 | 35 | 0.0086 |
| B | 0.85 | 21 | 0.75 | 30 | 0.095 | 49 | 0.053 | 45 | 0.013 |
| C | 1.3 | 18 | 2.4 | 32 | 1.7 | 38 | 0.011 | 45 | 0.00079 |
| D | 0.83 | 15 | 6.0 | 15 | 1.7 | 18 | 0.0065 | 15 | 0.0036 |
| Median | 0.84 | 19 | 1.6 | 29 | 0.89 | 36 | 0.012 | 40 | 0.0061 |
| Min. | 0.80 | 15 | 0.24 | 15 | 0.095 | 18 | 0.0065 | 15 | 0.00079 |
| Max. | 1.3 | 21 | 6.0 | 32 | 1.7 | 49 | 0.053 | 45 | 0.013 |

If a boundary layer of plasma were to penetrate the top phase with the cells and then mixes with the phase, we would expect to see plasma proteins dispersed in the top phase. To visualize the dispersal of plasma proteins into an AMPS during an experiment—layering blood, introduction into a centrifuge, fractionation by centrifugation, and removal from a centrifuge—we added a fluorescent protein into whole blood as a marker. We prepared fluorescein-labeled bovine serum albumin (FITC-BSA) by following the Thermo Scientific protocol for coupling reactions using fluorescein isothiocyanate. After dialysis against isotonic PBS, the final concentration of FITC-BSA was ~7 mg mL$^{-1}$. We mixed this solution with whole blood at a ratio of 1:9 to create an experimental sample. A control sample was made by mixing PBS with blood at a ratio of 1:9. The blood samples were each layered over dextran-Ficoll AMPS (1 mL blood over 3 mL AMPS). The samples were sedimented by centrifugation at an RCF of 2000 g for 100 minutes at 25° C. in an Allegra-6R swinging bucket centrifuge.

Figures 5A, 5B, 5C:
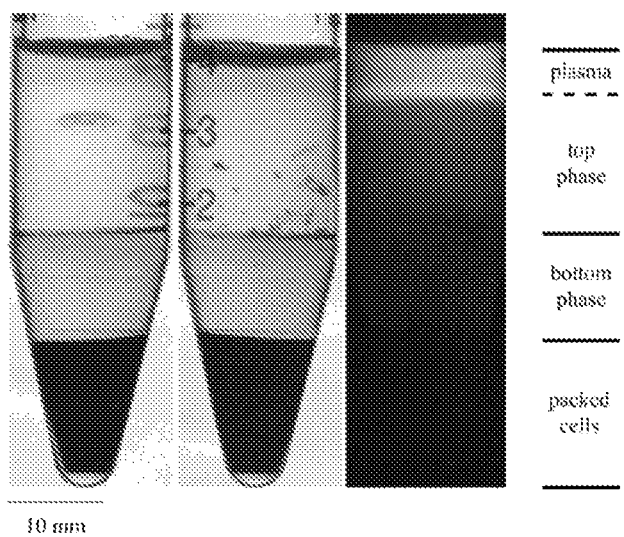
FIGS. 5A-5C illustrate dispersion of protein from plasma into AMPS. Brightfield images of whole blood after fractionation by AMPS without (FIG. 5A) and with (FIG. 5B) the addition of 700 μg/mL fluorescein-labeled BSA.
Figure 6A:
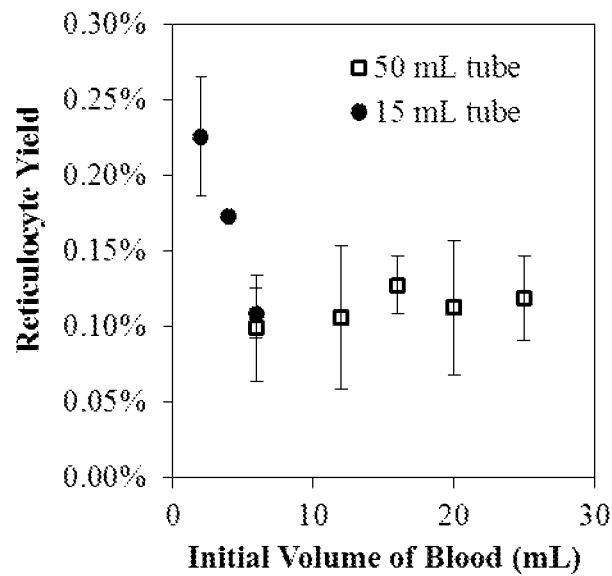
FIGS. 6A-6B illustrate that the reticulocyte enrichment in yield (FIG. 6A) and reticulocytemia (FIG. 6B) over AMPS C2 was comparable over multiple scales of volume.
Figure 6B:
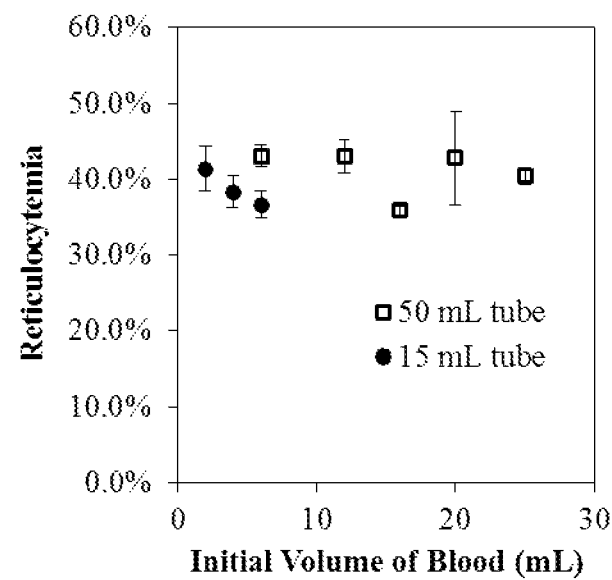

We imaged the systems after fractionation using a combination of brightfield and fluorescent techniques (FIGS. 5A-5C). FIGS. 5A-5C show the dispersion of protein from plasma into AMPS. Brightfield images of whole blood after fractionation by AMPS without (5A) and with (5B) the addition of 700 μg/mL fluorescein-labeled BSA. A fluorescence image (5C) of the tube in (5B) after illumination with longwave UV light. For the fluorescence images, the tubes were kept in a dark box, illuminated with longwave UV light (λ=365 nm), and imaged using a bandpass filter (500-600 nm) in front of the camera. Although the fluorescence intensity is highest in the plasma layer, we observe that some FITC-BSA is present in the top phase of the AMPS. The diffusion length of serum albumin in whole blood over the course of a 100-minute experiment is approximately 5 mm ($D_f$~2.1×10$^{-10}$ m$^2$ s$^{-1}$). The distance between the plasma/top phase boundary and the AMPS interface is 14 mm. Diffusion alone, therefore, cannot account for the presence of FITC-BSA in the top phase of the AMPS. Dilution of the top phase from the mixing of the boundary layer of cells would change the equilibrium of the AMPS, shift the water and polymer contents of the bottom phase, and reduce the bottom phase density.

Reticulocyte Enrichments Scale to 25 mL of Blood without a Loss in Purity.

The purity and yield of reticulocytes remain fairly constant as volumes are increased provided that the volume ratio of AMPS to blood remains constant (FIGS. 6A-6B). FIGS. 6A-6B show that the reticulocyte enrichment over AMPS C2 was comparable over multiple scales of volume. For both reticulocyte yield (A.) and reticulocytemia (B.), only one datum fell outside one standard deviation of the mean over all volumes, and all data were within two standard deviations of the mean. Using the same isotonic dextran-Ficoll AMPS as used in the volume ratio experiments, we performed a series of enrichments on blood from a single donor with volumes of blood ranging from 2 mL to 25 mL. In all cases, a volume ratio of 1:1 between blood and AMPS was used; this ratio provided the best combination of yield and enrichment (FIGS. 4A-4B & FIG. 7). FIG. 7 shows a 1:1 volume ratio of blood to a hypertonic AMPS provided the enhanced enrichment of reticulocytes. Using system C3, we attained a reticulocytemia of 64±3% as measured by flow cytometry. The gray, filled curve shows the blood before enrichment, which had a reticulocytemia of 2.2%. After centrifugation through AMPS, the fraction of cells at the interface is dominated by reticulocytes (orange curve). Acridine orange (AO) preferentially stains the RNA in the reticulocytes, and causes the shift to the right. Both 15 mL and 50 mL conical tubes were used. Interestingly, the yield initially decreased as volume increased. At 6 mL, the results were similar for both the types of tubes used. Above this volume, however, yield and reticulocytemia remained relatively constant.

Pre-Enrichment Increases the Purity of the Final Enrichment.

When using differential centrifugation, naturally pre-enriched blood has a higher final enrichment than normal blood. Similarly, we expected that blood pre-enriched for reticulocytes by density would have a higher final enrichment after centrifugation through an AMPS.

Using blood from a single donor with an initial reticulocytemia of 2.2%, we pre-enriched reticulocytes from 100 mL of blood with two different methods: a) differential centrifugation, and b) centrifugation through AMPS C1. The enriched fractions collected had a reticulocytemia of 4.7% and 14%, respectively. The total amount of cells recovered differed as well. We recovered approximately 8 mL of packed cells from differential centrifugation and resuspended them in a volume of 16 mL using homologous plasma recovered from the centrifugation. We only recovered ca. 100 μL of packed cells from AMPS C1. After washing these cells three times in PBS, we resuspended them in a final volume of 3 mL. For the final enrichment, we split each suspension into thirds and layered them over 4 mL of AMPS C1. After centrifugation, we recovered cells from the AMPS interface and washed them three times in PBS. Using flow cytometry, we measured the reticulocytemia of the final enrichments. The results were similar for the fraction pre-enriched by differential centrifugation and that pre-enriched by centrifugation through AMPS. Final reticulocytemia was 20% and 21%, respectively.

Osmotic Effects on Reticulocyte Enrichment by Density.

As discussed in the manuscript, systems with different osmolalities achieved different yields when final reticulocytemias were similar. Also, different osmolalities had enhanced enrichments for different densities of AMPS (FIG. 2). The effect of osmolality on the density of the cell populations of interest—reticulocytes and mature erythrocytes—may explain the difference in yields.

A cell at osmotic equilibrium with a system has a concentration of solutes, c, and a volume, V. Both the cell and the surrounding environment have a osmolarity:

$$\phi = \frac{c}{V}.$$

If the cell is now placed into a hypertonic environment with osmolarity, $\phi'=\phi+\delta\phi$, where $\delta\phi>0$, then the volume of the cell will change to compensate by losing water. We assume that the concentration of solutes remains fairly constant due to the presence of ion pumps to maintain internal ion concentrations. Although there still may be some solute exchange between the cell and environment, we assume that at least, $$\frac{\delta c}{c} << \frac{\delta V}{V}.$$

With this assumption then, the cell volume changes to V', given by Equation 1:

$$V' = \frac{V}{1+\frac{\delta\phi}{\phi}} \quad \text{(Equation 1)}$$

This change in volume shifts the density of a cell $$\left(\rho_1 = \frac{m_1}{V_1}\right)$$

by changing both the mass and volume. The mass can be split into both dry mass and water mass, $m_1=m_{1d}+m_{1w}$. The density then shifts as follows:

$$\rho_1' = \frac{m_1'}{V_1'} = \frac{m_1 + (V_1' - V_1)\rho_w}{\frac{V_1}{1+\frac{\delta\phi}{\phi}}} \quad \text{(Equation 2)}$$

$$\rho_1' = \rho_1\left(1+\frac{\delta\phi}{\phi}\right) - \left(\frac{\delta\phi}{\phi}\right)\rho_w \quad \text{(Equation 3)}$$

$$\rho_1' - \rho_w = \left(1+\frac{\delta\phi}{\phi}\right)(\rho_1 - \rho_w) \quad \text{(Equation 4)}$$

Two different cells (e.g., a reticulocyte and a mature erythrocyte) with a density different of $\Delta\rho=\rho_2-\rho_1$, will have a new density difference of $$\Delta\rho' = \Delta\rho\left(1+\frac{\delta\phi}{\phi}\right).$$

On a population scale, this means that the distance between the two peaks of the density distribution of cells will scale with the osmolality.

Morphology of Cells after Centrifugation Through AMPSs.

Figure 8:
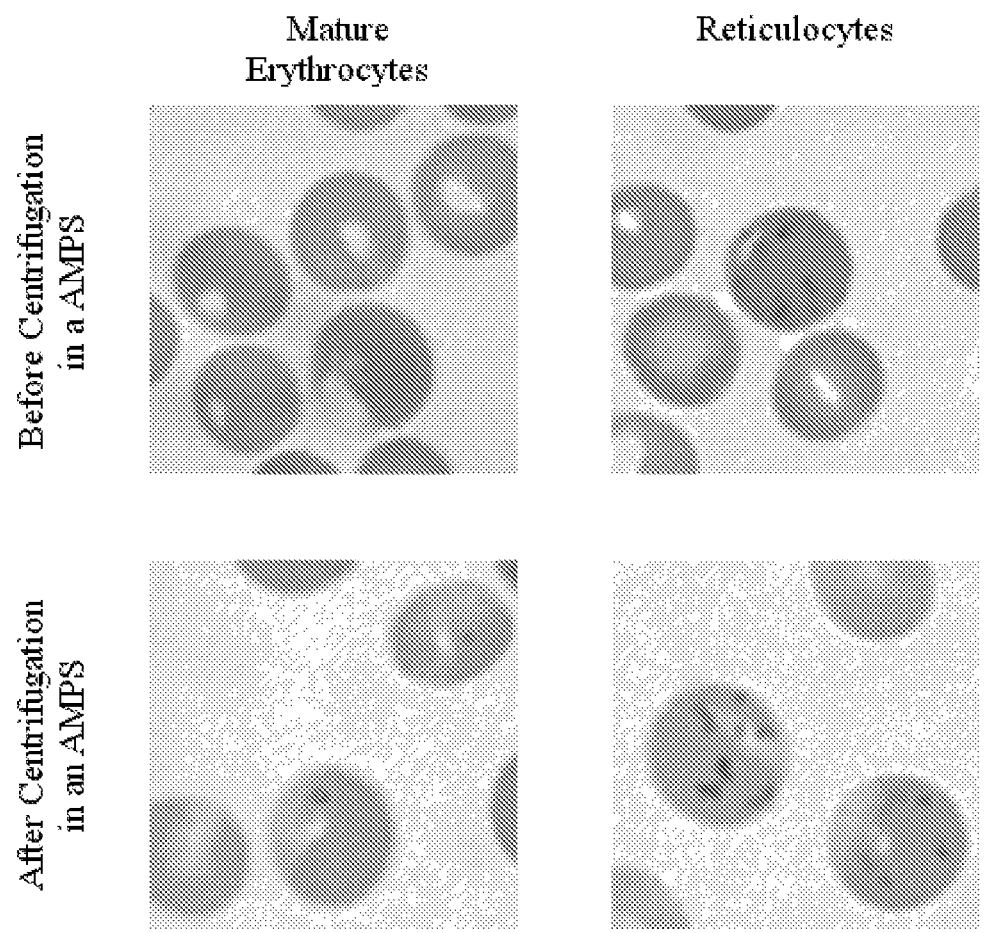
FIG. 8 illustrates the morphology of cells after separation using an AMPS.

Washing cells was an important step to restore morphology and remove excess polymer. Dextran adsorbs to the surface of cells. Repeated washing removes some, but not all of the dextran. Washing cells in an isotonic buffer such as PBS appeared to return them to their physiological volumes; that is, unwashed cells from hypotonic systems appeared swollen when observed by microscopy. After extracting and washing cells from the interface of the AMPSs, we found that both mature erythrocytes and reticulocyte had a similar morphology to fresh blood on thin blood smears (FIG. 8). FIG. 8 shows the morphology of cells after separation using an AMPS. Representative micrographs of mature erythrocytes and reticulocytes before and after centrifugation in an AMPS demonstrate no significant morphological change as a result density-based separation. The blue stained clumps of RNA identify the reticulocytes in the right hand micrographs.

We compared the mean corpuscular volume (MCV) and the mean corpuscular hemoglobin (MCH) of RBCs isolated from five random donors before and after separations by AMPS (Table 3). These quantitative results support the hypothesis that sedimentation through the AMPS does not drastically affect the morphology or the contents of cells. Evaluation of the percentage of cells that were hypochromic, hyperchromic, microcytic, and macrocytic revealed very little change between the original blood and the cells from the bottom fraction of the AMPS for the latter three indices. There was a slight increase in the percent of hypochromic cells and decrease in the percentage of hyperchromic cells that indicates minor swelling, but the effect is small and could be further reduced by increasing the salt content of the AMPS. Donors A and E had the lowest mean cellular hemoglobin concentration (MCHC) and, hence, had potentially more cells near the threshold of being hypochromic; the effect of a slight swelling would be more pronounced in these two samples.

Parasite Culture.

Parasites were maintained in vitro in rhesus blood (purchased from the New England Primate Research Center, Southborough, Mass.) at 2% hematocrit, in RPMI-1640 supplemented with 25 mM HEPES, sodium bicarbonate, 50 mg/L hypoxanthine, and 0.5% Albumax. Parasitemia of cultures are determined by microscopy. Reticulocytemias for each enriched sample are given in Table 4.

Invasion Assays.

For invasion assays, late stage *P. knowlesi* H parasites were purified through magnet columns (MACS Miltenyi Biotec). They were plated at a final parasitemia of 0.5-1% in 150 µl cultures at 2% hematocrit in a 96 well plates. Normal human blood and rhesus blood were used as controls. Each red blood cell type was plated in triplicate. Parasites were incubated overnight to allow re-invasion. Parasitized erythrocyte multiplication rate (PEMR) was calculated by dividing the parasitemia after re-invasion to the initial parasitemia seeded.

TABLE 3

Hematological indices of the size and contents of erythrocytes (RBCs) pre- and post-exposure to an AMPS.

| | MCV[a] (fL) | | MCH[b] (pg) | | % Macro[c] | | % Micro[d] | | % Hypo[e] | | % Hyper[f] | |
|---|---|---|---|---|---|---|---|---|---|---|---|---|
| Donor | Pre | Post | Pre | Post | Pre | Post | Pre | Post | Pre | Post | Pre | Post |
| A | 82 | 84 | 27 | 26 | 0.0 | 0.1 | 1.2 | 0.8 | 4.8 | 12 | 0.2 | 0.1 |
| B | 92 | 93 | 31 | 30 | 0.7 | 0.7 | 0.2 | 0.1 | 0.3 | 0.4 | 0.5 | 0.0 |

TABLE 3-continued

Hematological indices of the size and contents of erythrocytes (RBCs) pre- and post-exposure to an AMPS.

| Donor | MCV[a] (fL) | | MCH[b] (pg) | | % Macro[c] | | % Micro[d] | | % Hypo[e] | | % Hyper[f] | |
|---|---|---|---|---|---|---|---|---|---|---|---|---|
| | Pre | Post | Pre | Post | Pre | Post | Pre | Post | Pre | Post | Pre | Post |
| C | 90 | 91 | 30 | 30 | 0.4 | 0.4 | 0.3 | 0.2 | 1.0 | 1.5 | 0.3 | 0.0 |
| D | 94 | 95 | 31 | 31 | 1.3 | 1.5 | 0.3 | 0.3 | 0.4 | 0.7 | 0.4 | 0.4 |
| E | 85 | 86 | 27 | 26 | 0.1 | 0.1 | 0.9 | 0.7 | 7.6 | 15 | 0.1 | 0.0 |

[a]mean corpuscular volume
[b]mean corpuscular hemoglobin
[c]percentage of erythrocytes that are macrocytic
[d]percentage of erythrocytes that are microcytic
[e]percentage of erythrocytes that are hypochromic
[f]percentage of erythrocytes that are hyperchromic

TABLE 4

Reticulocytemia of samples used for invasion assays.

| | Matched Reticulocytemia (%)* | |
|---|---|---|
| Donor | AMPS[a] | DC-Percoll[b] |
| 1 | 9.2 | 9.2 |
| 2 | 21 | 19 |
| 3 | 21 | 20 |
| 4 | 5.0 | 11 |
| 5 | 7.0 | 7.1 |
| 6 | 5.6 | 3.5 |
| 7 | 16 | 20 |

[a]blood enriched by aqueous multiphase systems (AMPSs)
[b]blood enriched by differential centrifugation followed by centrifugation over layered Percoll
*reticulocytemia was matched by diluting the system with a greater reticulycemia with normal blood.

Invasion of *P. falciparum*.

Figure 9:
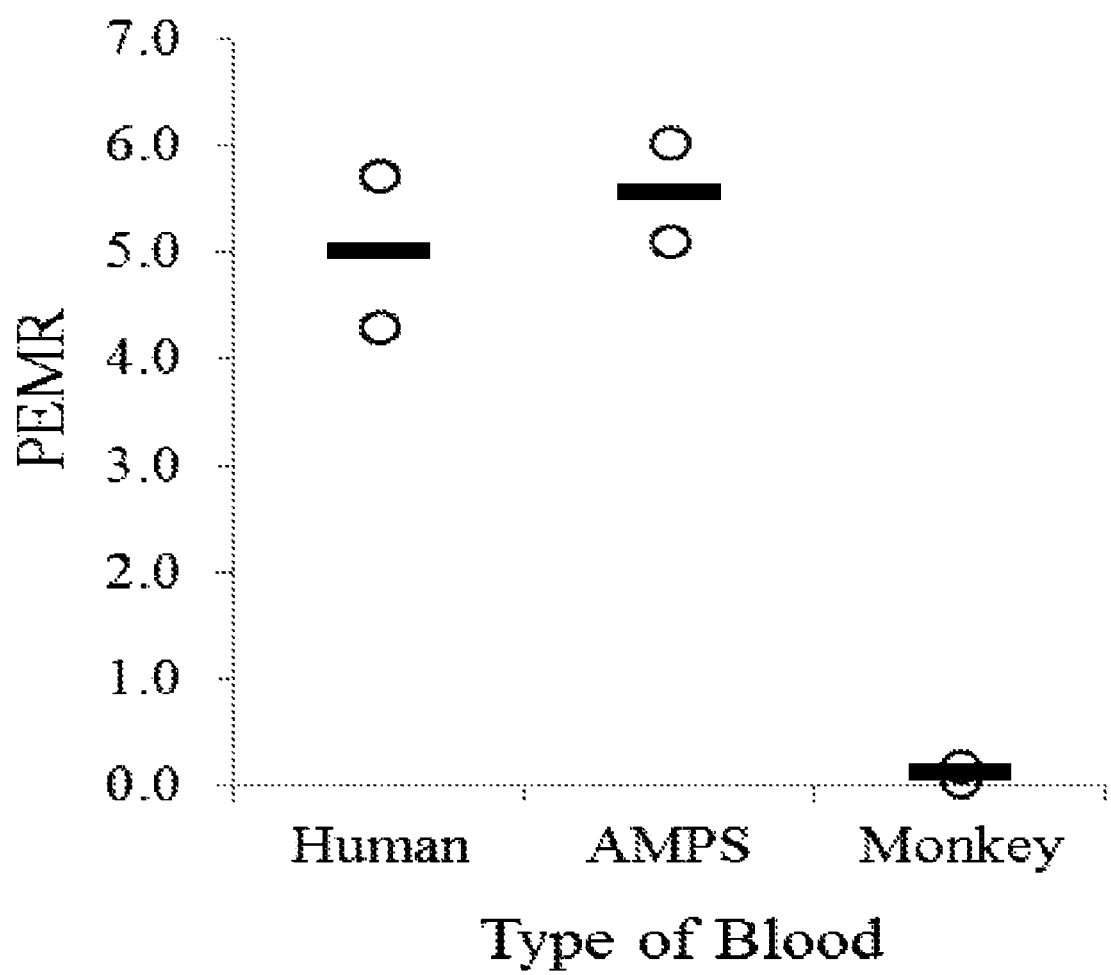
FIG. 9 illustrates that *P. falciparum* 3D7 strain grows in blood enriched for reticulocytes by AMPS at a rate similar to that at which it grows in normal blood.

Even if parasites can invade erythrocytes, mechanical stress from centrifugation or polymers on the surface of cells might reduce the infection rate of erythrocytes. *P. falciparum* 3D7 strain should have a similar invasion rate of erythrocytes regardless of the reticulocyte content. Invasion assays using *P. falciparum* provide an additional control to see whether density centrifugation through AMPS obstructs the invasion of malaria parasites compared to normal human blood. Enrichment by AMPS did not affect the PEMR for *P. falciparum*. Parasites invaded cells at rates similar to those in normal blood (FIG. 9). FIG. 9 shows that *P. falciparum* 3D7 strain grows in blood enriched for reticulocytes by AMPSs at a rate similar to that at which it grows in normal blood. Blood from a rhesus monkey provides a negative control to demonstrate that the parasite requires suitable host cells for invasion. Open circles depict data from different donors (n=2) and horizontal bars indicate the mean parasitized erythrocyte multiplication rate (PEMR).

Direct Growth of Reticulocytes and Labeled Methods to Enrich Reticulocytes are not Practical for the Routine Cultivation of Malaria.

Reticulocytes may be obtained directly from the in vitro culture of hematopoietic stem cells (HSCs). This method has been used to culture *P. vivax* at a parasitemia below 0.0013%; access to HSCs remains expensive, and asynchronous erythropoiesis limits reticulocytemia. Blood can be enriched highly for reticulocytes (>90% measured by microscopy) using antibodies that differentiate reticulocytes from mature erythrocytes based on characteristic surface proteins. Recovering undamaged reticulocytes from affinity-based separations is difficult, however, and is expensive for routine use. As a result, attempts to enrich reticulocytes for the cultivation of malaria parasites have focused on label-free methods using the physical properties of these cells (e.g., size and density).

Density Provides a Label-Free Parameter to Enrich Reticulocytes.

Reticulocytes are generally larger in volume than mature erythrocytes and they contain ribosomal RNA; the average density of reticulocytes, thus, is slightly lower than that of mature erythrocytes ($\Delta\rho \approx 0.009$ g cm$^{-3}$). The reported values of the densities of these two populations differs with the study and the method, but most studies agree that the reticulocyte population is concentrated in the least dense quarter of the distribution of density of erythrocytes. Differential centrifugation and centrifugation through a gradient in density are the most common methods to separate these types of cells by density.

In differential centrifugation, erythrocytes sediment pack at the bottom of a container; the erythrocytes located at the top of the packed cells have a lower density than those below. As a result, the top quarter of the packed cells contain relatively more reticulocytes than the lower three quarters. Starting with whole blood from normal subjects, differential centrifugation results in an average enrichment of reticulocytes of 2.6%. Using sources of blood with elevated reticulocyte counts (e.g., blood from umbilical cords or from patients with hemochromatosis) can increase the final enrichment obtained from differential centrifugation. Use of these sources is a barrier to the routine use of this method. Cord blood is prohibitively expensive, and the total volume of blood that can be harvested from each cord is limited to an average of 75 mL.

Gradients in density improve the enrichment of reticulocytes by separating reticulocyte-rich fractions and reticulocyte-poor fractions of erythrocytes into visible bands. Percoll—a suspension of colloidal silica stabilized by polyvinylpyrrolidone (PVP)—will form a time-dependent gradient in a centrifuge with an angled rotor. Separations are highly dependent on the centrifugation parameters (e.g., rotor angle, applied relative centrifugal force, acceleration, and time). As a result, reproducibility suffers; initial reports of fractionation of reticulocytes over Percoll gradients achieved a 78% reticulocytemia in enriched fractions of blood, while average reticulocytemias %.

Layered gradients—manually assembled by carefully layering decreasing concentrations of aqueous solutions of a dense solute (e.g., sucrose or arabinogalactan)—provide a means to tune the resolution of separations at multiple densities. The boundary between layers provides a location at which cells of specific densities will collect. Such gradients achieve 68% reticulocytemia in some subjects, but they are time-consuming to assemble and susceptible to mixing and destruction without careful handling.

B. Diagnosis of Iron Deficiency Anemia

Aqueous multiphase systems (AMPS) are solutions of immiscible polymers and surfactants that spontaneously phase segregate and form discrete layers. Between each phase is an interface with a molecularly sharp step in density; this step in density can be used to separate subpopulations of cells by density.

Here, we demonstrate the use of aqueous two-phase and three-phase systems to diagnose IDA; we also compare these results to red blood cell indices measured by a hematology analyzer. While these indices cannot be directly measured by an AMPS, many are related to the density and can therefore be inferred using results from an AMPS. We image the results of each AMPS test with a digital scanner in transmission mode and use digital analysis to quantify the intensity of red color found at each interface (red intensity). By comparing the intensity of red color to red blood cell indices, we can empirically set a cutoff value for a "yes" or "no" diagnosis of IDA. After the determination of the diagnostic cutoff values, sensitivity and specificity can be determined for each system.

In this application, we describe two different systems. A simple two-phase AMPS (IDA-AMPS-2) can be used to easily diagnose microcytic and hypochromic anemia by the presence of an observable band of RBCs at the liquid/liquid interface above the packed normal RBCs. A three-phase AMPS (IDA-AMPS-3) is capable of capturing microcytic and hypochromic RBCs at two liquid/liquid interfaces and allows for the differentiation between β-TT and IDA owing to the difference in RBC density distribution between the two conditions.

Selection of a Proper Density Gradient in AMPS

An AMPS with n total phases will contain n+1 interfaces (e.g. in a two phase system: air/phase-1, phase-1/phase-2, and phase-2/container).

In order to detect the presence of microcytic and hypochromic red blood cells, a properly designed AMPS should: i) have a top layer with density greater than that of plasma and its components (~>1.025 g cm$^{-3}$) in order to minimize dilution of the AMPS, ii) have a bottom layer less dense than the average red blood cell density (~1.095 g cm$^{-3}$) such that normal blood will pack at the bottom of the tube, iii) maintain biocompatibility by tuning the pH (7.4) and osmolality (290 mOsm) to match blood, and iv) undergo phase separation in a short amount of time (≤5 minutes) under centrifugation (13,000 g).

IDA-AMPS-2 was designed with a top layer density $\rho_{top}$=1.0784 g cm$^{-3}$ and bottom layer density $\rho_{bot}$=1.0810 g cm$^{-3}$ and was comprised of 10.2% (w/v) dextran (MW~500 kD), 10.2% (w/v) Ficoll (MW~400 kD), and 0.7% (w/v) Nycodenz. IDA-AMPS-3 contained 10.2% (w/v) partially hydrolyzed poly(vinyl alcohol) (containing 75% hydroxyl and 25% acetate groups) (MW~2 kD), 5.6% (w/v) dextran (MW~500 kD), and 7.4% (w/v) Ficoll (MW~400 kD). The density of the phases were $\rho_{top}$=1.0505 g cm$^{-3}$, $\rho_{mid}$=1.0810 g cm$^{-3}$, $\rho_{bot}$=1.0817 g cm$^{-3}$.

An AMPS Diagnostic can be Easy to Use, Rapid, and Fieldable

We previously demonstrated the use of a point-of-care assay for sickle cell disease using AMPS. A similar strategy is employed here. Briefly, a plastic microhematocrit tube is preloaded with 15 μl AMPS solution and centrifuged for 4 minutes at 13,000 g in a hematocrit centrifuge (CritSpin, Iris Sample Processing) in order to separate the phases.

A finger prick of blood (5 μl) is loaded at the top of the tube through capillary action enabled by a small hole poked in the side of the tube. A silicone sleeve is then slid over the hole to prevent the blood leaking during centrifugation. Up to 12 tubes can then be loaded into the hematocrit centrifuge and spun for the desired time.

The total time needed to perform this assay is less than ten minutes and all of the components, including a battery to power the centrifuge, can fit into a backpack.

Analysis of the Distribution of Red Intensity with Image Processing Software

The diagnostic readout of an AMPS test can be done readily with the naked eye by visualizing the number of red bands at a given interface. Here, the general diagnosis of microcytic/hypochromic anemia can be made visually, but the differentiation between IDA and β-TT may require quantification of the red blood cell density distribution.

Figure 10:
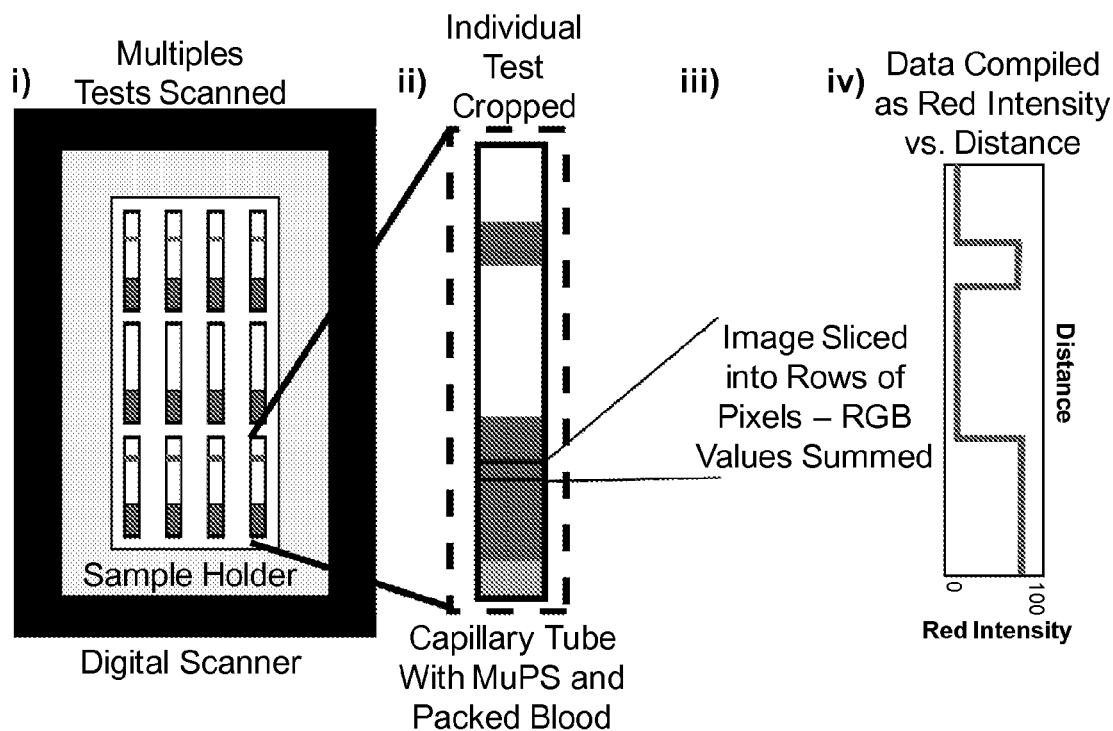
FIG. 10 illustrates a method used to analyze the quantity and location of RBCs in an AMPS test using a digital scanner and a custom computer program.

FIG. 10 shows the procedure used for digital analysis of the AMPS tests. A flatbed scanner in transmission mode imaged up to 12 tests simultaneously (Epson Perfection V330 Photo). Scanned images were analyzed using a custom Matlab program using the following steps: i) images were matched to a key file for registration and cropped to a standard size, ii) individual capillary tubes were cropped and selected relative to their place in the test holder, iii) a given tube was sliced into cross sections and the red intensity value was calculated by summing the difference in the red channel from the blue and green channels (see Supporting Information for Diagnosis of Iron Deficiency Anemia for more details), and iv) the values for each slice were compiled as a text file for later analysis.

Centrifugation of Blood Through IDA-AMPS-2 Provides a Clear Visual Diagnostic

IDA-AMPS-2 provides two bins of density in which blood can collect: 1) blood of low density (<1.081 g cm$^{-3}$) at the interface between the top and bottom phases (T/B), and 2) normal blood (≥1.085 g cm$^{-3}$) at the bottom of the tube above the white sealing clay.

Figure 11:
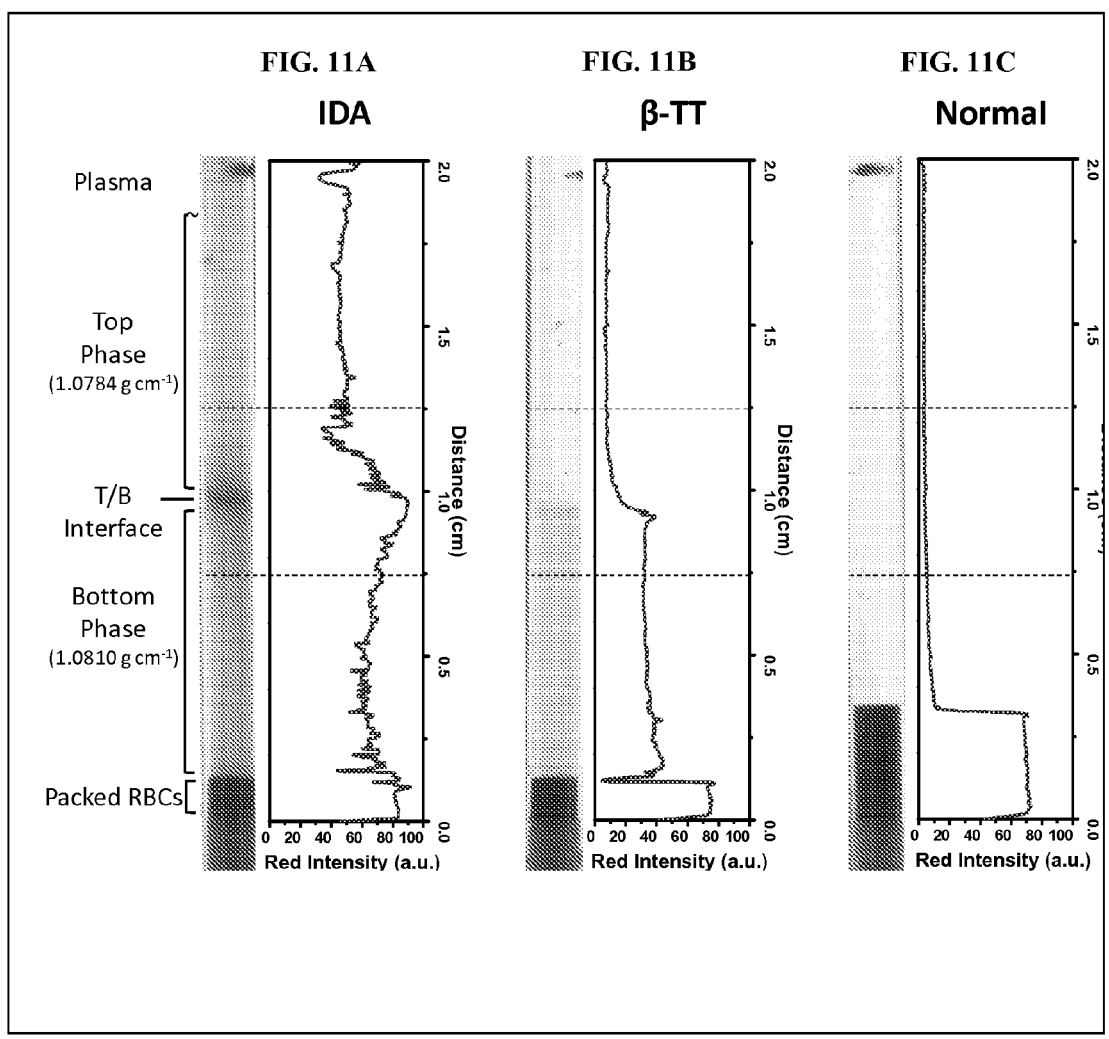
FIGS. 11A-11C illustrate representative IDA-AMPS-2 tests for iron deficient (FIG. 11A), β-thalessemia trait (FIG. 11B), and normal (FIG. 11C) blood after four minutes centrifugation at 13,000 g.

After ten minute of centrifugation at 13,000 g all of the RBCs reach their equilibrium position. The diagnosis of microcytic and hypochromic anemia, however, only requires that normal blood can be differentiated from anemic blood. After four minutes normal RBCs are found to be packed at the bottom of the tube while less dense RBCs continue to travel through the AMPS; some of these cells readily pack at the T/B interface (FIGS. 11A-11C). FIGS. 11A-11C show representative IDA-AMPS-2 tests for iron deficient (11A), β-thalassemia trait (11B), and normal (11C) blood after four minutes centrifugation at 13,000 g. Visual diagnostic can be made by noting the red color above the packed cells and at the T/B interface. Red intensity plots quantify the red channel absorption in the tube. Dashed lines represent area of interest near the T/B interface used for quantification in FIG. 12. A test is considered IDA/β-TT positive if red cells remain above the packed hematocrit.

Hematocrit can be estimated from an AMPS test; the total number of RBCs varies for a given sample and is typically lower for β-TT and IDA compared to normal blood.

Digital analysis of a diagnostic test provides a cost effective means to eliminate reader bias. Desktop scanners are inexpensive (<$100) and can be portable. Recent innovations have enabled the use of smart phone cameras as a scanner for colorimetric diagnostics.

Figure 12:
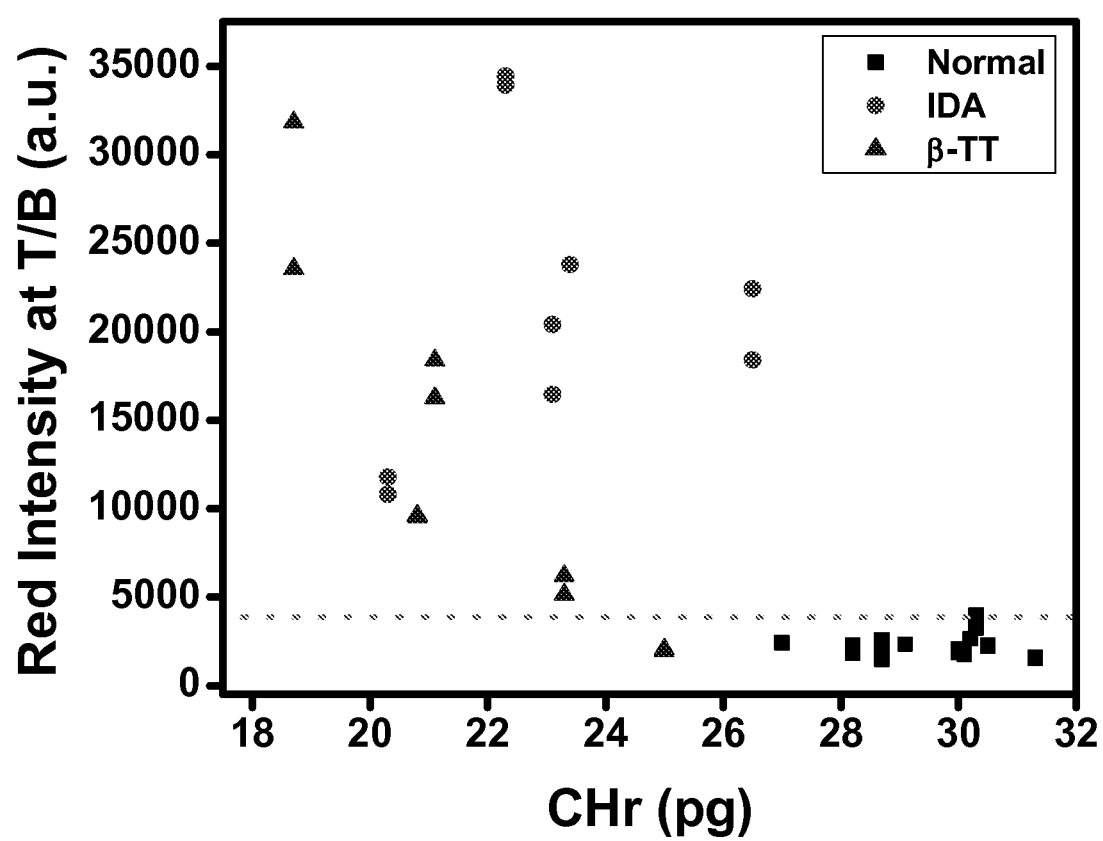
FIG. 12 illustrates digital analysis of the IDA-AMPS-2 system.

Using the output of the digital analysis we evaluate the IDA-AMPS-2 system by integrating the red intensity at the T/B interface, between 0.75 and 1.25 cm from the bottom of the tube (FIG. 12). FIG. 12 shows a digital analysis of the IDA-AMPS-2 system. Red intensity values were obtained by summing the total red intensity between 0.75 and 1.25 cm from the top of the clay seal. The diagnostic threshold was set to be three standard deviations above the mean (gray dashed line). Each data point represents an individual sample. The threshold for IDA/β-TT positive (dashed line) was established as three standard deviations above the mean red intensity value for normal blood (n=11).

Reticulocyte hemoglobin content (CHr) is a blood index which can be related to serum ferritin levels and has been used as diagnose IDA. Functional iron deficiency has been defined as CHr<28 pg and percent hypochromic RBCs (% HYPO)>5%. FIG. 12 shows a comparison of red intensity at the TB interface with CHr values obtained from a hematology analyzer.

IDA-AMPS-3 with Digital Analysis can Differentiate IDA from β-TT

β-Thalassemia trait blood is characterized by a bimodal RDW. IDA-AMPS-3 was designed with three bins of density which enable the differentiation of IDA and β-TT. The top phase (1.0550 g cm$^{-3}$) prohibits plasma and low-density white blood cells from diluting the system, and the middle and bottom phases are designed to be very close in density (1.0810 g cm$^{-3}$ and 1.0817 g cm$^{-3}$ respectively) to provide a method to correlate the number of RBCs captured at both liquid/liquid interfaces with RDW.

Figure 13:
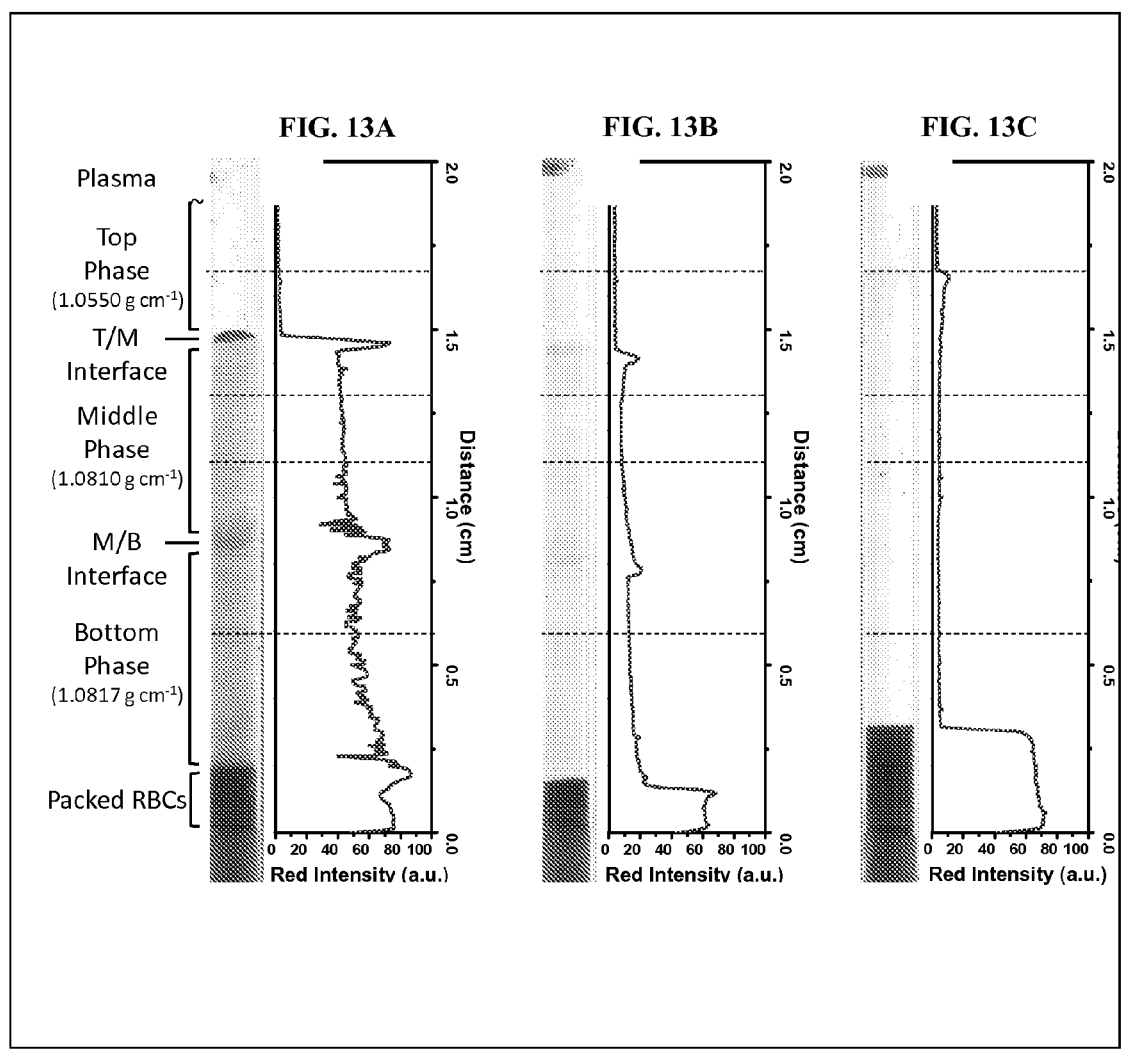
FIGS. 13A-13C illustrate representative IDA-AMPS-3 tests for iron deficient (FIG. 13A), β-thalessemia trait (FIG. 13B), and normal (FIG. 13C) blood after four minutes centrifugation at 13,000 g.

FIGS. 13A-13C show typical IDA-AMPS-3 tests for of IDA, β-TT, and normal samples. Dashed lines represent the area of interest near the T/M interface (dark blue lines) and M/B interface (black lines) selected for digital analysis. Specifically, FIGS. 13A-13C show representative IDA-AMPS-3 tests for iron deficient (A), β-thalassemia trait (B), and normal (C) blood after four minutes centrifugation at 13,000 g. Visual diagnostic of microcytic and hypochromic anemia can be made by noting the RBCs at the T/M and M/B interfaces. Digital evaluation of the red intensity plots (right) enable differentiation between IDA and β-TT. Dashed lines represent area of interest near the T/M interface (dark blue lines) and M/B interface (black lines) used for quantification in FIG. 14.

Figure 14:
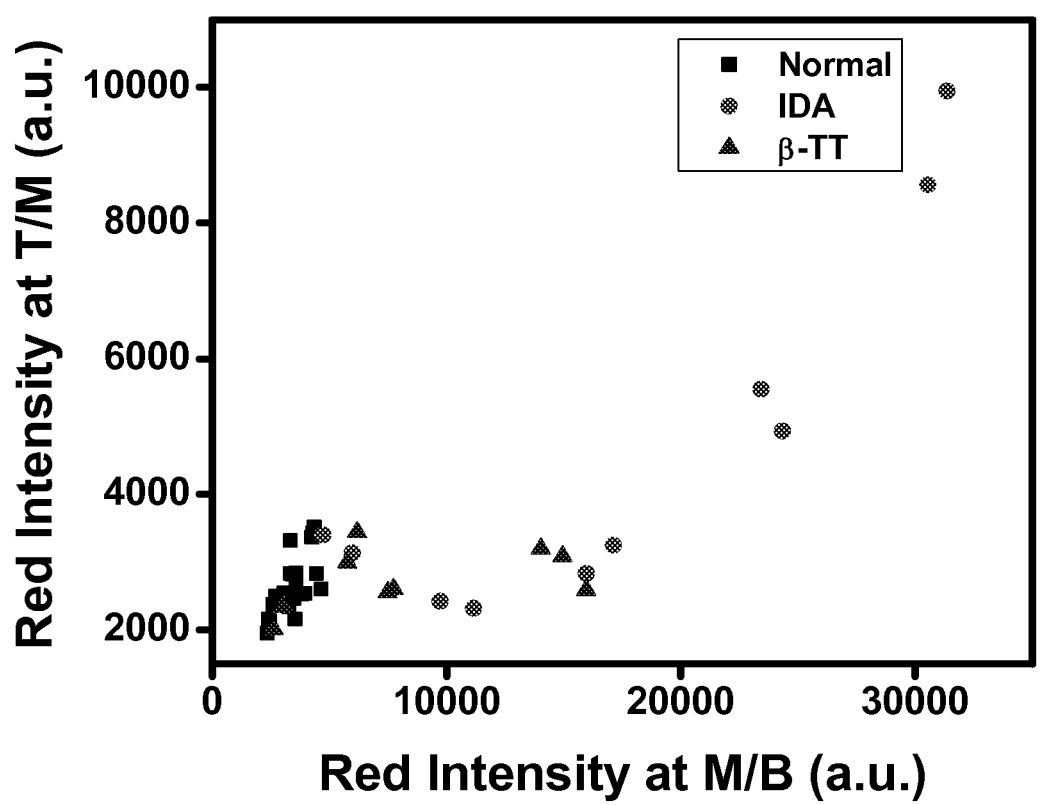
FIG. 14 illustrates the comparison of red intensity at the top/middle (T/M) and middle/bottom (M/B) liquid/liquid interfaces in IDA-AMPS-3.

Digital analysis of the red intensity at the top/middle (T/M) and middle/bottom (M/B) interfaces enables a means to compare the RDW for IDA and β-TT samples (FIG. 14). FIG. 14 shows a comparison of red intensity at the top/middle (T/M) and middle/bottom (M/B) liquid/liquid interfaces in IDA-AMPS-3. Normal blood is expected to exhibit a low value at each interface. In β-TT, the characteristic bimodal red blood cell distribution width (RDW) enables differentiation from IDA; RBCs will fall mainly at one liquid/liquid interface. IDA blood exhibits a large RDW and thus is expected to have similar red intensities at the T/M and M/B interfaces. Normal blood is expected to have a low red intensity for both T/M and M/B. The large RDW of IDA blood (i.e. a large RBC density distribution) results in a high red intensity at both interfaces while the small RDW of β-TT blood yields a high red intensity at either T/M or M/B, depending on the individual patient.

Figure 31:
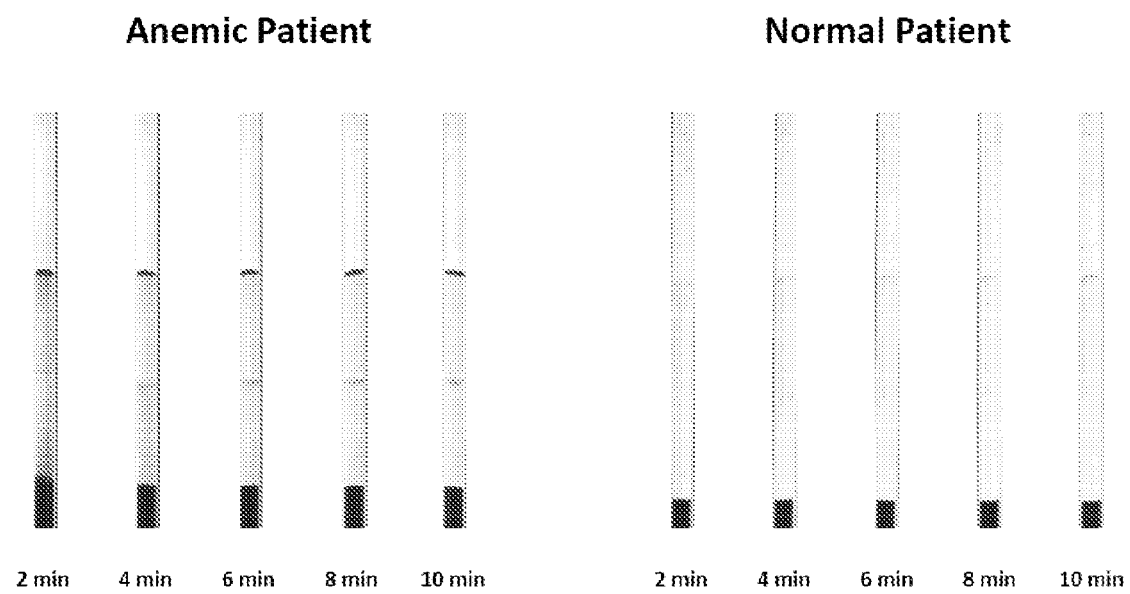
FIG. 31 shows the time dependence of the AMPS test of the IDA patient and normal patient.

FIG. 31 demonstrated the time dependence of the IDA analysis. As shown in FIG. 31, in some embodiments, the MPS and the patient's blood sample were centrifuged for 2 min, 4 min, 6 min, 8 min or 10 min. Thus, in some cases the observed mixture was at its dynamic state, not its thermodynamic state. On the left side of FIG. 31, it could be observed that certain population of the red blood cells moved through the system gradually (comparison between the results at 2 min with 4, 6, 8, and 10 min). Thus, the MPS as described herein can also be used to generate information-rich analysis, e.g., the size or shape distribution of the cells with the same density (because the cells with the same density but different sizes or shapes may have different settling rates in the MPS).

In summary, we have applied aqueous multiphase systems (AMPS) to the diagnosis of iron deficiency anemia (IDA) and β-thalassemia trait (β-TT). This relies on the prevalence of red blood cells (RBCs) which are less dense than normal RBCs.

The use of the transient or dynamic properties of RBCs moving through an AMPS. For the sickle cell diagnosis embodiment, we rely on equilibrium density of the RBCs. Here, we are assessing the tests after centrifugation of <5 minutes, well before equilibrium is reached. By doing this we have a more information rich system.

The digital analysis program we have developed in Matlab has enabled us to collect an immense amount of information about a blood sample. By analyzing the red intensity in the AMPS tube we can correlate the results to many of the parameters of a complete blood count. The current digital analysis program is significantly more complex than previous attempts at RBC quantification for the sickle cell project.

The combination of the previous two points makes possible AMPS as "point-of-care hematology." We believe that this AMPS test in combination with another designed for white blood cells could allow us to very easily measure many blood characteristics that are currently measured with expensive laboratory-based hematology analyzers.

C. Diagnosis of Sickle Cell Disease

Despite the existence of effective low-cost interventions, child mortality attributable to sickle cell disease (SCD) remains high in low-resource areas due, in large part, to the lack of accessible diagnostic methods. Self-assembling stepgradients in density created by aqueous multiphase systems (AMPSs) enable screening for SCD in the field by detecting sickled cells. AMPS separate different forms of red blood cells by density in a microhematocrit centrifuge, and provide a visual means to distinguish individuals with SCD from those with normal hemoglobin, or with non-disease, sickle-cell trait, in under 12 minutes. Visual evaluation of a simple two-phase system to identify SCD has a sensitivity of 90% and a specificity of 97%. A three-phase system identified SCD with a sensitivity of 91% and a specificity of 88%. This system could also distinguish the main subclasses of SCD (Hb SS and Hb SC). This test demonstrates the usefulness of AMPSs in point-of-care diagnostic hematology.

Blood is a complex mixture of many types of cells and each type can be divided into subtypes. In sickle cell disease, the presence of dense, sickled cells provide a diagnostic marker for the disease. This application demonstrates a density-based separation of red blood cells in a system of aqueous multiphase polymers that enables a visual test that identifies sickle cell disease, starting from samples of whole blood, in less than 12 minutes. This low-cost, simple test could provide a means to enable diagnosis of sickle cell disease in low-resource settings, and enable life-saving interventions for children with the disease. The method itself provides a demonstration of the use of a biophysical indicator (here, density) rather than a biochemical marker (e.g., proteins separated by gel electrophoresis) as a means to do point-of-care hematology.

This embodiment describes two rapid tests for SCD based on a sensitive but convenient measurement of the density ($\rho$, g cm$^{-3}$) of red blood cells using aqueous multiphase systems (AMPSs)—mixtures of polymers in water that form immiscible phases. AMPSs provide a method of separating particles by density; the discrimination between particles of different density using an AMPS can be high ($\Delta\rho$<0.001 g cm$^{-3}$). Each phase of an AMPS is separated by an interface that defines a step in density. AMPSs are thermodynamically stable and re-form if disturbed by stirring or shaking AMPSs can be designed to be biocompatible, and have been used to separate mammalian cells by surface interactions.

Our tests use AMPSs to separate erythrocytes into multiple bins of density; the presence or absence of erythrocytes in the bins distinguishes individuals with SCD from individuals with either normal hemoglobin (Hb AA) or sickle-cell trait (Hb AS). The simpler test, SCD-AMPS-2, uses two phases; the higher resolution test, SCD-AMPS-3, uses three phases. We evaluated our tests both visually and digitally in a population of 59 subjects (33 negative—Hb AA or Hb AS, 26 positive—Hb SS, Hb or SC). Both tests diagnosed SCD positive samples with a sensitivity >90% and a specificity >88%.

SCD-AMPS-3 is further able to distinguish between the two main forms of SCD: i) Hb SS, which accounts for the majority (~75%) of SCD, and ii) Hb SC, which constitutes most of the remaining cases of SCD (~20%). These two variants of SCD have important differences in pathophysiology; effective diagnosis of the genotype would enable management to be tailored to the appropriate risks.

Bins of Density Provide a Specific Test for SCD that can Distinguish Sub-Types.

Figure 15:
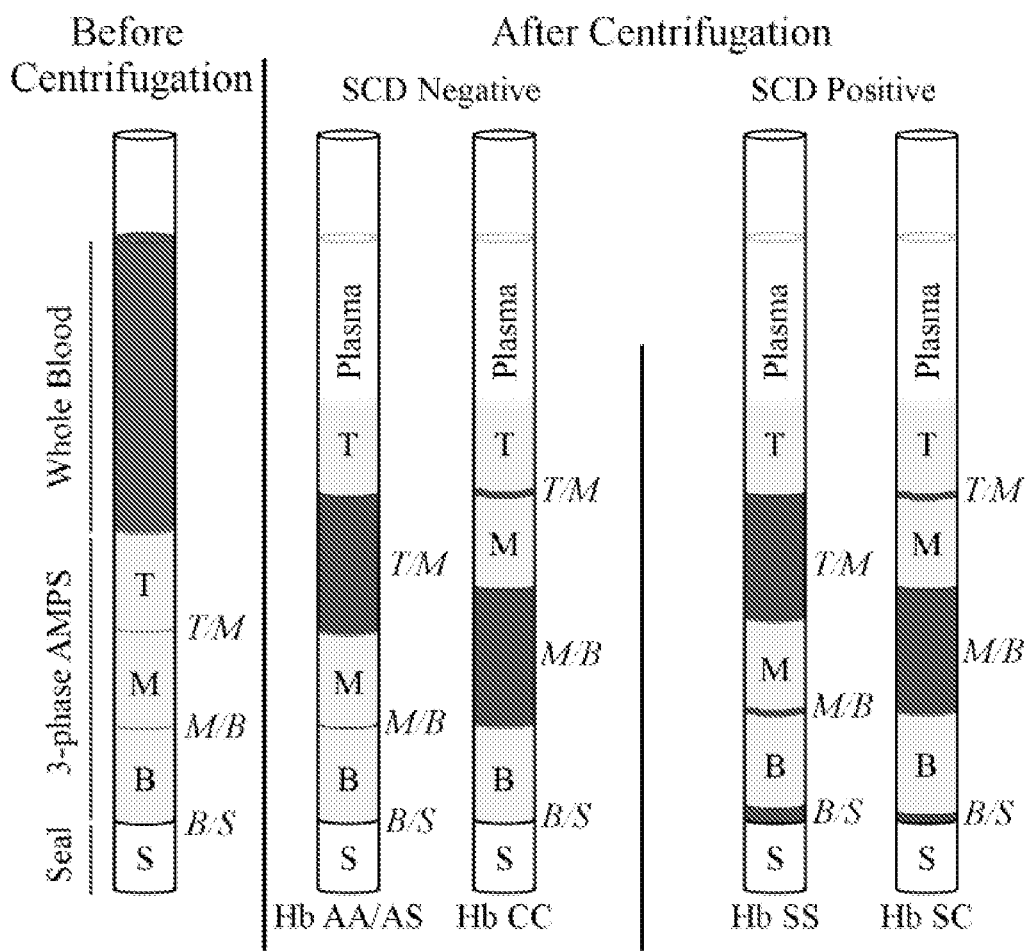
FIG. 15 is the schematic representations for the four most important outcomes of a density-based rapid test for sickle-cell disease.

The number of sub-populations of erythrocytes of interest determines the number of phases that should be used (see Supporting Information for Diagnosis of Sickle Cell Disease). An AMPS with three fluid phases provides enough interfaces—two liquid-liquid interfaces and a liquid-container interface—to separate the three populations of erythrocytes required in a test for SCD that can distinguish subtypes of the disease (FIG. 15). FIG. 15 is a schematic representation for the four most important outcomes of a density-based rapid test for sickle-cell disease. Upon centrifugation, erythrocytes move through the top (T), middle (M), and bottom (B) phases of the AMPS and collect at some combination of the three lower interfaces (two liquid/liquid interfaces, T/M and M/B, and one liquid/container interface, B/S). The distribution of cells between these interfaces will depend on the genotype; non-sickle hemoglobins (Hb AA, Hb AS, and Hb CC) are distinct from sickle hemoglobins (Hb SS and Hb SC). In all cases, the presence of red at B/S indicates sickle cell disease. Three interfaces allow further discrimination; a majority of erythrocytes at M/B indicates Hb SC or Hb CC. An AMPS with two phases provides two well-defined interfaces: one liquid-liquid interface between the phases, and one liquid-container interface. These interfaces are sufficient to separate dense, sickled cells from un-sickled erythrocytes, and to provide a test for SCD. Like the three-phase system depicted in FIG. 15, the presence of red cells at the bottom of the tube indicates a positive test for SCD. The simplicity of interpreting only two phases comes at the cost of the inability of this test to distinguish subtypes (Hb SS and Hb SC) of SCD.

The densities of the sub-populations of erythrocytes determine the desired densities of the phases of these AMPSs (see Supporting Information for Diagnosis of Sickle Cell Disease). Although the density distribution of erythrocytes in SCD has been studied extensively, commonly used methods of separating cells by density are not suitable for use in field settings (see Supporting Information for Diagnosis of Sickle Cell Disease). Methods that separate multiple populations require tediously layered gradient systems that are destroyed by agitation or mixing, and simple systems can only separate a single population. Centrifugation through AMPSs allows the separation of multiple populations in a thermodynamically stable (and, thus, simple to use) system.

When designing an AMPS, we first seek systems whose phases are separated by the same differences in density as our target sub-populations of erythrocytes. We then use other additives to tune the overall density to the necessary levels.

An AMPS formed by mixing 7.0% (w/v) poly(ethylene glycol) (PEG) with a molecular weight (MW) of ~20 kD and 10.3% (w/v) Ficoll with a MW of ~400 kD provided phases with densities separated by the values required for a two-phase system useful in the diagnosis of SCD. An AMPS comprising 3% (w/v) PEG with a MW of ~20 kD, 10% (w/v) dextran with a MW of ~500 kD, and 5% (w/v) polymer of partially hydrolyzed poly(vinyl acetate) (containing 75% —OH and 25% —OCOCH$_3$ groups) with a MW of ~3 kD, provided phases separated by differences in density of the values required for our three-phase assay.

We added NaCl to make the system isotonic (as measured by vapor pressure osmometry) with blood. We used a low-osmolality, high-density additive (Nycodenz, Accurate Chemical), to increase the density of each system to the proper range, and measured the density of each phase using an oscillatory U-tube densitometer. SCD-AMPS-2 contained 9.1% (w/v) Nycodenz and had phases with densities $\rho_{top}$=1.078 g cm$^{-3}$ and $\rho_{bot}$=1.129 g cm$^{-3}$. SCD-AMPS-3 contained 8.7% (w/v) Nycodenz and had phases with densities $\rho_{top}$=1.077 g cm$^{-3}$, $\rho_{mid}$=1.108 g cm$^{-3}$, and $\rho_{bot}$=1.120 g cm$^{-3}$.

A Point-of-Care Test Imposes Cost and Time Constraints on the Assay Design.

Figure 16:
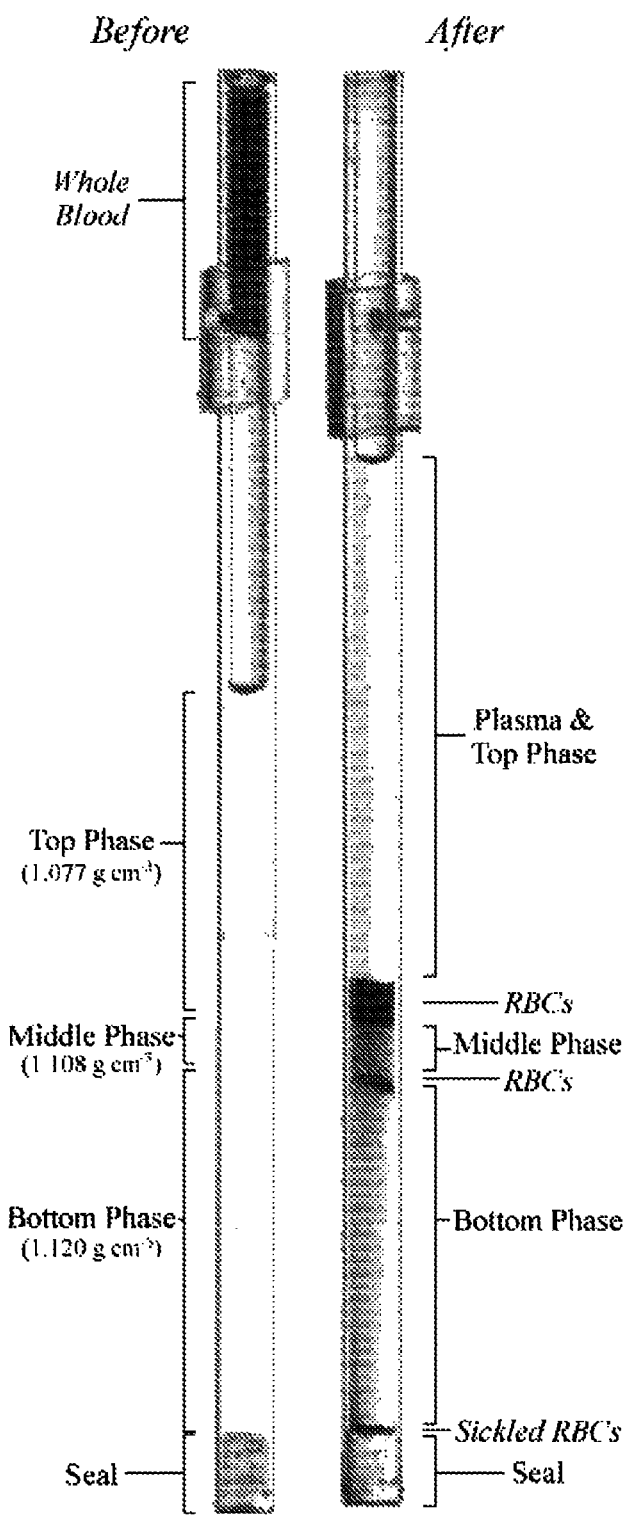
FIG. 16 is an example of an SCD-AMPS-3 rapid test loaded before and after centrifugation of blood from a sample without sickle cell disease.

To demonstrate the potential use of our tests in point-of-care settings, we designed them to use ~5 μL of blood (a volume easily obtained from a finger stick). This blood was added to a plastic capillary that had been preloaded with 14 μL of the SCD-AMPS-3 or SCD-AMPS-2 (FIG. 16). FIG. 16 is an example of an SCD-AMPS-3 rapid test loaded before and after centrifugation of blood from a sample without sickle cell disease. Blood wicks just past the hole in the side of the tube that is then covered with the silicone sleeve. After centrifugation, the cells separate from the plasma and pack between the phases of the AMPS. The test shown would be classified SCD positive because there is red below the bottom phase and above the seal. We sealed the capillaries with either white clay sealant—for ease of visual detection—or epoxy—for clarity when imaging tubes by transmission-mode in a scanner. Volumes were dictated by the capacity of the capillaries (see Supporting Information). The total cost of reagents and materials per test is ~$0.20 at this scale; when fabrication costs and packaging materials are accounted for, the cost per test is ~$0.50 (Table 5).

Figure 19:
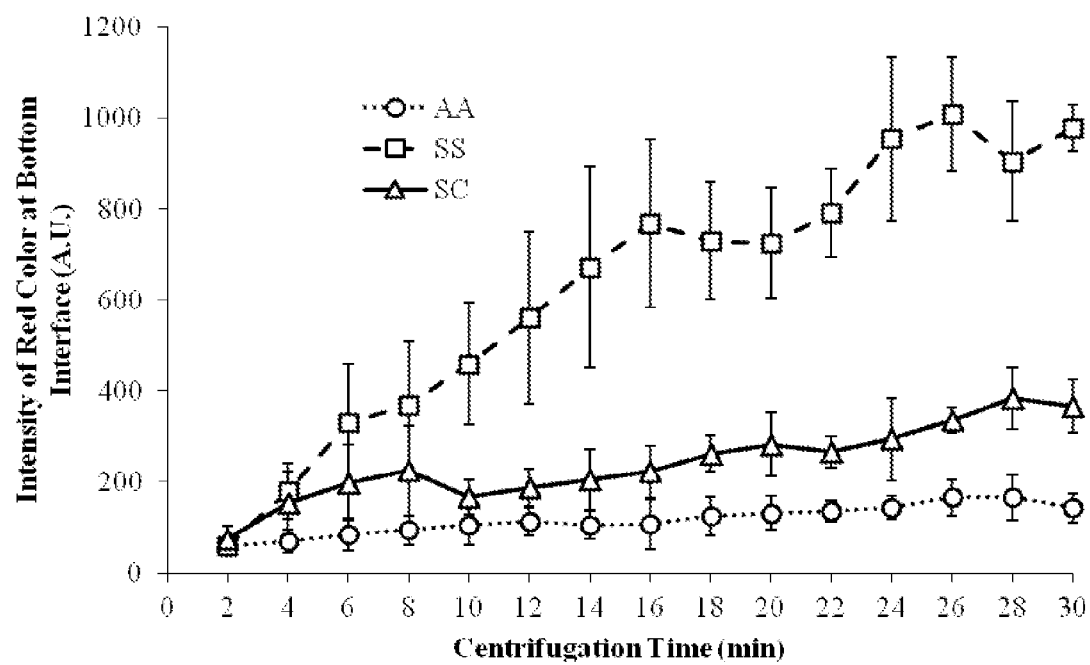
FIG. 19 shows the intensity of the red color at the bottom interface of the SCD-AMPS-3 system increases with centrifugation time.

In rural settings, patients may travel for a day to seek medical care, and follow-up is challenging. Tests that can be coupled to actionable information and counseling must be rapid (ideally under 30 minutes). To meet this condition, we used a microhematocrit centrifuge (CritSpin, Iris Sample Processing) to centrifuge samples at 13,000 g; this centrifuge can perform 12 tests at a time and, with a simple, DC-to-DC converter can be powered by a car battery. We could distinguish blood of individuals with SCD from normal blood after six minutes; additional time in centrifugation enhanced the signal (FIG. 19). FIG. 19 shows the intensity of the red color at the bottom interface of the SCD-AMPS-3 system increases with centrifugation time. We evaluated a set of six replicates digitally from samples of Hb AA (AA, n=4), Hb SS (SS, n=2), and Hb SC (SC, n=3) at two minute increments of centrifugation. Error bars depict the average deviation from the mean value of the intensity of the red color from the different subjects. After six minutes, the signal from SCD positive samples (SS and SC) are distinguishable from SCD negative samples (Hb AA). The separation, in general, increases over time. Notably, blood with Hb SS has a significantly higher signal than Hb SC over time. We chose to use ten minutes for our test to ensure a strong positive response, while keeping the test rapid. The rest of the procedure, including the finger-stick, sample loading, and test interpretation, took less than two minutes. By comparison, the gold standard for analysis of SCD, hemoglobin electrophoresis, requires more than three hours to prepare samples, run electrophoresis, stain, and wash. Laboratories often batch samples to run on a single gel and report results several days later.

In addition, ease-of-use is a critical component of a point-of-care test. Capillary action provides a simple mechanism to load blood. Designing a test to diagnose SCD from a finger-stick required a method to load blood into a capillary pre-loaded with SCD-AMPS and sealed on one end. Without modification, capillaries with closed ends will not wick additional fluid due to air trapped between the fluid and the sealed end. We used a "hole-in-tube" method to load blood into the capillary; puncturing a small hole in the side of the polycarbonate capillary at a specific distance from one end allowed a standard volume of blood (~5 µL) to wick into the tube (FIGS. 20A-20B). Specifically, FIGS. 20A-20B show two designs to load blood samples into a capillary that has been preloaded with SCD-AMPS-3 and sealed. In the "tube-in-tube" method (A), a small capillary with a ring of epoxy around it fills with blood by capillary action. This small tube can then be loaded into the larger capillary. In the "hole-in-tube" method (B), a small hole allows blood to wick into the prefilled tube. A silicone sleeve prevents the blood from leaking during centrifugation.

Centrifugation of Blood Through the SCD-AMPS Provides a Visual Separation of Sickled Cells.

Figure 21:
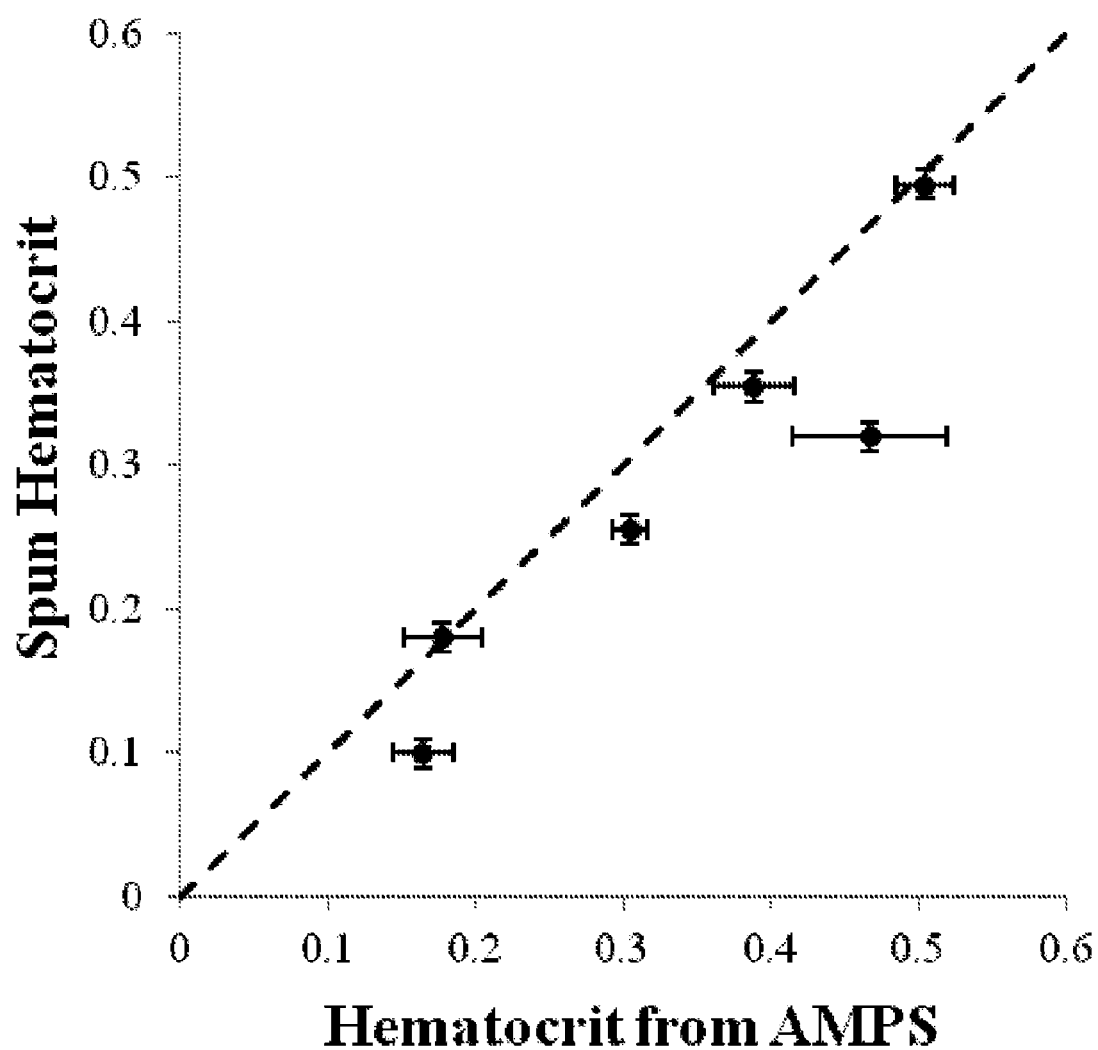
FIG. 21 shows the hematocrit measured in AMPSs provides an estimate of the spun hematocrit.
Figure 24:
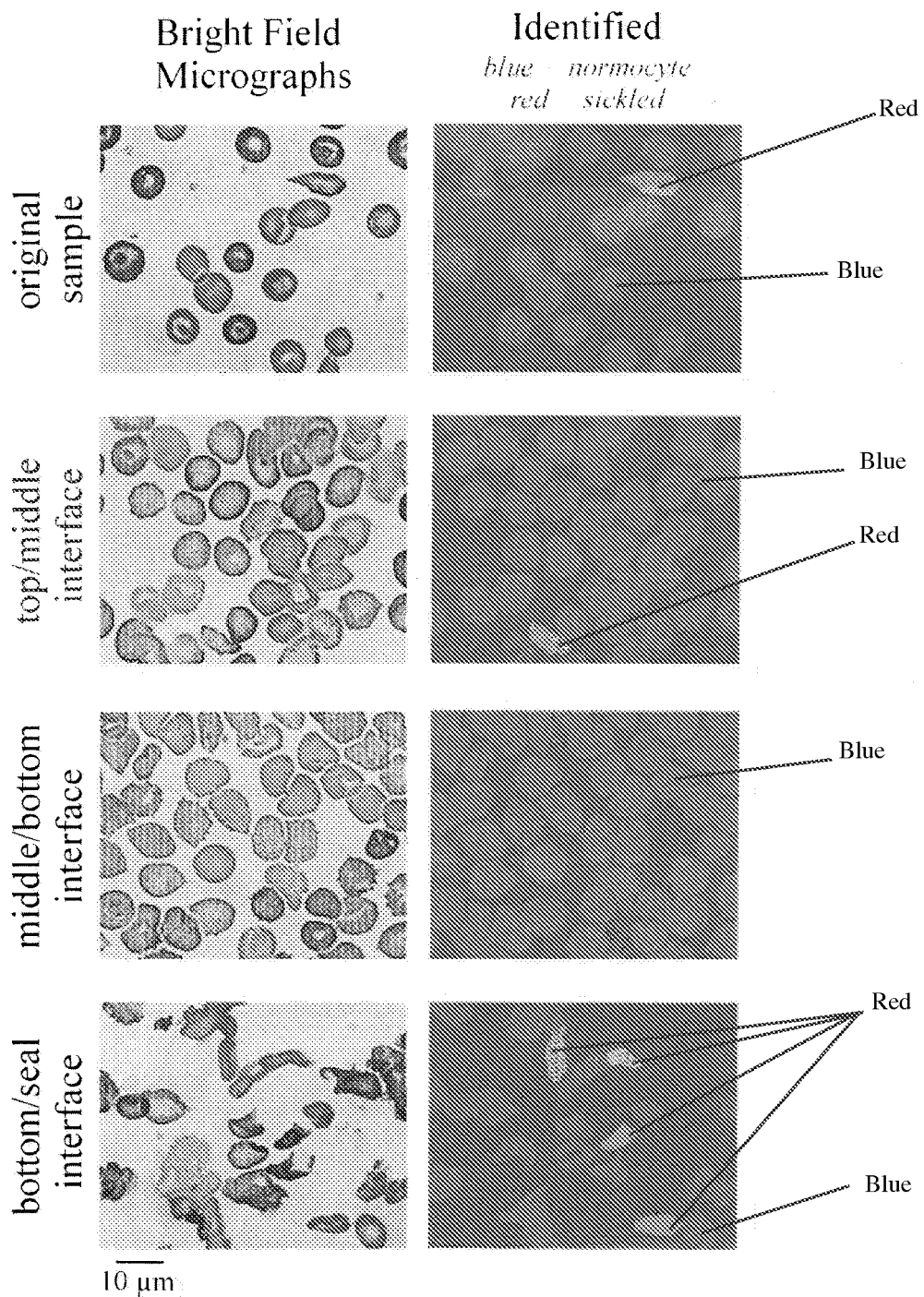
FIG. 24 shows micrographs of blood from the different fractions of a sample with Hb SS run on SCD-AMPS-3 test evaluated digitally to quantify sickling.

Over ten minutes of centrifugation at 13,000 g, blood moved out of the loading zone and separated through the AMPS and formed layers at the interfaces (FIG. 16). In most cases, the boundary between the top phase and the plasma was not distinguishable. The total packed volume between each interface provides an estimate of the hematocrit (FIG. 21): this estimate also provides a simple, if crude, method to identify severe anemia concurrently. Specifically, FIG. 21 shows the hematocrit measured in AMPSs provides an estimate of the spun hematocrit. A range of hematocrits was made by mixing packed cells with homologous plasma. The estimated hematocrit from AMPS is generally a slight overestimate of the real hematocrit because at 10 minutes, the cells are not completely packed. In general, we could distinguish samples with SCD from normal samples; a layer of red cells sat below the bottom phase of both SCD-AMPSs, and packed against the seal of the capillary (FIG. 17); this layer was dominated by sickled and dehydrated cells (FIG. 24). By comparing the volume of the packed cells above the seal to the volume of cells at the other interfaces, we could quantify the percentage of dense cells (Table 6).

Figure 17:
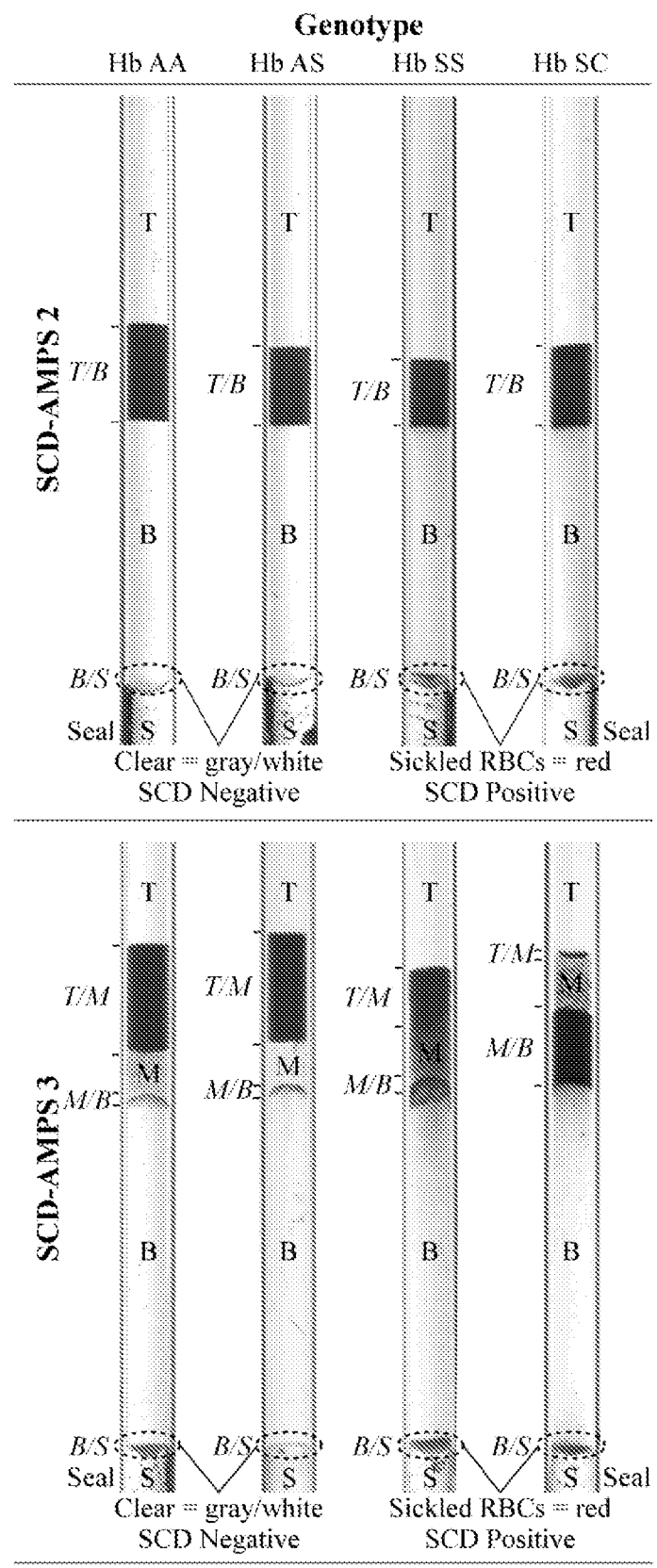
FIG. 17 shows the representative examples of positive and negative tests in the SCD-AMPS-3 ($\rho_{top}$=1.077 g cm$^{-3}$, $\rho_{mid}$=1.108 g cm$^{-3}$, $\rho_{bot}$=1.120 g cm$^{-3}$) and the SCD-AMPS-2 ($\rho_{top}$=1.078 g cm$^{-3}$, $\rho_{bot}$=1.129 g cm$^{-3}$), shows a clear distinction between subjects with SCD (Hb SS and Hb SC) and those without SCD (Hb AA and Hb AS).

Specifically, FIG. 17 shows representative examples of positive and negative tests in the SCD-AMPS-3 ($\rho_{top}$=1.077 g cm$^{-3}$, $\rho_{mid}$=1.108 g cm$^{-3}$, $\rho_{bot}$=1.120 g cm$^{-3}$) and the SCD-AMPS-2 ($\rho_{top}$=1.078 g cm$^{-3}$, $\rho_{bot}$=1.129 g cm$^{-3}$), show a clear distinction between subjects with SCD (Hb SS and Hb SC) and those without SCD (Hb AA and Hb AS). In non-SCD blood in the SCD-AMPS-2 system, all cells pack at the liquid interface (T/B). In the SCD-AMPS-3 system, most cells have normal morphologies and densities (normocytes) and pack at the upper liquid interface (T/M), the densest normal shaped cells (dense normocytes) collect at the lower liquid interface (M/B), and some aggregated platelets are present at the bottom of the tube (gray) (B/S). Erythrocytes from a subject with SCD display greater heterogeneity at high densities. Dense, sickled cells form a layer below the bottom phase of both SCD-AMPS on top of the sealant (B/S). In the SCD-AMPS-3 test, the distribution of cells between the liquid interfaces (T/M and M/B) differentiates Hb SS from Hb SC. The difference in the total packed volume of the cells demonstrates the difference in the hematocrit between the normal subject and the anemic subject with SCD. FIG. 24 shows micrographs of blood from the different fractions of a sample with Hb SS run on SCD-AMPS-3 test is evaluated digitally to quantify sickling. Identified cells are classified as normocytes (blue) or sickled (red). The cells at the bottom interface (bottom/seal) are markedly more sickled and dehydrated.

Figure 25:
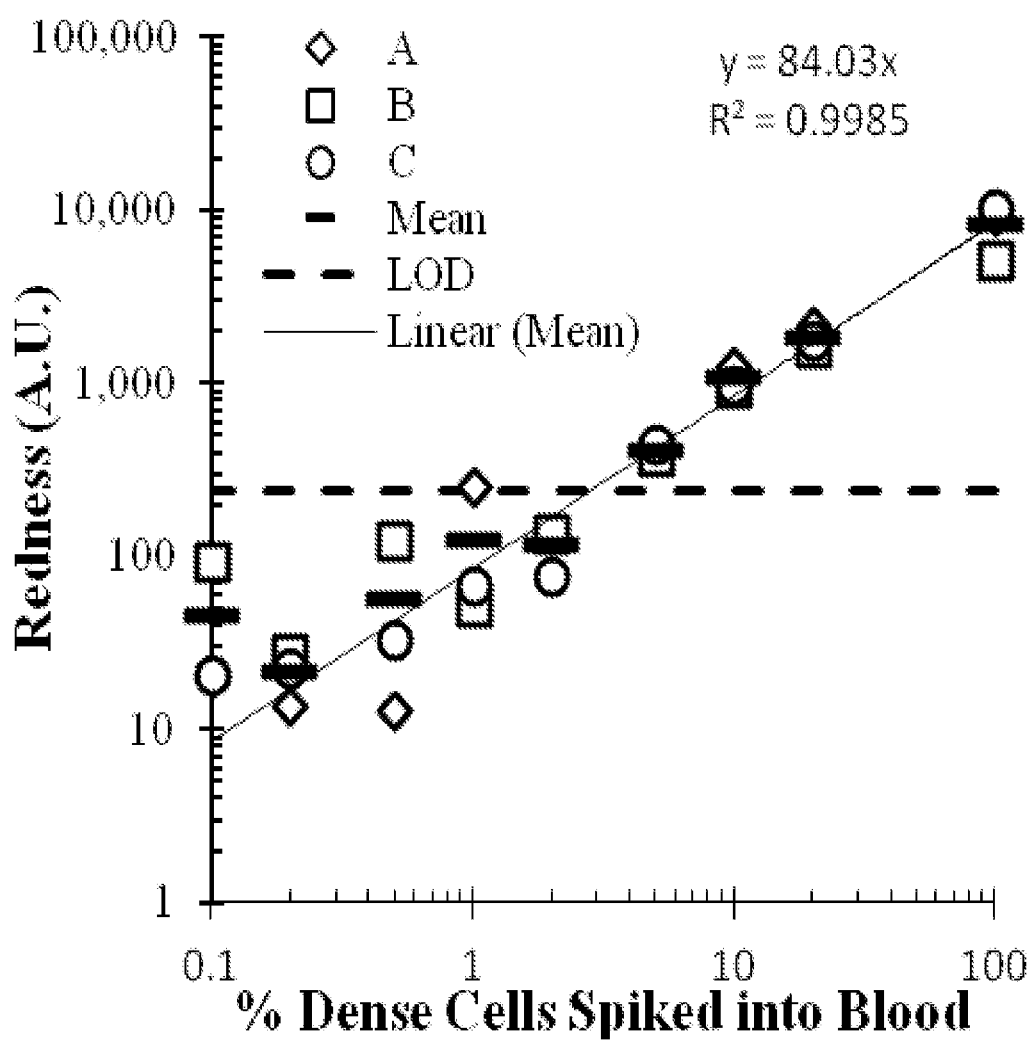
FIG. 25 shows measuring the intensity of red color at the bottom of the SCD-AMPS-3 can detect dense erythrocytes in whole blood at a concentration of 5%.

In the SCD-AMPS-3, most erythrocytes within the normal density range sat at the upper liquid/liquid interface. The densest normal erythrocytes (~1-5% of erythrocytes) collected at the lower liquid/liquid interface. In both SCD-AMPS-2 and SCD-AMPS-3, blood from individuals with sickle-cell trait appeared the same as that from normal individuals; our method does not differentiate between Hb AS and Hb AA genotypes. Although a small amount of sickled cells may exist in blood from an individual with Hb AS, the amount is below our estimated limit of detection of 2.8% dense, sickled cells (FIG. 25). FIG. 25 illustrates a method of measuring the intensity of red color at the bottom of the SCD-AMPS-3 which can detect dense erythrocytes in whole blood at a concentration of 5%. Erythrocytes from three donors (A-C) were treated with nystatin to be dense and dehydrated, and then spiked into untreated blood at known concentrations. After centrifugation in a tube containing the SCD-AMPS-3, the tests were scanned and analyzed to quantify the presence of dark red bands below the bottom phase. The limit of detection (dashed line) was established as three standard deviations above the mean measured on normal blood (n=7).

The Presence of Cells with a High Density Correlates with the Presence of SCD.

Samples that had a visible red band at the bottom of the AMPS correlated strongly with the presence of SCD. Conversely, samples negative for SCD rarely had red cells visibly present at the bottom of the AMPS (Table 7). The SCD-AMPS-2 had a true positive rate (sensitivity) of 90% with a Jeffreys 95% confidence interval (C.I.) of 73%-98% and a true negative rate (specificity) of 97% (C.I.=86%-100%). The SCD-AMPS-3 had a sensitivity of 91% (C.I.=78%-98%), and a specificity of 88% (C.I.=74%-98%). Admittedly, visual inspection allows room for bias in a diagnostic test. To reduce biased evaluation, each test was evaluated independently by at least two people. Samples negative for SCD included both Hb AA (n=26 for SCD-AMPS-3, n=24 for SCD-AMPS-2) and Hb AS (n=7). Samples positive for SCD included Hb SS (n=20 for SCD-AMPS-3, n=15 for SCD-AMPS-2) and Hb SC (n=6). The formulation of SCD-AMPS-2 was finalized after testing had begun on SCD-AMPS-3 and, thus, the system was tested on fewer samples.

In about half of all tests where a clear red band was not present at the bottom of the tube, we found a thin layer of white, yellow or pink material upon visual inspection. Evaluation of these layers by microscopy revealed that platelets had clumped together to form large aggregates (FIGS. 23A-23D). FIGS. 23A-23D illustrate an example of white pellet found at the bottom of some of the samples from Hb AA subjects. A tube-in-tube version of the SCD-AMPS-3 test is negative for SCD (a.). Although the bottom is not red, there is a substantial gray layer above the above the white clay seal (dark gray in transmission imaging) (B/S) (d.). Micrographs (b. and c.) reveal a large number of platelets and cell aggregates. In some cases, these aggregates appeared to have captured a small number of both red and white blood cells. In samples without SCD, we believe these aggregates may occasionally capture enough red blood cells to create a false positive.

Figure 18:
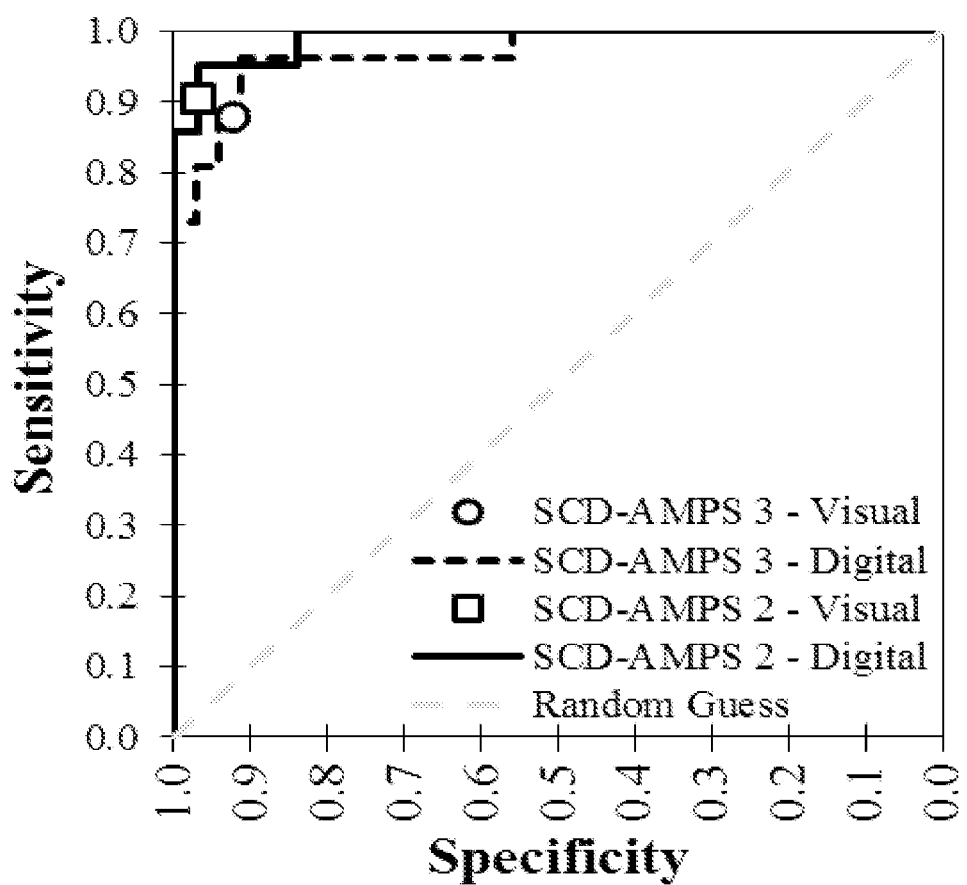
FIG. 18 shows the receiver operating characteristic (ROC) curve (solid line) for the digital evaluation of the presence of a red layer at the bottom of the SCD-AMPS which demonstrates good diagnostic performance.

We also evaluated scanned images of the capillaries digitally. Varying the thresholds for the intensity of the red color at the bottom of the tube produced a receiver operating characteristic (ROC) curve (FIG. 18) (see Supporting Information for Diagnosis of Sickle Cell Disease). FIG. 18 shows the receiver operating characteristic (ROC) curve (solid line) for the digital evaluation of the presence of a red layer at the bottom of the SCD-AMPS which demonstrates good diagnostic performance. Both curves are far from the gray line that indicates no ability to detect an event. Visual evaluation of the rapid tests matched the sensitivity and specificity of the digital analysis. Our sensitivity and specificity from visual evaluation matched the ROC curve for both tests; this finding suggests that, with proper training, the visual reading of the tests by health workers could match the performance of the digital analysis.

In Hb SC, un-sickled cells have a slightly higher density than un-sickled cells in Hb SS. In SCD-AMPS-3, blood from most individuals with Hb SC had a distinct distribution of red cells from those with Hb SS. In half the cases, a thick band of red cells at the lower liquid interface whose height was comparable to or greater than that of the band of red cells at the upper interface (FIG. 16). In some cases, an hour glass shape of red cells connected the packed cells at the two interfaces (FIG. 26). FIG. 26 illustrates examples of the patterns of red cells at the liquid interfaces for Hb SC and Hb SS in the SCD-AMPS-3 system. Four representative examples of the layers of red blood cells from samples with Hb SS show the characteristic pattern of the majority of cells packed at the upper liquid/liquid interface with a thin packed band at the lower liquid/liquid interface. All six samples with Hb SC are shown after 10 minutes of centrifugation. Samples Hb SC-4, 5, and 6 all have red bands at the lower liquid interface that are comparable to or greater than the bands at the upper liquid interface. Sample Hb SC-3 has a significant pack of cells at the lower liquid interface, an hour glass shape of red cells between the two liquid interfaces. Sample Hb SC-2 packed to a pattern more similar to Hb SC-3 and 4 after 20 total minutes of centrifugation. By contrast, blood from samples with Hb SS had two distinct bands of red with a clear majority of red cells at the upper liquid interface. These differences in the distribution of cells allowed us to distinguish visually between Hb SC (n=6) and Hb SS (n=20), the two predominant forms of SCD with a sensitivity of 67% (C.I.=29%-92%) and a specificity of 100% (C.I.=88%-100%). Centrifugation for an additional 10 minutes increased the sensitivity to 83% (C.I.=44%-98%).

Figure 22:
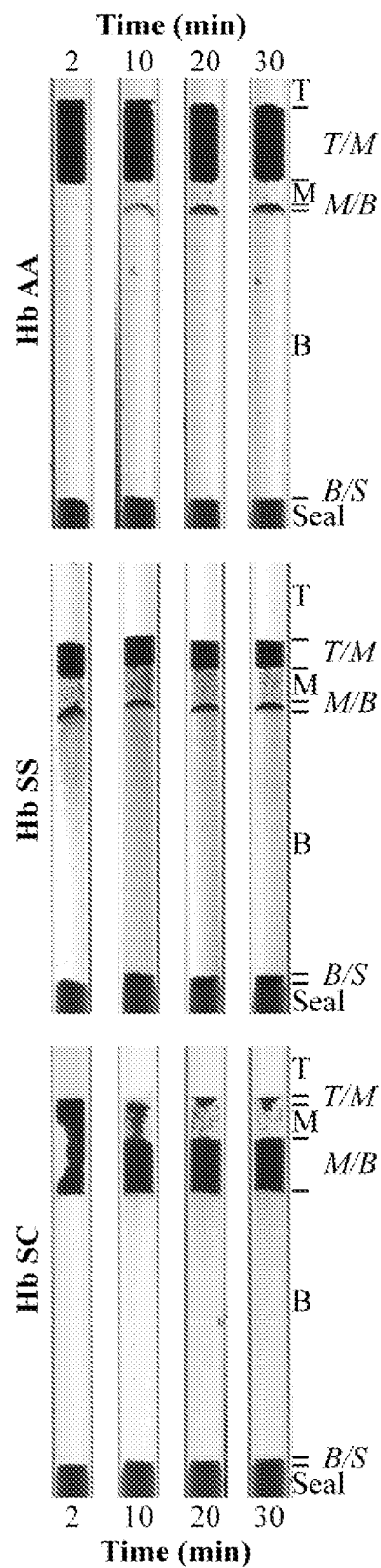
FIG. 22 shows additional centrifugation time results in clearer separation of the cells.

In FIG. 17, the red and pink, in the lower phases, indicated, either that the dense cells had not all reached their equilibrium position or that some cells had the same density as one of these phases. Additional centrifugation time (a total of 30 minutes) allowed these cells to sediment further and increased the layer of red at the bottom of the tube (FIGS. 19 & 22), but required more time. FIG. 22 illustrates additional centrifugation time results in clearer separation of the cells. Some isodense cells remain unchanged after 30 minutes (Hb SS). Hb SC is easily distinguished from Hb SS after 20 minutes. The pack of cells above the white clay seal (dark gray in transmission imaging) increases over time (Hb SS and Hb SC). For a diagnostic test, however, we do not need all the cells to reach their equilibrium positions as long as the difference between positive and negative tests is clear.

An AMPS-Based Test for SCD is Appropriate for Use at the Point-of-Care.

The World Health Organization (WHO) has defined the ASSURED criteria as guidelines for the development of point-of-care devices. Devices should be affordable, sensitive, specific, user-friendly, reliable, equipment-free, and deliverable to those in need. AMPS-based tests for SCD should come closer to achieving these goals than screening methods that are currently available. The AMPS-based method also compares favorably to unconventional technologies that have been recently developed to diagnose SCD (Table 8).

Currently, the most used, microscope-free methods for screening for sickle-cell disease in low-resource settings are solubility tests, such as Sickledex. In these tests a solution lyses and deoxygenates the blood; the reduced solubility and polymerization of deoxyhemoglobin S causes the hemoglobin to cloud the solution. These tests can detect the presence of Hb S, but cannot distinguish between Hb SS and Hb AS without the use of additional equipment (i.e., a turbidimeter); this difference is non-trivial, as the former is a life-threatening condition, and the latter is, largely, benign.

Our method provides an information-rich test that can be used at the point-of-care. The "hole-in-tube" method allows blood to fill the tube automatically. Unlike tests that require lysing and incubating blood in a solution, whole blood is tested directly. Minimal handling of the sample reduces errors and risks to health workers performing the test. We estimate the cost per test to be $0.50 (see Supporting Information). The centrifuge (CritSpin, Iris Sample Processing) we use in this study costs approximately $1,600, but we have verified that our system performs similarly on a basic centrifuge (SpinCrit, www.spincritcentrifuge.com) that costs $150, is portable, and runs on four AA batteries; this centrifuge can perform six tests at a time and standard AA batteries allow three separate 10 minutes spins per charge. Simple centrifuges, such as those that use mechanical actuation, solar power, or batteries, should allow this test to reach rural and mobile clinics; slower centrifuges, however, would require longer times for the tests.

Even with simplicity and low cost, AMPS-based tests still attain a sensitivity and specificity near 90%. Although they do not distinguish between Hb AS and Hb AA, they can distinguish between Hb AS and both Hb SS and Hb SC. SCD-AMPS-3 has the added ability to distinguish Hb SC from Hb SS, albeit with a lower sensitivity than that with which the test identifies SCD—the sensitivity to identify Hb SC may be improved with a slightly different density of the middle phase. In addition to providing diagnostic information, these tests measure a biophysical indicator that may help identify patients more likely to experience certain complication of the disease; the fraction of erythrocytes that are dense, sickled cells correlates with certain clinical manifestations of SCD (e.g., skin ulcers, priapism, and renal disfunction). Monitoring the distribution of the density of cells could also provide a way to assess sickle crises.

Fractionating red blood cells by density in step gradients generated using AMPSs provides a new method to diagnose SCD. The presence of dense, sickled cells correlates with the presence of SCD; AMPSs provide a self-assembling step-gradient in density that makes the identification of dense cells accessible in low-resource settings. Compared to currently available techniques, the density-based tests using AMPS combine four desirable properties: i) fieldability—they are amenable to use at the point-of-care, ii) performance—they can distinguish Hb SC and Hb SS from Hb AA or Hb AS, iii) biophysical information—by quantifying the percentage of dense, sickled cells, and iv) low cost.

At birth, children with SCD have predominantly Hb F, and generally begin to express appreciable amounts of Hb S between six months and one year of age. The presence of sickled cells relies on the presence of large amounts of Hb S; we expect a density-based test, therefore, to have significantly lower sensitivity in newborns than in one-year olds. Only one of our Hb SS samples came from a child under one year old, and it appeared negative on both digital and visual inspection. Developing an accessible and affordable screening test for newborns remains a critical, unmet challenge. Rapid diagnostics that rely on the presence of sickled cells, such as ours, can play an important role in reducing child mortality if screenings are done near a child's first birthday; such diagnostic efforts could be carried out simultaneously with vaccination campaigns (e.g. measles) that target children between nine months and one year old.

By combining simplicity and rapidity to measure a biophysical parameter (i.e., density), the density-based test using AMPSs could play an important role in diagnosing SCD at the point-of-care. Measuring the fraction of dense cells at the bottom of an SCD-AMPS could also have use beyond the diagnosis of SCD, and possibly aid in the management of the disease, but such uses will require clinical validation.

More generally, density-based diagnostics illustrate how biophysical markers, such as density, and biophysical techniques, can combine to provide simple and low-cost health solutions; AMPS-based separations of blood should enable hematology at the point-of-care.

Supporting Information for Diagnosis of Sickle Cell Disease

Nystatin Treatment for Model Sickle System.

We created dehydrated erythrocytes using the nystatin loading procedure developed by Canessa. When nystatin is present, the membrane of erythrocytes becomes permeable and the volume of the cell can be set by adjusting the osmolality of the solution with additives like sucrose. Washing to remove the nystatin returns cells to a less permeable membrane while retaining the adjusted volume. Cells were washed five times in a choline wash solution of 150 mM choline chloride, 1 mM $MgCl_2$, and 10 mM Tris HCl and MOPS with a pH adjusted to 7.4 at 4° C. We then exposed the cells to nystatin in a nystatin loading solution containing 10 mM NaCl, 130 mM KCl, and 200 mM sucrose for 20 minutes at 4° C. This solution was spun down and the supernatant removed. We incubated the cells in loading solution (without nystatin) for 10 minutes at 37° C. followed by four washes with the loading solution at the same temperature. Finally, we washed the cells five times in the choline wash solution at 4° C. We suspended packed cells in homologous plasma at the same hematocrit as the original blood and made serial dilutions to attain a range of percentages of dense cells of blood from each donor.

TABLE 5

Itemized cost per test estimated for production.

| Item | Unit Cost |
| --- | --- |
| Polycarbonate capillary tube | $0.1000 |
| Critoseal | $0.0027 |
| Critocaps | $0.0415 |
| Silicone sleeve | $0.0079 |
| Glue (Krazy Glue) | $0.0033 |
| Polymer solutions | $0.0032 |
| Foil-lined Pouch (12 devices/pack) | $0.0625 |
| Total Consumable | $0.2211 |
| Total Manufacturing Equipment & Personnel | $0.2756 |
| Total Cost | $0.4967 |

Digital Evaluation of Rapid Tests.

To capture comparable digital images of all our rapid tests, we used a digital scanner in transmission mode (Epson Perfection V330 Photo) to record images of up to 12 tubes at a time placed in a plastic grid. We then used custom written Matlab code to process and analyze the images through several steps: i) scanned images were matched to a key image file using image registration and cropped to a standard size, ii) the matched images were cropped at twelve positions into separate image files for each tube, iii) images were converted into the Lab colorspace, iv) the region of interest that contained the bottom of the tube was selected, v) each pixel was evaluated for the intensity of the red color through a combination of intensity and distance in the Lab space from a training set of red, vi) the scores for all pixels were summed to give a single score for each tube, and vii) the calculated values for each tube were written to a file for further analysis and comparison.

The Lab colorspace is designed to approximate human vision so we chose to use this colorspace over other schemes, such as RGB and CMYK. We then defined a range of acceptable red colors using a training set of sickle cell positive samples and using a weighting scheme to evaluate the distance in the colorspace from the learned red color. We used the "L" component, or lightness, to weight the density of the packed red cells so that darker packed red would count more strongly than a light red that was present when cells were not packed.

Statistical Methods.

Sensitivity is defined as (# true positives)/(# true positives+# false negatives). Specificity is defined as (# true negatives)/(# true negatives+# false positives). We chose to use Jeffreys confidence intervals because our values were near the upper bounds of 100% sensitivity or specificity.

Experimental Details

AMPS Phases for Separations.

An AMPS with n phases has a total of n+1 interfaces (AMPS/container, n−1 AMPS phase/phase, and AMPS/air) at which to separate objects. For practical applications where blood is layered on top of an AMPS, and centrifugation is used to separate cells at the interfaces between the phases of the AMPS, the top (AMPS/serum) interface is diffused and not useful for separations in this application; there are, therefore, n sharp interfaces that can concentrate cells.

Erythrocytes have a Distribution of Densities that is Specific to Sickle-Cell Disease.

Sickled cells have a mass density ($\rho \sim 1.12$ g $cm^{-3}$) that is higher than the most dense erythrocytes in healthy individuals ($\rho_{max} \sim 1.10$ g $cm^{-3}$) (2-5); the difference in density between normal and sickle-cells makes SCD a strong candidate for a density-based diagnostic test.

The percentage of cells that are dense and sickled in the blood varies among individuals. Under most conditions, however, the blood of individuals with SCD has 13% (S.D. 8%) dense cells. A notable exception comprises individuals that express a significant amount of fetal hemoglobin (Hb F); in these individuals, sickled cells comprise a smaller proportion of erythrocytes and clinical symptoms are normally milder than others with SCD.

Hemoglobin C disease (Hb CC)—much more rare and geographically isolated than SCD—also increases the mass density of erythrocytes, and constitutes a potentially confounding interpretation. In Hb CC, the entire distribution of densities of erythrocytes shifts to a slightly higher density; reticulocytes in Hb CC are more dense than those in Hb AA, but the high-density erythrocytes in Hb CC are less dense than the densest cells in Hb SS. In sickle-cell disease, erythrocytes that are not sickled remain at normal densities, and the erythrocytes exist in two populations: a high-density sickled population (~10% of cells) and a lower-density un-sickled population, which also comprises reticulocytes and the youngest erythrocytes.

Densities of Erythrocytes Determine the Densities of the Phases.

A bottom phase, with a density of $\rho \geq 1.120$ g cm$^{-3}$, should permit dense, sickled cells ($\rho \geq 1.12$ g cm$^{-3}$) to sediment, while creating a barrier to the dense cells of Hb CC blood ($\rho_{max} \sim 1.11$ g cm$^{-3}$). Although we were unable to test blood with Hb CC due to the rarity of this blood type in the United States, we designed both systems with sufficiently dense bottom phases so that future work with Hb CC could be done in areas (e.g., West Africa) with a higher prevalence of this genotype. The top phase must be less dense than low-density erythrocytes, such as reticulocytes ($\rho=1.085$ g cm$^{-3}$), to ensure that all the erythrocytes pack at a well-defined interface. In a three-phase system, a middle phase with a density of $\rho=1.110$ g cm$^{-3}$ will separate the main population of normal erythrocytes from the high-density tail of the distribution of cells. The middle phase of the three-phase system allows us to distinguish subtypes. In the case of Hb AA and Hb SS, we expected the majority of red cells to collect between the top and middle phase. In the case of Hb SC and Hb CC, however, the shift in the density of the population is seen by a dense band of red cells between the middle and bottom phase. Red cells are present below the bottom phase in both Hb SS and Hb SC. The pattern of the red bands at each interface distinguishes these different hemoglobin types (FIG. 15).

Several other factors could influence density in a way that could affect the performance of our AMPS-based tests. Patients suffering from sickle-cell disease with alpha thalassemia trait and alpha thalassemia may have fewer dense cells; one of our Hb SS samples had alpha thalassemia and it was distinguishable both visually and digitally as Hb SS in our test. Iron deficiency often leads to hypochromic, microcytic anemia; a SCD patient with iron deficiency anemia may have a more complex distribution of densities of erythrocytes. Testing on a larger population that might include patients with these and other concomitant conditions would determine the generality of density as a diagnostic for SCD.

Co-Solutes Tune the Osmolality and Density of an AMPS to Physiological Levels.

Any swelling or dehydration of erythrocytes that reduces the separation between the three sub-populations of interest may compromise a diagnostic test based on density. To maintain physiological conditions and prevent changes in volume of the cells, we wanted to maintain an osmolality that was isotonic with blood (~295 mOsm).

Achieving the densities necessary to separate sickled cells with polymers alone is difficult. High concentrations of polymer create viscous and hypertonic environments. For example, a solution of 30% (w/v) dextran (MW=500 kD) in a phosphate buffered solution has a density of 1.122 g cm$^{-3}$ and an osmolality of 336 mOsm. This system would dehydrate normal erythrocytes and could increase their density to be indistinguishable from sickled cells. To generate phases with high density that are isotonic with blood, co-solutes with high densities can be used to increase the density of an AMPS.

Separation Over Time.

In order to choose the time of centrifugation for our rapid test, we performed a time series experiment with the SCD-AMPS-3 system. Six replicates of the rapid test were loaded with blood (n=2 with Hb SS, n=3 with Hb SC, and n=4 with Hb AA). The tests were subjected to centrifugation for two minutes and then scanned in repeated iterations for a total centrifugation time of 30 minutes. The scanned images were then analyzed for the intensity of the red color at the bottom of each test (FIG. 19). After six minutes, both the Hb SS and Hb SC blood begin to collect significantly more red color at the bottom of the tube than the Hb AA blood. This difference gradually increases over time. To take advantage of this signal amplification without compromising the rapidity of our test, we chose to centrifuge our test for 10 minutes.

Rapid Test Capillary Tube Design.

We created two methods to load blood into a sealed tube that was preloaded with AMPS (FIG. 16). We have described the "hole-in-tube" method in the main text. Briefly, we use a pushpin in a custom-made alignment mold to puncture the side of the plastic capillary tubes at a specific point along the length of the tube to ensure a repeatable volume is added to all tubes. Air, which would otherwise be trapped and block capillary action, escapes through the hole. To prevent blood from escaping through the puncture during centrifugation, we slid a sleeve of silicone rubber over the hole.

The other method, tube-in-tube, relies on the use of a smaller glass capillary tube that fits within the larger, preloaded polycarbonate capillary (FIGS. 20A-20B). We used the smaller capillary to wick blood into a controlled volume and then introduced the smaller capillary directly into the larger capillary. A small ring of epoxy on the upper portion of the small capillary prevents the small capillary from entering the SCD-AMPS upon centrifugation. This method is fast, but requires some manual dexterity to load the smaller capillary into the larger one.

The tubes hold ~24 µL of liquid in addition to the seal. This provided a constraint to design the volume of our test. Double the volume of blood per test is reserved for loading the sample and then ensuring that once the sample passes into the AMPS, the combined volume is not higher than the hole in the side of the tube—we found that liquid above this level would occasionally leak out, and, if blood was being used, would present a biohazard. Early screening of AMPSs for the sickle test had used a volume ratio of blood to AMPS of 1:3. As we scaled down to the rapid test format, we needed to maintain this ratio to maintain a similar performance. Using 14 µL of AMPS and loading 4.7 µL of blood allowed us to satisfy all our constraints.

Fabrication.

We used calibrated micropipettors to fill tubes with the specific volume and then used the fill line to measure the distance we used. We used a custom built hole puncher to make repeatable holes (see *Materials and Methods*). By eye and by pipette the volumes filled were similar. From scans, we estimated the distance between the end of the capillary and the far end of the hole to have a coefficient of variance (CV) of less than 2%.

Hematocrit and Packing of Cells.

By comparing the volume that the cells occupied in these three regions to the volume of blood loaded, we can estimate hematocrit (FIG. 21). We measured the height of the packed cells in each area digitally (ImageJ) and compared it to the length from the hole in the side of the tube to the top of the tube. The low volume of blood used and slight variations in the volumes of the blood and AMPS only allow, however, for a coarse measure of hematocrit (±10%). In general, the hematocrit after 10 minutes in the AMPS was an overestimate of the real hematocrit. Additional centrifugation time improved the packing of the cells (FIG. 22) and could improve the hematocrit estimation.

Aggregates in Negative Samples.

To investigate the white or pink layer that occasionally formed at the bottom of negative samples, we examined the material by optical microscopy. We identified the samples to investigate by using the smaller rapid test format, but we could not extract enough material from these systems to identify the objects under a microscope. We, thus, scaled up the separation to a 1.5 mL Eppendorf tube, while maintaining the same ratio of blood to AMPS and comparable centrifugation parameters. After separation, we used a micropipettor to extract the layer of material below the bottom phase of the AMPS and stained a thin smear of the sample on a glass slide (FIGS. 23A-23D).

After centrifugation, we extracted and washed the cells from each interface of the AMPS. We made thin smears stained with Hemacolor (Harelco) to evaluate the morphological distribution of erythrocytes.

Using bright field microscopy we captured a series of images, which we then analyzed with CellProfiler™ (Broad Institute) to quantify the percentage of erythrocytes that were sickled in each interface. We classified a cell as sickled if the aspect ratio of the major axis length over the minor axis length was greater than 2. We found this measure to correlate well with sickled morphologies over several fields of view that we evaluated by eye (FIG. 24).

When using blood from a patient with Hb SS with a very low level of sickled cells (0.7%), we were able to visualize the presence of dense cells at the bottom of the SCD-AMPS in both the capillary tubes and the microcentrifuge tubes. The fraction of cells at the bottom phase/seal interface contained 7.3% sickled cells. Over half of the remaining cells appeared crenated and dehydrated, similar to the "holly wreaths" that result from deoxygenation of cells with Hb SS. Upon entering the SCD-AMPS, the erythrocytes may have deoxygenated. Rapid deoxygenation in Hb SS causes the formation of crenated cells and "holly-wreaths" instead of the classic sickle shape. Normal erythrocytes in the smears from the bottom fraction may be either cells that have been oxygenated during the washing step and returned to a normal morphology or normal cells that became engulfed by a mass of dense cells and trapped at the bottom of the tube. Interestingly, the cells at the upper and lower liquid/liquid interfaces had 4.4% and 4.7% sickled cells, respectively. These layers, however, did not contain crenated, dehydrated cells. The existence of cells with a high aspect ratio may have been a result of smearing cells from the polymer solutions, but the higher proportion of cells with high aspect ratios in the bottom layer suggests that there was a higher amount of sickled cells in the bottom population.

Quantification of Dense Cells.

To quantify the percentage of dense cells, we evaluated the digital images of the results from the SCD-AMPS-2 tests. Using digital analysis (ImageJ) we measured the height of the packed cells above the seal and the height of the packed cells at the liquid interface. We then calculated the percentage of dense cells for all the samples that had SCD (both Hb SS and Hb SC) (Table 6). Note that in two cases of Hb SS, we did not visually identify a band of red cells at the bottom and the calculated percentage of dense cells in these cases was zero. Of the 21 SCD samples that were tested on SCD-AMPS-2, the average percentage of dense cells was 10%.

Results by Genotype.

The sensitivity and specificity values described in the manuscript were based on binning all positives (Hb SS and Hb SC) together and all negatives (Hb AA and Hb AS) together. Table 7 details the results of visual evaluation of all four genotypes in this study. Five of the six Hb SC samples could be distinguished from Hb SS after evaluating the distribution of cells between the two liquid interfaces in SCD-AMPS-3. All Hb SS samples appeared as expected in FIG. 15; none of the Hb SS samples appeared with a majority of the red cells at the lower liquid interface.

TABLE 6

Quantification of the dense cells from the SCD-AMPS-2.

| Donor | Genotype | Visual Reading | Dense Cells |
|---|---|---|---|
| 1 | SS | Positive | 21% |
| 2 | SS | Positive | 15% |
| 3 | SS | Positive | 8% |
| 4 | SS | Positive | 16% |
| 5 | SS | Positive | 14% |
| 6 | SS | Positive | 10% |
| 7 | SS | Positive | 12% |
| 8 | SS | Positive | 12% |
| 9 | SS | Positive | 15% |
| 10 | SS | Positive | 11% |
| 11 | SS | Positive | 8% |
| 12 | SS | Positive | 13% |
| 13 | SS | Positive | 10% |
| 14 | SS | Negative | 0% |
| 15 | SS | Negative | 0% |
| 16 | SC | Positive | 8% |
| 17 | SC | Positive | 8% |
| 18 | SC | Positive | 10% |
| 19 | SC | Positive | 4% |
| 20 | SC | Positive | 9% |
| 21 | SC | Positive | 8% |
| Average | — | — | 10% |

TABLE 7

Visual evaluation of the SCD-AMPS for sample sizes of N.

| | SCD-AMPS-3 | | | SCD-AMPS-2 | | |
|---|---|---|---|---|---|---|
| Sample | N | Positive Rate[a] | Negative Rate | N | Positive Rate[a] | Negative Rate |
| Hb SS | 20 | 0.90 | 0.10 | 15 | 0.87 | 0.13 |
| Hb SC | 6 | 1.00 | 0.00 | 6 | 1.00 | 0.00 |
| Hb AA | 26 | 0.15 | 0.85 | 24 | 0.04 | 0.96 |
| Hb AS | 7 | 0.00 | 1.00 | 7 | 0.00 | 1.00 |

[a]Rates were calculated by comparing the results from the AMPS test to the known status of the subjects as measured by a gold standard (either Hb electrophoresis or HPLC).

Nystatin Provides a Means to Create Model SCD Blood.

Testing the diagnostic capabilities of the SCD-AMPS required samples of blood from SCD patients that had not been recently transfused (transfusion reduces the number of dense, sickled cells present in a patient's blood). To characterize the limit of detection of our system in a quantitative way we needed model dense cells whose behavior was less subject to change than sickle cells, we created dense erythrocytes by treating blood with nystatin, and exposing them to hypertonic media. This creates dense, dehydrated cells; we used these cells as a model of sickled cells.

We mixed known volumes of these dense cells with untreated blood to simulate SCD blood. The model blood contained small (cell volume <60 fL) cells (microcytic) with high concentrations of hemoglobin (hyperchromic), similar to sickled cells in SCD; after treatment, the erythrocytes from three blood samples had a mean corpuscular volume ranging from 67.3-71.5 fL, and mean corpuscular hemoglobin content ranging from 39.9-41.5 g dL$^{-1}$. When we mixed 5% of the treated cells with the original blood, the model samples had a mean corpuscular volume ranging from 81.9-83.9 fL, a mean corpuscular hemoglobin content ranging from 32.4-34.8 g dL$^{-1}$, and the percent of microcytic erythrocytes ranged from 2.6-3.8%.

Determination of the Limit of Detection Using a Model System for SCD.

Using normal blood (n=3) spiked with dense cells created by the nystatin treatment, we evaluated the bottom of the SCD-AMPS-3 for the presence of red color after 10 minutes of centrifugation. By eye, we could detect the presence of dense cells in normal blood at a concentration of 2% about half the time. At a concentration of 5%, a layer of red covered the bottom of the capillary. Most SCD patients have over 13% dense, sickled cells.

We also imaged the results of each test with a flatbed scanner in transmission mode (Perfection Photo V550, Epson). Image processing in Matlab evaluated the amount of red that had collected at the bottom of each capillary. FIG. 25 depicts the measured value of the "intensity of red color" in arbitrary units (AU) for the different concentrations of dense cells that were added to the normal blood. We found a good linear fit ($R^2$>0.995) to the data with an intercept set at 0. For the digital analysis, we found the limit of detection to be 2.8% dense cells by finding the value of the linear fit that provided a signal that was three standard deviations above the signal from normal blood (n=7). Below this concentration, it is possible for the digital analysis to confuse results from normal blood and SCD blood; this limit provides the false positives and false negatives that were observed in FIG. 18.

Alternative Methods to Diagnose SCD at the Point-of-Care.

Miligan et al. (C. Milligan et al., A non-electrolyte haemolysis assay for diagnosis and prognosis of sickle cell disease, *J. Physiol.* 6, 1463-1474 (2013)) have proposed monitoring hemolysis in non-electrolyte solutions as a means to diagnose sickle-cell disease. Quantifying hemolysis allows them to distinguish some genotypes and may provide a means to monitor certain clinical effects of SCD (Table 8). This test requires an hour of incubation, the use of an expensive tonometer, and optical density measurements; meeting these requirements in a point-of-care setting may be challenging.

The recent development of a paper-based test for SCD may provide an alternative low-cost diagnostic test. This test distinguishes Hb AA, Hb AS, and Hb SS visually by evaluating blood stains on paper after lysing and deoxygenating the hemoglobin (using a method similar to a solubility test). The visual signal can be analyzed by a scanner and correlates to the concentration of Hb S present. Even with the use of the digital analysis, the test is, however, less accurate than the AMPS-based tests at distinguishing individuals with Hb AS (non-disease) and Hb SC (disease); the Hb S concentration in these two genotypes can be very similar. In a person with Hb SC, the presence of Hb C leads to dehydration that induces sickling at a significant level that would not take place in a person with similar levels of Hb S, but with Hb AS.

TABLE 8

Comparison of methods to detect SCD.

| Ref. | Method | Time (min) | Differentiation AS/SS | AS/SC | SC/SS | AA/AS | Fieldable | Biophysical Indicator | Sample Prep. Free | Instrument Free | Instrument Cost | Unit Cost |
|---|---|---|---|---|---|---|---|---|---|---|---|---|
| This work | AMPS | 12 | ✓ | ✓ | ✓[a] | | ✓ | ✓ | ✓ | | $150-1,600 | $ 0.50 |
| 8 | Hemolysis | >60 | ✓ | | ✓ | | | ✓[b] | | | ~$10,000 | NA |
| 7 | Paper | 20 | ✓ | ✓[c] | ✓ | ✓ | ✓ | | | | $300-500 | $ 0.07[d] |
| † | Solubility | 5 | | | ✓ | ✓ | | | | ✓ | $0 | $ 3.00 |
| † | HPLC* | >120 | ✓ | ✓ | ✓ | ✓ | | | | | >$60,000 | $10.00 |
| † | HE* | >180 | ✓ | ✓ | ✓ | ✓ | | | | | >$10,000 | $ 3.00 |
| † | Genetic | >180 | ✓ | ✓ | ✓ | ✓ | | | | | >$20,000 | $ 1.00 |

[a]specifically, SCD-AMPS-3
[b]under investigation
[c]except in cases where hemoglobin S levels are close
[d]based on cost estimates for a similar paper test (23)
† based on market prices and product literature
*gold standard method.

Distinguishing between Hb SC and Hb AS is clinically important, especially in West Africa where both genes are common. In settings where Hb C is rare, such as eastern and southern Africa, this test could be a quick and inexpensive way to identify and distinguish between sickle-cell trait and disease.

Conventional Techniques of Separation by Density are not Suitable for Use in Field Settings.

Sequentially layering solutions with decreasing concentrations of a dense solute (e.g., sucrose, Percoll, arabinogalactan) creates a layered gradient in density. These gradients can separate blood into multiple subpopulations of cells of different densities. Layered gradients in density are not practical for use in a point-of-care test for several reasons: i) diffusion-driven homogenization of layers limits the long-term storage of a layered gradient, ii) agitation or mixing destroys a layered gradient, and iii) assembly of a gradient requires careful and tedious layering, and a high level of technical competence.

Centrifugation of blood over mixtures of phthalate esters provides a simpler method to characterize the density profile of blood. Mixtures of phthalate esters provide a range of single-density media. Upon centrifugation, blood cells either sink or float in a phthalate solution based on the difference in density between the cells and the solution. The immiscibility of the phthalates and water ensures that cells at the top of the phthalate are packed at an interface (i.e., a water/phthalate interface); cells layered over an aqueous medium would collect in a diffuse boundary between the plasma and the medium. Packing cells is an important characteristic for a separation to provide quantitative information. Comparison of the volume of packed cells above and below a phthalate provides a measure of the distribution of the density of cells. Although simpler to use than layered gradients, phthalate esters are unsuitable for point-of-care use for two reasons: i) they require a temperature-controlled centrifuge, and ii) they cannot distinguish more than two subpopulations of cells in a single system—a necessary ability to differentiate sub-types of SCD by density.

AMPS combines the best aspects of layered gradients and phthalate esters, while overcoming the principal drawbacks of each. Like layered gradients, AMPSs allow multiple sub-populations to be separated in a single system. Like phthalate esters, AMPSs concentrate cells at well-defined interfaces and are easy to use. Together, these characteristics allow centrifugation through AMPSs to distinguish blood from patients with SCD from normal blood by density and classify the two main subtypes of the disease.

Evaluation of a Density-Based Rapid Diagnostic Test for Sickle Cell Disease in a Clinical Setting in Zambia Timely diagnosis of sickle cell disease (SCD) is essential for the implementation of life-saving interventions. The lack of effective diagnostics in low-resource settings, however, means that over half of the more than 300,000 children born each year with SCD will die before five years of age.

Detecting the presence of dense, sickled cells could provide a sensitive and specific diagnostic of sickle cell disease. Density is a particularly relevant biophysical characteristic of sickle cell disease. The dehydration associated with the sickling of cells causes an increase in the density of an erythrocyte, from approximately 1.095 g cm$^{-3}$ to over 1.120 g cm$^{-3}$. The density of sickled cells is higher than the densest cells in the natural distribution of the density of erythrocytes.

We previously described the use of aqueous multiphase systems (AMPSs)—mixtures of polymers in water that form immiscible, liquid phases—to separate erythrocytes by density and provide a rapid visual diagnostic for SCD.

AMPSs are suitable for density-based separations at the point-of-care due to four characteristics: i) thermodynamic stability—step-gradients can be made centrally and will reform after disturbances from transportation, ii) fine resolution in density—the interface between the liquid phases of AMPSs provide a molecularly sharp step in density between phases with differences in density as low as 0.001 g cm$^{-3}$, iii) scalability—reproducible gradients can be made in capillary tubes appropriate for separating microliters of blood obtained from a fingerprick, and iv) low cost—using commercially available polymers, the cost of reagents, packaging, and labor per test is ~$0.50.

Although previous use of AMPS as a density-based diagnostic for sickle cell disease in a laboratory showed both sensitivity and specificity near or over 90%, implementing the test in point-of-care settings introduces several variables that may affect performance, such as packaging methods, quality control, storage and shipping conditions, user variability, and shelf-life.

To understand how these issues might affect the SCD-AMPSs tests, we undertook a 665 subject case-control study at the University Teaching Hospital in Lusaka, Zambia. Based on the results of this study, we identified three key issues that affected performance: 1) variability in the density of the bottom phase between batches, 2) clotting of blood samples, and 3) conditions of shipping and storage. After adjusting the rapid tests to address these issues, we performed a 150 subject case-control study at Harvard University to evaluate the performance of the test.

We also performed surveys of health workers in two rural health centers in a part of Zambia estimated to have a high prevalence of SCD. The surveys captured current knowledge of the disease, experience with other rapid tests, and feedback on the design of the proposed rapid test for SCD.

Rapid Test Design

Figure 27:
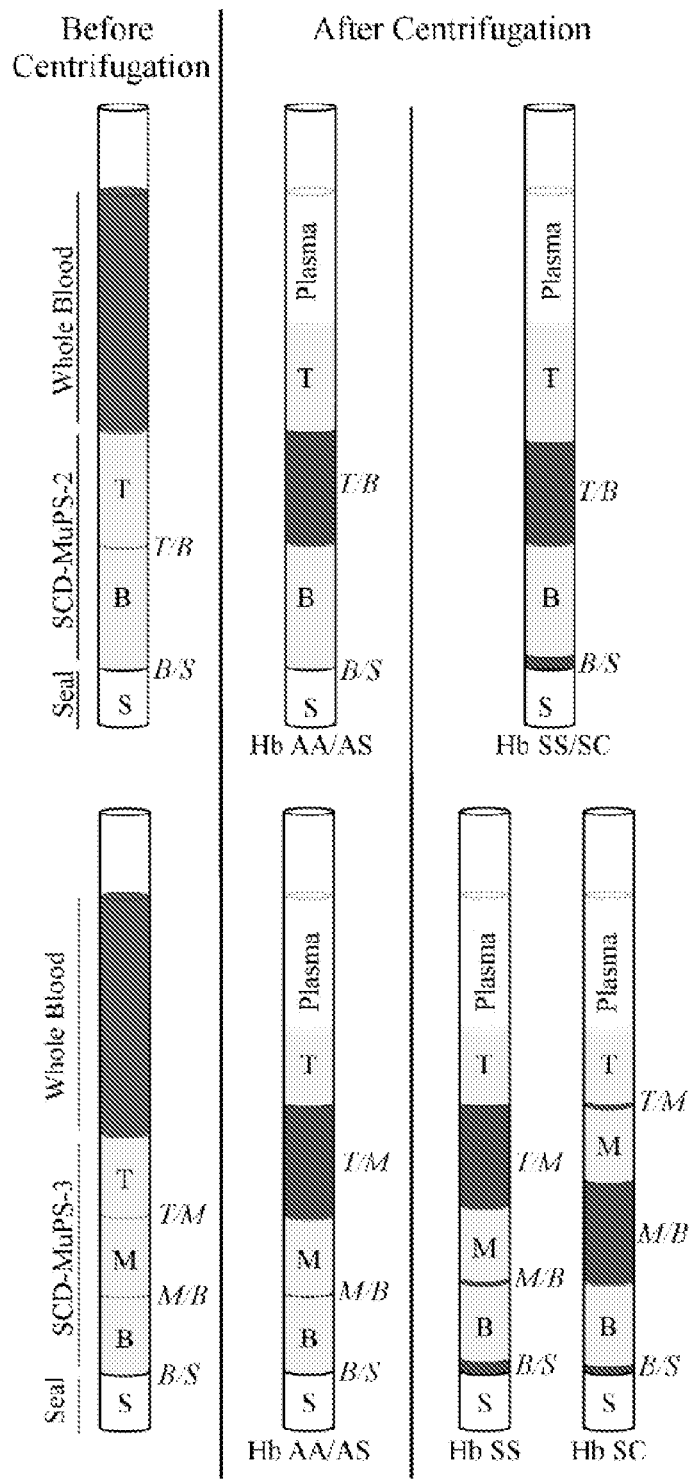
FIG. 27 shows two versions of the SCD-AMPS are designed to separate dense, sickled red blood cells from whole blood.

We evaluated two different density-based tests: a two-phase test (SCD-AMPS-2) and a three-phase test (SCD-AMPS-3) (FIG. 27). FIG. 27 illiterates both versions of the SCD-AMPS are designed to separate dense, sickled red blood cells from whole blood. Blood passes through the phases—T and B for SCD-AMPS-2 and T, M, and B for SCD-AMPS-3—upon centrifugation. If sickled cells are present, they collect at the B/S interface, providing a visual readout for the presence of SCD. In SCD-AMPS-3, the additional phase allows the discrimination of Hb SS from Hb SC by evaluating the distribution of red cells at the upper interfaces (T/M and M/B). Although SCD-AMPS-2 allows for a simpler interpretation, SCD-AMPS-3 provides a richer set of information about the distribution of densities of erythrocytes that can help distinguish between the two main genotypes of SCD: Hb SS and Hb SC.

We chose to evaluate both tests in the clinical trial to see if the simplicity of the two-phase test conferred a distinguishable advantage in clinical performance.

Figure 30:
FIG. 30 shows the schematic of fabrication process.
Figure 32:
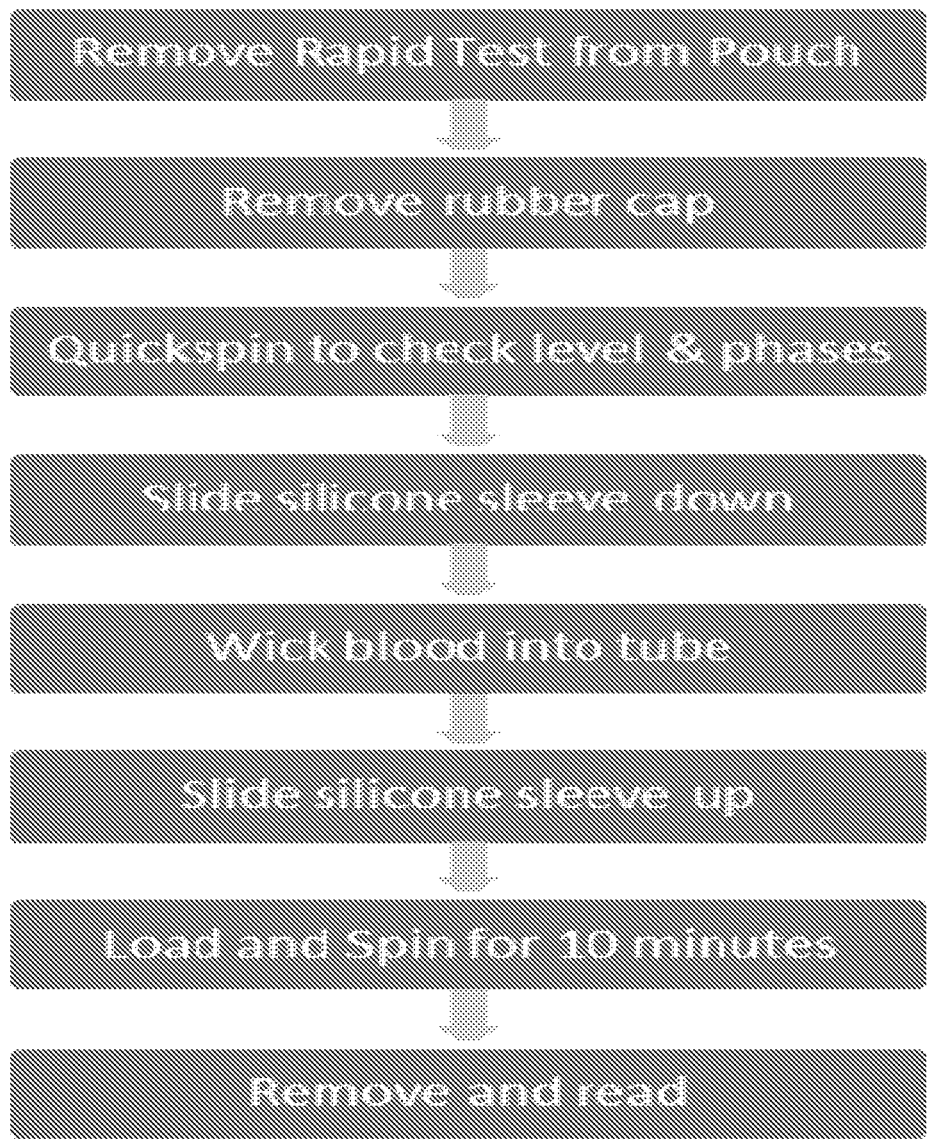
FIG. 32 shows the process to perform a rapid test for SCD with SCD-AMPS.

We used the design of the rapid test, SCD-AMPS, described previously with some additional modifications to enable rapid assembly of tests and improved durability for shipping and storage (see Supporting Information, FIGS. 30&32).

A mixture of 7.0% (w/v) poly(ethylene glycol) (PEG) with a molecular weight (MW) of ~20 kD, 10.3% (w/v) Ficoll with a MW of ~400 kD, and 9.1% (w/v) Nycodenz formed SCD-AMPS-2 ($\rho_{top}$=1.078 g cm$^{-3}$ and $\rho_{bot}$=1.129 g cm$^{-3}$). Similarly, a mixture of 3% (w/v) PEG with a MW of ~20 kD, 10% (w/v) dextran with a MW of ~500 kD, 5%

(w/v) polymer of partially hydrolyzed poly(vinyl acetate) (containing 75% —OH and 25% —OCOCH$_3$ groups) with a MW of ~3 kD, and 8.7% (w/v) Nycodenz, formed SCD-AMPS-3 ($\rho_{top}$=1.077 g cm$^{-3}$, $\rho_{mid}$=1.108 g cm$^{-3}$, and $\rho_{bot}$=1.120 g cm$^{-3}$). We buffered the systems and used NaOH and HCl to adjust the pH of the solutions and NaCl to adjust the osmolality.

FIG. 32 outlines the process to perform a rapid test for an end-user. The self-forming steps gradient in density allows the end-user to use the AMPS out of a packet without needing to mix reagents or pipette solutions. Whole blood wicks directly into the capillary; no further handling of blood is necessary. Preparative steps common to other techniques, such as lysis or exposure to reagents to deoxygenate hemoglobin, are not needed. These characteristics of the test reduce risks for biohazards and user error.

The polycarbonate capillary tubes that house the rapid test are preloaded with AMPS and sealed on one end with white clay. The white seal provides an effective background to contrast with the red cells.

A volume of ~5 µL of blood enters the rapid test via capillary action as a result of the pre-punched hole in the side of the capillary. Sliding a silicone sleeve over the hole prevents the blood from leaking, and centrifugation accelerates the density-based separation of red blood cells over the AMPS. We used a 3D printed mold and a pushpin to make repeatable holes; this standardization allowed us to load a reproducible volume of blood with a coefficient of variance (CV) of 4%.

After 10 minutes of centrifugation, evaluating the interfaces of AMPS for the visible presence of red cells provides a means to identify SCD and, in the case of SCD-AMPS-3, to distinguish between the two main genotypes of SCD (FIG. 27).

Development of Methods to Pack, Store, and Ship SCD-AMPS Tests

We performed a series of accelerated storage tests using various packaging materials and methods.

We found that foil-lined pouches partially filled with water and then sealed with an impulse sealer minimized evaporation of the SCD-AMPS systems.

To minimize variables for this clinical trial, the packaged samples were refrigerated after packaging at 4-8° C. and shipped on ice to Zambia. Samples were refrigerated at UTH and brought to room temperature on the day of use.

Characteristics of Population for the Clinical Study

The initial study in Zambia included 665 children that were seen as out-patients or in-patients during the period of the study in the Department of Paediatrics and Child Health and the out-patient haematology clinic for SCD patients.

The second study was performed in the U.S. and included 150 children seen at MUSC.

We used the broad inclusion and exclusion criteria found in Table 9, with further criteria for specific subsets of the study population: Subset 1) children fitting the inclusion criteria with the additional inclusion criteria of being over 1 year old and confirmed as SCD positive, Subset 2) children fitting the inclusion criteria above with the additional inclusion criteria of not having SCD, Subset 3) children fitting the inclusion criteria with the additional inclusion criteria of being below 1 year old and confirmed as SCD positive, and Subset 4) children fitting inclusion criteria with the exception of the first exclusion criteria who were over 1 year old, confirmed as SCD positive, and had undergone a sickling crisis within the last 48 hours.

TABLE 9

Inclusion and Exclusion Criteria for Study

| Inclusion Criteria | Exclusion Criteria |
| --- | --- |
| Children aged 6 months up to, but not including 18 years | Children who have had a sickling crisis one month prior to the blood draw (except for the subset specified below) |
| Children with clinical indication for a blood draw | |
| Children whose parents give a written informed consent to be part of the study | Children who have been treated with hydroxyurea in the last four months |
| Children whose parent consent to have blood draw for clinical purposes and for the study | |

The first two subsets were recruited to achieve a population with roughly 50% SCD positive participants. These participants provide the main population of interest in the study.

The last two subsets were of interest to test potential confounding factors for a field diagnostic. Before achieving 1 year of age, infants may still have a large proportion of Hb F in their blood. This could reduce the percent of dense cells present and reduce the sensitivity of a density-based assay for this subset. An evaluation of this subset allowed us to determine whether there was a difference between the predictive value of the SCD-AMPS test for children below 1 year of age and children above 1 year of age. Similarly, participants who have SCD and have recently experienced a sickle crisis may have cleared all dense cells in their blood.

Table 10 details the final populations recruited and basic demographic information.

TABLE 10

Basic Characteristics of the Study Population

| Population | Zambia Subjects | U.S. Subjects |
| --- | --- | --- |
| Positive (HbSS) | | |
| ≥1 yr, non-crisis | 295 | 60 |
| <1 yr, non-crisis | 25 | 20 |
| >1 yr, crisis | 40 | 20 |
| Negative | | |
| All | 304 | 50 |
| HbAA | 225 | 35 |
| HbAS | 79 | 15 |
| TOTAL | 665 | 150 |

Evaluation of Samples by Standard Methods

All samples in Zambia were evaluated by hemoglobin electrophoresis (HE) and full blood counts (FBC) were performed. Samples from MUSC were evaluated by isoelectric focusing (IEF) and high performance liquid chromatography (HPLC) at the New England Newborn Screening Center in Boston, Mass. In both the initial study in Zambia and the second study at Harvard, the rapid tests and confirmatory tests occurred at different laboratories and were performed by separate personnel to ensure proper blinding of the rapid test results. During the pilot phase of the study, we established the time between sample collection and testing for each type of analysis, as well as other criteria to deem samples unusable (e.g. visible clots forming).

Results from HE and FBC allowed us to classify subjects as SCD, sickle cell trait, or non-SCD based on detecting the presence and quantify of Hb S as well as evaluation of the red blood cell indices.

Visual Inspection and Validation

After a one day training, readers were instructed to evaluate each test by classifying the amount of red color that was visible at each interface using the following five criteria: 1) majority of red cells, 2) full layer of red cells, 3) over half layer of red cells, 4) less than half layer of red cells, or 5) no red cells detectable.

We chose to use these five classifications rather than a simple binary reading in order to understand how different cut-offs could affect test performance. Although the five levels add complexity to interpretation, they allow us greater resolution of the potential differences in the densities of cells.

Field Visits to Obtain Feedback from End-Users

We chose two rural health centers (RHCs) in the Luwingu District of Northern Province, Luena RHC and Ipusukilo RHC, to perform demonstrations of the rapid test and to gather feedback on the use of the test from the clinical staff.

The Northern Province is estimated to have a high prevalence of SCD. The two centers chosen in the Northern Province were chosen for their remote location with no access to grid electricity or paved roads.

At each site, over the course of two days, study staff members provided an information session about sickle cell disease and management for the clinic staff and community, as well as an information session and demonstration of the SCD-AMPS-2 rapid test. Following these sessions, a survey was taken of the staff members to assess their familiarity with other rapid tests and their thoughts on the SCD-AMPS-2 rapid test.

The Packaging Method Prevented the Evaporation of Samples.

A total of 624 rapid tests were evaluated after removal from packaging for modes of failure before use. We found two modes of failure of the rapid test after packaging, shipping, and storing. In 24 of the tests, the plug from the removable rubber cap on the tube snapped, leaving the capillary plugged and unusable. Nine rapid tests had liquid levels that did not match the marker line; six were underfilled and three were over-filled. The discrepancy may have been due to improper coverage with the silicone seal allowing water to either enter or leave the capillary tube. Notably, all tests formed the correct number of phases as verified by visual inspection. The total failure rate for the packaging of the rapid tests was 5.3%.

Performance of SCD-AMPS

Figure 28:
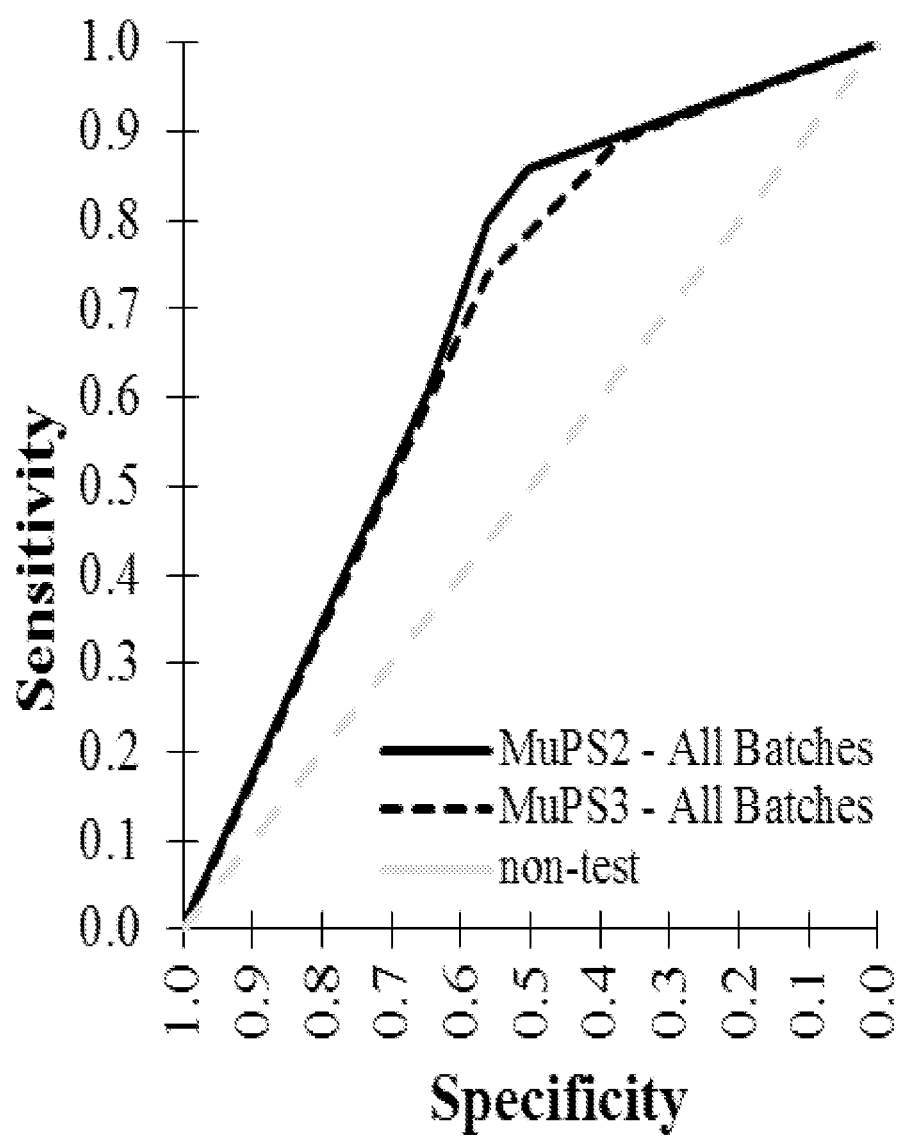
FIG. 28 shows Receiver Operating Characteristic (ROC) curve of SCD-AMPS-2 and SCD-AMPS-3 on all data from Zambia which shows fair discriminative ability.

We calculated the sensitivity and specificity of SCD-AMPS-2 and SCD-AMPS-3 using each of the five classifications for the level of red cells below the bottom interface. We constructed receiver operating characteristic curves using these calculations (FIG. 28). FIG. 28 illustrates the Receiver Operating Characteristic (ROC) curve of SCD-AMPS-2 and SCD-AMPS-3 on all data from Zambia shows fair discriminative ability. The amount of red cells below the bottom phase of each test was evaluated by eye and classified on a five point scale. Setting each classification showed similar sensitivity and specificities for both of the rapid tests evaluated. In general, the specificity was found to be lower than the sensitivity of the tests. The area under the curve (AUC) for SCD-AMPS-2 was 0.68 and for SCD-AMPS-3 was 0.67. This indicates an ability to discriminate sickle cell disease, but is lower than previous estimates of performance for these systems using a digital analysis (AUC>0.95).

Part of the reduced specificity could be attributed to the bias of the readers at UTH to read samples with a higher level of redness compared to the expert reader. The use of a cell phone camera or portable scanner to analyze the rapid tests would eliminate the subjectivity associated with human readers.

The trial in Zambia introduced several other variables that may have played a role in the lower performance, and are potential areas for improvement for development of a point-of-care diagnostic. These variables include: variability in batches of AMPS, variability in manufacturing of rapid test, shipping and storage conditions, and clotting of blood samples. We analyzed each of these variables and concluded that three of them were the most probably causes of the reduced performance: 1) storage and shipping conditions, 2) variability in the density of the bottom phase between batches, and 3) clotting.

We designed a series of experiments to test each of these variables. After making improvements to our production and storage protocols, we created three new batches of both SCD-AMPS-2 and SCD-AMPS-3 and tested them on samples from 150 subjects from MUSC.

Capabilities of Rural Health Centers

A point-of-care diagnostic provides benefit when it is coupled to effective interventions. Simple interventions (e.g., pneumococcal vaccine and prophylactic antibiotics) for sickle cell disease exist, and we sought to assess whether rural health centers in Zambia had the capabilities to perform an SCD-AMPS test and provide appropriate interventions.

Figure 29A:
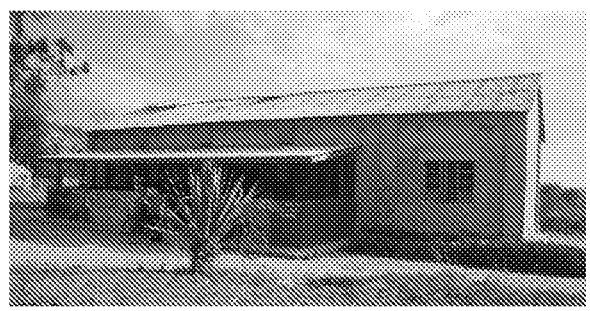
FIGS. 29A-29B show the SCD-AMPS rapid tests were demonstrated in rural health centers (FIG. 29A). All the equipment necessary to run the rapid test in a rural clinic fits inside a backpack (FIG. 29B).
Figure 29B:
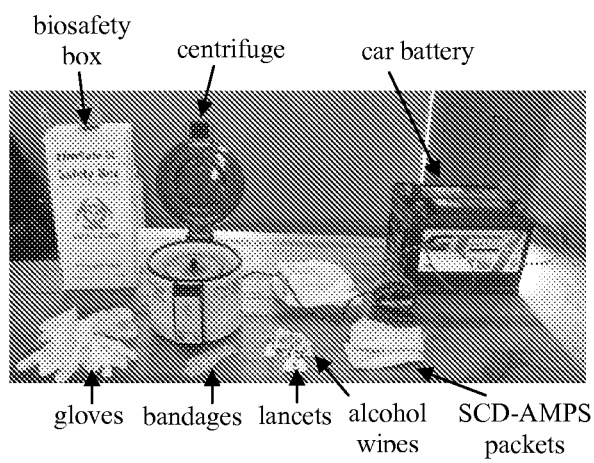

FIG. 29 shows that the SCD-AMPS rapid tests were demonstrated in rural health centers (29A). All the equipment necessary to run the rapid test in a rural clinic fits inside a backpack (29B). Working with the U.S. Peace Corps in Zambia we identified two Rural Health Centers—Luena RHC (FIG. 29A) and Ipusukilo RHC—in Northern Province to carry out demonstrations of the rapid test and an assessment of capabilities to care for patients with SCD. Observations at UTH and previous work in Zambia led us to believe that there might be a high prevalence of SCD in Northern Province.

Our survey indicated that the clinic staff at both RHCs was well acquainted with rapid tests for malaria, HIV, and syphilis and had a supply of tests. Neither clinic had a microscope or capabilities to diagnose SCD.

Although both clinics lacked the infrastructure to perform transfusions and did not have morphine, they did have the ability to provide several other interventions that have been shown to reduce mortality and ease symptoms of sickle cell disease, including folic acid supplements, intravenous fluids, antibiotics, antimalarials, and pneumococcal vaccine (PCV) (Table 11).

TABLE 11

Performance of SCD-AMPS on subjects with potentially confounding factors.

| Concurrent Condition | Criteria | # SCD Positive | # SCD Negative | Sensitivity | CI | Specificity | CI |
|---|---|---|---|---|---|---|---|
| Infants | 6-12 months | 25 | 1 | | | | |
| High Hb F | Hb F >20% | 41 | 5 | | | | |
| Anemic | TBD | | | | | | |
| Alpha thal | TBD | | | | | | |
| Recent crisis | <48 hours | 40 | — | | | | |

Feedback on SCD-AMPS from End-Users

The SCD-AMPS tests were designed to use minimal equipment in order to be used in low-level clinics. Apart from the SCD-AMPS tests themselves, the only other equipment necessary to perform a test is a microhematocrit centrifuge. We used a centrifuge (CritSpin, Iris Sample Processing) with a custom adapter to run off of a car battery. The tests, supplies to safely perform a fingerprick, the centrifuge, and the battery all fit into a backpack (FIG. 29B) and were transported from Lusaka to the RHCs by bus, shared taxis, and hitch-hiking.

We assessed the ability of the clinical staff to perform SCD-AMPS test by presenting an education session and demonstration of the rapid test with a focus on four steps: i) checking rapid tests for defects, ii) loading blood, iii) centrifugation of tests, and iv) interpretation of rapid test results.

The staff was able to handle the rapid test and ask questions about the protocol and interpretation. Afterwards, participants were surveyed to assess their comfort with each of the four steps. Their familiarity and comfort with common lateral flow rapid tests was also assessed as a benchmark for usability. Participants rated tests using a five point scale with 1 being "very difficult to use", 3 being "okay to use", and 5 being "very easy to use."

The clinical staff rated the ease of use of lateral flow tests, such a rapid diagnostic test for malaria, as 3.4.

Evaluation of the rapid test was broken into four sections: Step 1) initial setup, Step 2) loading blood, Step 3) running tests (centrifugation), and Step 4) reading results. Each step was rated for ease on the same 5 point scale. The initial set up was given an average rating of 3.3. The loading step was given an average rating of 3.4. Running the tests was given an average rating of 3.3. Reading results was given an average rating of 3.3. Every step was, thus, comparable to the ease of use of existing rapid tests.

A density-based diagnostic for sickle cell disease using AMPS has the potential to fill a critical healthcare gap in low-resource settings. We have demonstrated that with appropriate controls and usage, SCD-AMPS can provide the ability to discriminate between patients that have sickle cell disease and patients that do not. Initial demonstrations with staff at rural clinics in Zambia indicate that SCD-AMPS tests are comparable to standard rapid diagnostic tests for malaria in ease-of-use.

Although sensitivity and specificity are not as high as those of gold standard methods like HPLC and IEF, these tests could provide actionable information when coupled with patient history and clinical presentation.

Solubility tests, such as Sickledex, are often used to screen for SCD in clinics in India and sub-Saharan Africa, but they cannot differentiate between the non-disease, carrier sickle cell trait and SCD. SCD-AMPS does discriminate between SCD and sickle cell trait.

The diagnostic ability of the test depends on the presence of dense, sickled cells in the blood. These cells will not be present in newborns, and hence SCD-AMPS would not be appropriate for neonatal screening. After 6 months, however, the amount of dense cells present is sufficient to allow use of SCD-AMPS. Coupled with vaccination programs, screening children for SCD with an SCD-AMPS test could provide useful information on prevalence.

The capability to diagnose sickle cell disease at primary health centers and rural health centers in places like Zambia would allow the targeted use of appropriate interventions (e.g., vaccines, prophylactic penicillin, and supplements for folate and iron). These interventions could reduce child mortality and improve the quality of life for those that live with undiagnosed sickle cell disease.

FIG. 30 outlines the fabrication of a single test. We puncture a hole in the side of a polycarbonate capillary tube at a prescribed height using a customized holder and push-pin (FIG. 32). A silicone sleeve slides over the tube to open or close the hole. Using a pipette, we load a pre-mixed solution of an SCD-AMPS solution into the tube and then seal one end with white sealing clay (Critoseal, Leica). To ensure the sealing clay does not fail under during shipping or storage, we dipped the sealed end of the tube in Krazy Glue and allowed the glue to set. After two minutes of centrifugation at 13,000 g, the phases of the SCD-AMPS system separated. We used a marker to indicate the highest level of the liquid in the tube at the time of fabrication as a quality control measure that could be checked before use. To reversibly seal the open end of the capillary, we used white rubber capillary covers (Critocaps, Leica).

Prototype AMPS for Diagnosis of Sickle Cell

Figure 33:
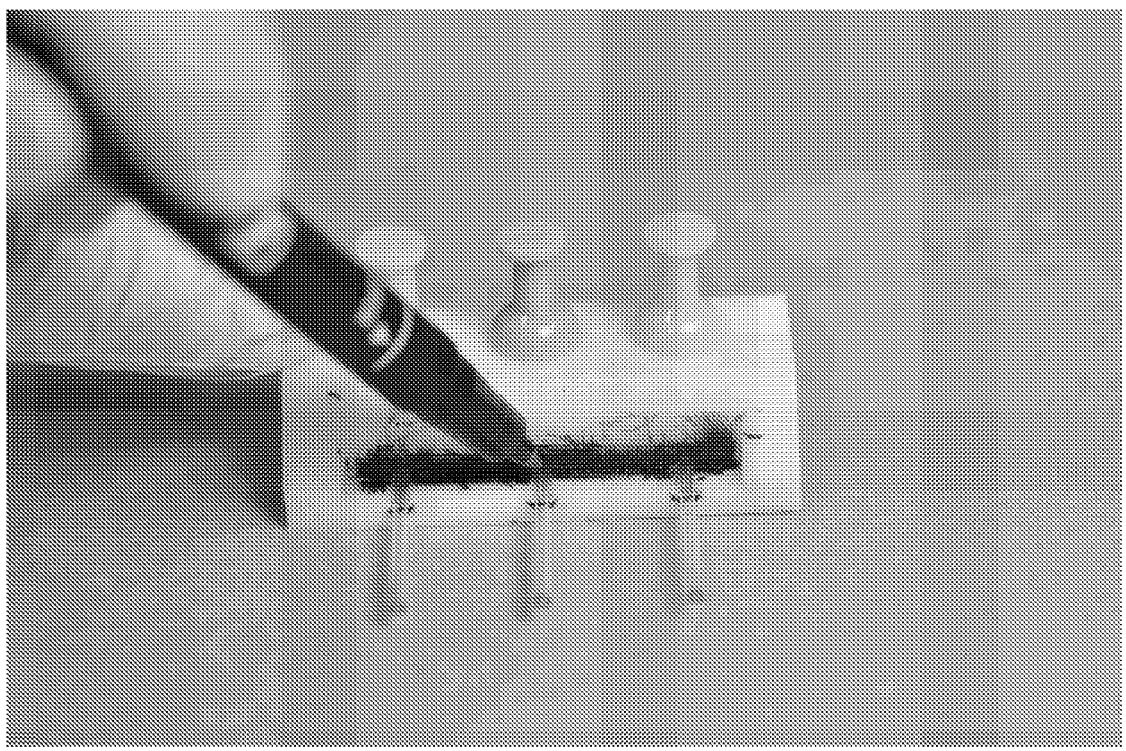
FIG. 33 shows the volume control and metering step in the prototype development of an AMPS for sickle cell diagnosis.
Figure 34:
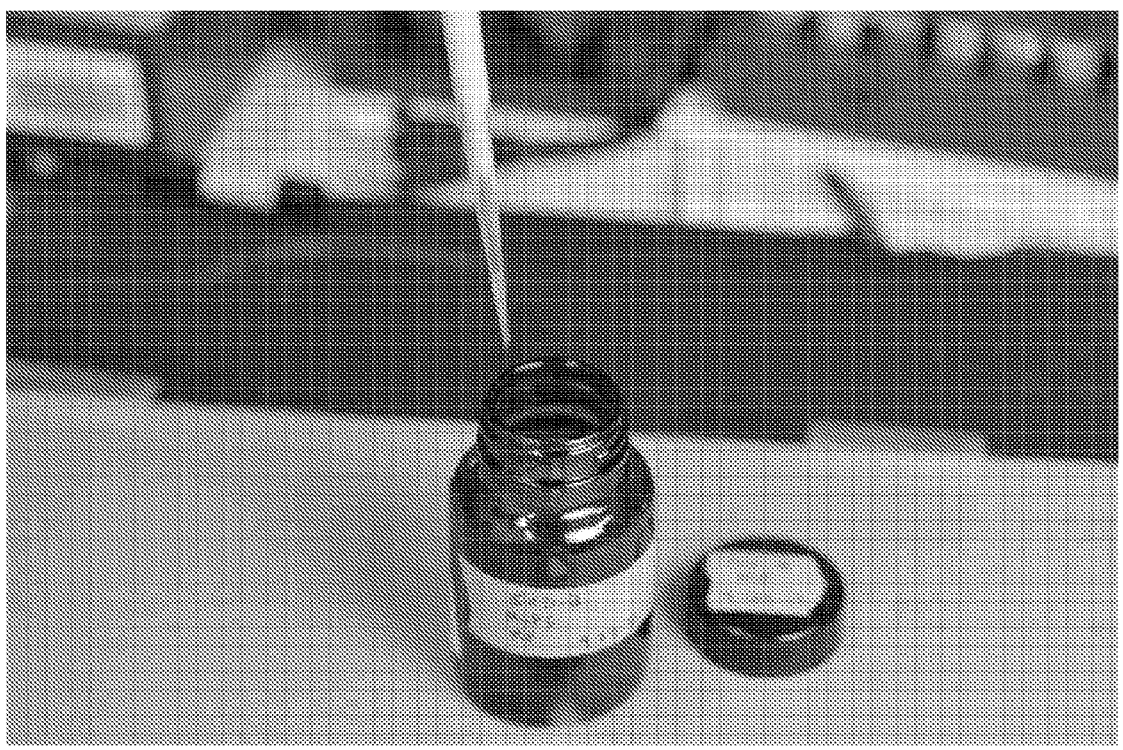
FIG. 34 shows the step of loading the AMPS in the prototype development of an AMPS for sickle cell diagnosis.
Figure 37:
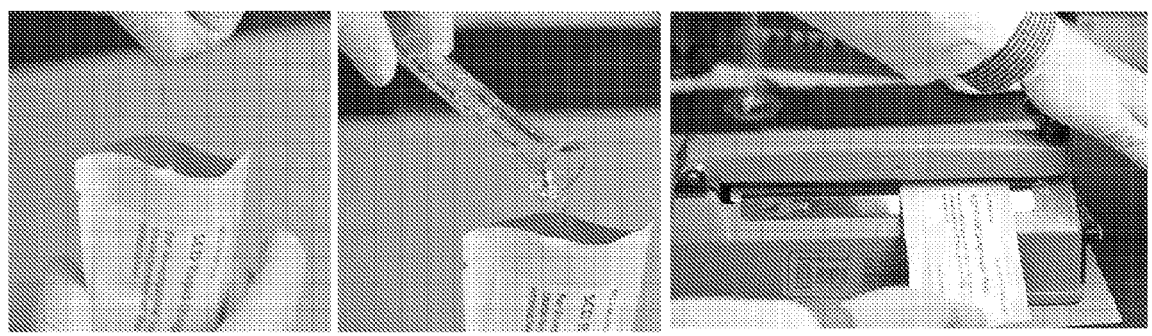
FIG. 37 shows the packing step in the prototype development of an AMPS for sickle cell diagnosis.
Figure 38:
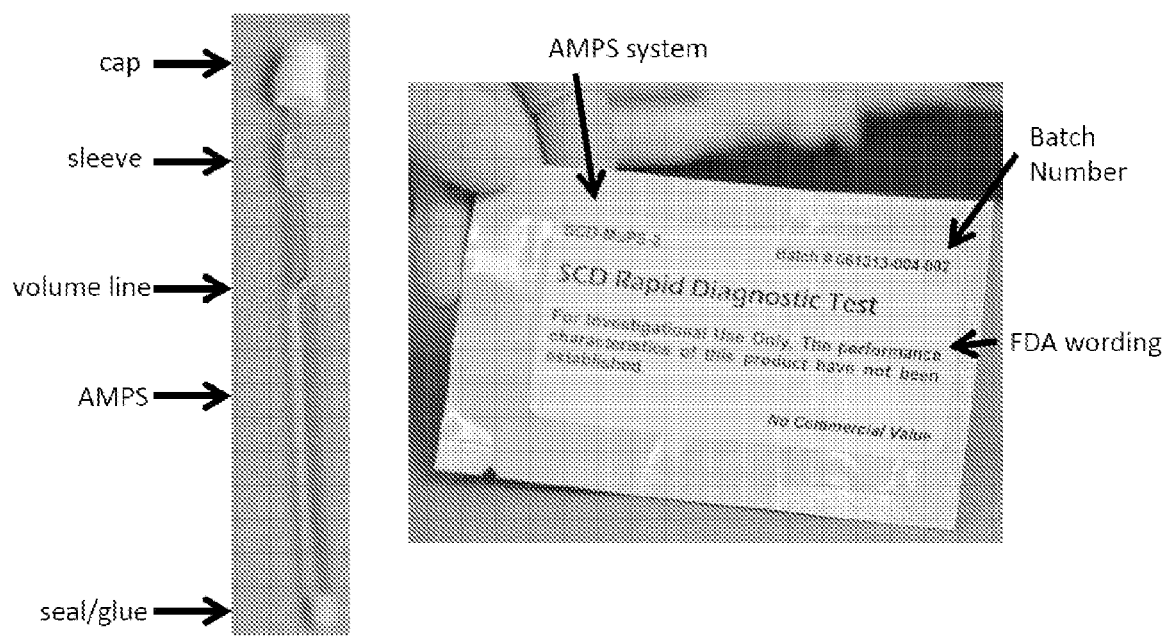
FIG. 38 shows a final prototype of an AMPS for sickle cell diagnosis.

FIGS. 33-38 illustrate AMPS for Diagnosis of Sickle Cell Anemia Sample Packing and Storage Procedure. Specifically, the capillary tube is loaded into a 3D printed mold and a hole is punched near the top of the tube using a push pin. A pen is used to mark the "fill" line for loading the AMPS (FIG. 33). AMPS is loaded into the tube to the fill line from the bottom using a pipette (FIG. 34). The bottom of the tube is sealed with Critoseal clay which is then covered by a layer of Krazy Glue. A silicone rubber sleeve (~0.7 cm) is placed over to punched hole and then a Critocap is used to cover the top of the tube (FIG. 35). We tried to use hard wax to cover the top of the tube but found evaporation was more of a problem when we did that. The tubes are centrifuged for 2 minutes and then the "fill" line is removed with methanol and a new line is drawn to mark to new solution level (this level changes because of the clay seal at the bottom) (FIG. 36). Twelve tubes are loaded into a foil-lined pouch which is filled with 4 ml PBS buffer, evacuated of excess air by hand, and sealed with a heat sealer (FIG. 37). FIG. 38 shows the final prototyping of the AMPS.

We claim:

1. An aqueous multi-phase system for diagnosis of sickle cell disease, comprising two or more phase-separated phases comprising:
    a first aqueous phase comprising a first phase component and having a first density between about 1.025 $g/cm^3$ and about 1.095 $g/cm^3$; and
    a second aqueous phase comprising a second phase component and having a second density between about 1.100 $g/cm^3$ and about 1.140 $g/cm^3$;
    wherein
    the first density is lower than the second density; and
    each of the first and second phase components comprises at least one polymer.

2. The aqueous multi-phase system of claim 1, wherein the first density is about 1.025-1.090 $g/cm^3$, 1.025-1.080 $g/cm^3$, 1.025-1.075 $g/cm^3$, 1.025-1.070 $g/cm^3$, 1.025-1.065 $g/cm^3$, 1.025-1.060 $g/cm^3$, 1.025-1.055 $g/cm^3$, 1.025-1.050 $g/cm^3$, 1.030-1.080 $g/cm^3$, 1.030-1.075 $g/cm^3$, 1.030-1.070 $g/cm^3$, 1.030-1.065 $g/cm^3$, 1.030-1.060 $g/cm^3$, 1.030-1.055 $g/cm^3$, 1.030-1.050 $g/cm^3$, 1.040-1.080 $g/cm^3$, 1.040-1.075 $g/cm^3$, 1.040-1.070 $g/cm^3$, 1.040-1.065 $g/cm^3$, 1.040-1.060 $g/cm^3$, 1.040-1.055 $g/cm^3$, or 1.040-1.050 $g/cm^3$.

3. The aqueous multi-phase system of claim 1, wherein the first density is about 1.025-1.030, 1.035-1.050, 1.055-1.070, or 1.075-1.080 $g/cm^3$.

4. The aqueous multi-phase system of claim 1, wherein the second density is about 1.110-1.140 $g/cm^3$, 1.110-1.130 $g/cm^3$, 1.110-1.125 $g/cm^3$, 1.110-1.120 $g/cm^3$, 1.115-1.125 $g/cm^3$, 1.115-1.120 $g/cm^3$, or 1.120-1.125 $g/cm^3$.

5. The aqueous multi-phase system of claim 1, wherein the second density is about 1.115-1.130 $g/cm^3$.

6. The aqueous multi-phase system of claim 1, wherein the first and second densities are about 1.075-1.0798 g/cm$^3$ and 1.120-1.129 g/cm$^3$, respectively.

7. The aqueous multi-phase system of claim 1, further comprising:
a third aqueous phase comprising a third phase component and having a third density between about 1.075 g/cm$^3$ and about 1.120 g/cm$^3$;
wherein
the third density is higher than the first density but lower than the second density; and
the third phase component comprises at least one polymer.

8. The aqueous multi-phase system of claim 7, wherein the third density is about 1.085-1.110 g/cm$^3$, 1.090-1.110 g/cm$^3$, 1.095-1.110 g/cm$^3$, 1.100-1.110 g/cm$^3$, 1.105-1.110 g/cm$^3$, 1.085-1.105 g/cm$^3$, 1.090-1.105 g/cm$^3$, 1.095-1.105 g/cm$^3$, 1.100-1.105 g/cm$^3$, 1.085-1.100 g/cm$^3$, 1.090-1.100 g/cm$^3$, 1.095-1.100 g/cm$^3$, 1.085-1.095 g/cm$^3$, or 1.090-1.095 g/cm$^3$.

9. The aqueous multi-phase system of claim 7, wherein the first, third, and second densities are about 1.075-1.083 g/cm$^3$, 1.105-1.110 g/cm$^3$, and 1.115-1.125 g/cm$^3$, respectively.

10. The aqueous multi-phase system of claim 1, wherein the first, second, and third phase components are each selected from the group consisting of Caboxy-polyacrylamide, Dextran, Ficoll, N,N-dimethyldodecylamine N-oxide, poly(2-ethyl-2-oxazoline), poly(acrylic acid), poly(ethylene glycol), poly(methacrylic acid), poly(vinyl alcohol), polyacrylamide, polyethyleneimine, hydroxyethyl cellulose, poly(2-acrylamido-2-methyl-1-propanesulfonic acid), polyvinylpyrrolidone, Nonyl, polyallylamine, (hydroxypropyl) methyl cellulose, diethylaminoethyl-dextran, nonylphenol polyoxyethylene 20, copolymer, terpolymer, block copolymer, random polymer, linear polymer, branched polymer, crosslinked polymer, and dendrimer system thereof.

11. The aqueous multi-phase system of claim 1, wherein the first and second components are PEG and Ficoll or PEG and PVA, respectively.

12. The aqueous multi-phase system of claim 1, wherein the first, third, and second components are PEG, dextran, and PVA, respectively.

13. The aqueous multi-phase system of claim 1, wherein the concentration of the first phase component in the first phase or the concentration of the second phase component in the second phase is between about 1-40% (w/v).

14. The aqueous multi-phase system of claim 1, wherein the concentration of the first phase component in the first phase or the concentration of the second phase component in the second phase is about 5%-10%, 10%-15%, or 15%-25% (w/v).

15. The aqueous multi-phase system of claim 7, wherein the concentration of the third phase component in the third phase is between about 1-40%, 5%-10%, 10%-15%, or 15%-25% (w/v).

16. The aqueous multi-phase system of claim 1, wherein the aqueous multi-phase system is isotonic.

* * * * *